(12) United States Patent
Lee et al.

(10) Patent No.: US 8,569,252 B2
(45) Date of Patent: Oct. 29, 2013

(54) NUCLEOLIN SPECIFIC APTAMER AND USE THEREOF

(75) Inventors: Jung-Hwan Lee, Pohang-si (KR); Soon-Hag Kim, Seongnam-si (KR); Mi-Jin Kwon, Busan (KR); Hyun-Gu Kang, Daegu (KR); Sung-Ho Ryu, Pohang-si (KR); Jong-In Kim, Pohang-si (KR); Youn-Dong Kim, Pohang-si (KR); Young-Chan Chae, Pohang-si (KR); Sung-Key Jang, Pohang-si (KR); Jong-Hun Im, Pohang-si (KR); Sun-Hak Lee, Pohang-si (KR); Hye-Jung Lee, Daegu (KR); Eun-Jung Jang, Pohang-si (KR); Ki-Seok Kim, Pohang-si (KR)

(73) Assignees: Postech Academy-Industry Foundation, Pohang (KR); Posco, Pohang-Shi (KR)

( * ) Notice: Subject to any disclaimer, the term of this patent is extended or adjusted under 35 U.S.C. 154(b) by 170 days.

(21) Appl. No.: 12/759,813

(22) Filed: Apr. 14, 2010

(65) Prior Publication Data

US 2010/0317723 A1 Dec. 16, 2010

Related U.S. Application Data

(60) Provisional application No. 61/169,348, filed on Apr. 15, 2009.

(51) Int. Cl.
*C12N 15/11* (2006.01)

(52) U.S. Cl.
USPC ........................................................ 514/44 A

(58) Field of Classification Search
USPC ........................................................ 514/44 A
See application file for complete search history.

(56) References Cited

U.S. PATENT DOCUMENTS

| | | | |
|---|---|---|---|
| 6,723,706 B2 * | 4/2004 | Uhlmann et al. | 514/44 A |
| 2005/0187176 A1 * | 8/2005 | Bates et al. | 514/44 |
| 2009/0098549 A1 * | 4/2009 | Schneider et al. | 435/6 |

OTHER PUBLICATIONS

Lee, K. Y. et al., Bioimaging of Nucleolin Aptamer-Containing 5-(N-benzylcarboxyamide)-2'-deoxyuridine More Capable of Specific Binding to Targets in Cancer Cells, Journal of Biomedicine and Biotechnology, Articel ID 168306, 9 pages, Epub Mar. 1, 2010.
Soundararajan, S. et al., Plasma Membrane Nucleolin Is a Receptor for the Anticancer Aptamer AS1411 in MV4-11 Leukemia Cells, Molecular Pharmacology, vol. 76, No. 5, pp. 984-991, Nov. 2009.
Soundararajan, S. et al., The Nucleolin Targeting Aptamer AS1411 Destabilizes Bcl-2 Messenger RNA in Human Breast Cancer Cells, Cancer Research, vol. 68, No. 7, pp. 2358-2365, Apr. 1, 2008.
Choi, E. W. et al., Cancer-selective antiproliferative activity is a general property of some G-rich oligodeoxynucleotides, Nucleic Acids Research, vol. 38, No. 5, pp. 1623-1635, Mar. 2010.

* cited by examiner

*Primary Examiner* — Brian Whiteman
(74) *Attorney, Agent, or Firm* — Lexyoume IP Meister, PLLC.

(57) ABSTRACT

Improved G-rich oligonucleotide (GRO) aptamers specific to nucleolin, a method of preparing the aptamers, and a use of the aptamers for diagnosing and/or treating a nucleolin-associated disease, are provided.

8 Claims, 30 Drawing Sheets

SEQUENCE LISTING

```
<160> NUMBER OF SEQ ID NOS: 210

<210> SEQ ID NO 1
<211> LENGTH: 29
<212> TYPE: DNA
<213> ORGANISM: Artificial Sequence
<220> FEATURE:
<223> OTHER INFORMATION: GRO29A aptamer

<400> SEQUENCE: 1
tttggtggtg gtggttgtgg tggtggtgg                              29
```

<210> SEQ ID NO 2
<211> LENGTH: 26
<212> TYPE: DNA
<213> ORGANISM: Artificial Sequence
<220> FEATURE:
<223> OTHER INFORMATION: AS1411 aptamer

<400> SEQUENCE: 2
ggtggtggtg gttgtggtgg tggtgg                                           26

<210> SEQ ID NO 3
<211> LENGTH: 29
<212> TYPE: DNA
<213> ORGANISM: Artificial Sequence
<220> FEATURE:
<223> OTHER INFORMATION: G-rich oligonucleotide (GRO)
<220> FEATURE:
<221> NAME/KEY: misc_feature
<222> LOCATION: 1..3
<223> OTHER INFORMATION: Ns at 5' end are independently selected from
      the group consisting of A, T/U, C, and G, or absent

<400> SEQUENCE: 3
nnnggtggtg gtggttgtgg tggtggtgg                                        29

<210> SEQ ID NO 4
<211> LENGTH: 29
<212> TYPE: DNA
<213> ORGANISM: Artificial Sequence
<220> FEATURE:
<223> OTHER INFORMATION: aptamer 1642-8 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 1
<223> OTHER INFORMATION: n is BzdU

<400> SEQUENCE: 4
nttggtggtg gtggttgtgg tggtggtgg                                        29

<210> SEQ ID NO 5
<211> LENGTH: 29
<212> TYPE: DNA
<213> ORGANISM: Artificial Sequence
<220> FEATURE:
<223> OTHER INFORMATION: aptamer 1642-9 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 2
<223> OTHER INFORMATION: n is BzdU

<400> SEQUENCE: 5
tntggtggtg gtggttgtgg tggtggtgg                                        29

<210> SEQ ID NO 6
<211> LENGTH: 29
<212> TYPE: DNA
<213> ORGANISM: Artificial Sequence
<220> FEATURE:
<223> OTHER INFORMATION: aptamer 1642-10 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 3
<223> OTHER INFORMATION: n is BzdU -continued

```
<400> SEQUENCE: 6
ttnggtggtg gtggttgtgg tggtggtgg                                            29

<210> SEQ ID NO 7
<211> LENGTH: 29
<212> TYPE: DNA
<213> ORGANISM: Artificial Sequence
<220> FEATURE:
<223> OTHER INFORMATION: aptamer 1642-11 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 6
<223> OTHER INFORMATION: n is BzdU

<400> SEQUENCE: 7
tttggnggtg gtggttgtgg tggtggtgg                                            29

<210> SEQ ID NO 8
<211> LENGTH: 29
<212> TYPE: DNA
<213> ORGANISM: Artificial Sequence
<220> FEATURE:
<223> OTHER INFORMATION: aptamer 1642-12 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 9
<223> OTHER INFORMATION: n is BzdU

<400> SEQUENCE: 8
tttggtggng gtggttgtgg tggtggtgg                                            29

<210> SEQ ID NO 9
<211> LENGTH: 29
<212> TYPE: DNA
<213> ORGANISM: Artificial Sequence
<220> FEATURE:
<223> OTHER INFORMATION: aptamer 1642-13 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 12
<223> OTHER INFORMATION: n is BzdU

<400> SEQUENCE: 9
tttggtggtg gnggttgtgg tggtggtgg                                            29

<210> SEQ ID NO 10
<211> LENGTH: 29
<212> TYPE: DNA
<213> ORGANISM: Artificial Sequence
<220> FEATURE:
<223> OTHER INFORMATION: aptamer 1642-14 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 15
<223> OTHER INFORMATION: n is BzdU

<400> SEQUENCE: 10
tttggtggtg gtggntgtgg tggtggtgg                                            29

<210> SEQ ID NO 11
<211> LENGTH: 29
<212> TYPE: DNA
```

```
<213> ORGANISM: Artificial Sequence
<220> FEATURE:
<223> OTHER INFORMATION: aptamer 1642-15 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 16
<223> OTHER INFORMATION: n is BzdU

<400> SEQUENCE: 11
tttggtggtg gtggtngtgg tggtggtgg                                           29

<210> SEQ ID NO 12
<211> LENGTH: 29
<212> TYPE: DNA
<213> ORGANISM: Artificial Sequence
<220> FEATURE:
<223> OTHER INFORMATION: aptamer 1642-16 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 18
<223> OTHER INFORMATION: n is BzdU

<400> SEQUENCE: 12
tttggtggtg gtggttgngg tggtggtgg                                           29

<210> SEQ ID NO 13
<211> LENGTH: 29
<212> TYPE: DNA
<213> ORGANISM: Artificial Sequence
<220> FEATURE:
<223> OTHER INFORMATION: aptamer 1642-17 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 21
<223> OTHER INFORMATION: n is BzdU

<400> SEQUENCE: 13
tttggtggtg gtggttgtgg nggtggtgg                                           29

<210> SEQ ID NO 14
<211> LENGTH: 29
<212> TYPE: DNA
<213> ORGANISM: Artificial Sequence
<220> FEATURE:
<223> OTHER INFORMATION: aptamer 1642-18 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 24
<223> OTHER INFORMATION: n is BzdU

<400> SEQUENCE: 14
tttggtggtg gtggttgtgg tggnggtgg                                           29

<210> SEQ ID NO 15
<211> LENGTH: 29
<212> TYPE: DNA
<213> ORGANISM: Artificial Sequence
<220> FEATURE:
<223> OTHER INFORMATION: aptamer 1642-19 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 27
```

<223> OTHER INFORMATION: n is BzdU

<400> SEQUENCE: 15
tttggtggtg gtggttgtgg tggtggngg                                29

<210> SEQ ID NO 16
<211> LENGTH: 29
<212> TYPE: DNA
<213> ORGANISM: Artificial Sequence
<220> FEATURE:
<223> OTHER INFORMATION: aptamer 1642-21 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 2..3
<223> OTHER INFORMATION: n is BzdU

<400> SEQUENCE: 16
tnnggtggtg gtggttgtgg tggtggtgg                                29

<210> SEQ ID NO 17
<211> LENGTH: 29
<212> TYPE: DNA
<213> ORGANISM: Artificial Sequence
<220> FEATURE:
<223> OTHER INFORMATION: aptamer 1642-23 which is modified GRO29A
      containing Bz at 5 position of dU (5-(N-benzylcarboxyamide)-2'-
      deoxyuridine, BzdU),
<220> FEATURE:
<221> NAME/KEY: misc_feature
<222> LOCATION: 1..3
<223> OTHER INFORMATION: n is BzdU

<400> SEQUENCE: 17
nnnggtggtg gtggttgtgg tggtggtgg                                29

<210> SEQ ID NO 18
<211> LENGTH: 29
<212> TYPE: DNA
<213> ORGANISM: Artificial Sequence
<220> FEATURE:
<223> OTHER INFORMATION: aptamer 1642-24 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 24; 27
<223> OTHER INFORMATION: n is BzdU

<400> SEQUENCE: 18
tttggtggtg gtggttgtgg tggnggngg                                29

<210> SEQ ID NO 19
<211> LENGTH: 29
<212> TYPE: DNA
<213> ORGANISM: Artificial Sequence
<220> FEATURE:
<223> OTHER INFORMATION: aptamer 1642-25 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 21; 27
<223> OTHER INFORMATION: n is BzdU

<400> SEQUENCE: 19
tttggtggtg gtggttgtgg nggtggngg                                29

<210> SEQ ID NO 20

```
<211> LENGTH: 29
<212> TYPE: DNA
<213> ORGANISM: Artificial Sequence
<220> FEATURE:
<223> OTHER INFORMATION: aptamer 1642-26 which is modified GRO29A
      containing Bz at 5 position of dU (5-(N-benzylcarboxyamide)-2'-
      deoxyuridine, BzdU),
<220> FEATURE:
<221> NAME/KEY: misc_feature
<222> LOCATION: 18; 27
<223> OTHER INFORMATION: n is BzdU

<400> SEQUENCE: 20
tttggtggtg gtggttgngg tggtggngg                                    29

<210> SEQ ID NO 21
<211> LENGTH: 29
<212> TYPE: DNA
<213> ORGANISM: Artificial Sequence
<220> FEATURE:
<223> OTHER INFORMATION: aptamer 1642-27 which is modified GRO29A
      containing Bz at 5 position of dU (5-(N-benzylcarboxyamide)-2'-
      deoxyuridine, BzdU),
<220> FEATURE:
<221> NAME/KEY: misc_feature
<222> LOCATION: 16; 27
<223> OTHER INFORMATION: n is BzdU

<400> SEQUENCE: 21
tttggtggtg gtggtngtgg tggtggngg                                    29

<210> SEQ ID NO 22
<211> LENGTH: 29
<212> TYPE: DNA
<213> ORGANISM: Artificial Sequence
<220> FEATURE:
<223> OTHER INFORMATION: aptamer 1642-28 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 15; 27
<223> OTHER INFORMATION: n is BzdU

<400> SEQUENCE: 22
tttggtggtg gtggntgtgg tggtggngg                                    29

<210> SEQ ID NO 23
<211> LENGTH: 29
<212> TYPE: DNA
<213> ORGANISM: Artificial Sequence
<220> FEATURE:
<223> OTHER INFORMATION: aptamer 1642-29 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 12; 27
<223> OTHER INFORMATION: n is BzdU

<400> SEQUENCE: 23
tttggtggtg gnggttgtgg tggtggngg                                    29

<210> SEQ ID NO 24
<211> LENGTH: 29
<212> TYPE: DNA
<213> ORGANISM: Artificial Sequence
<220> FEATURE:
<223> OTHER INFORMATION: aptamer 1642-30 which is modified GRO29A
      containing Bz at 5 position of dU (5-(N-benzylcarboxyamide)-2'-
      deoxyuridine, BzdU)
<220> FEATURE:
```

```
<221> NAME/KEY: misc_feature
<222> LOCATION: 9; 27
<223> OTHER INFORMATION: n is BzdU

<400> SEQUENCE: 24
tttggtggng gtggttgtgg tggtggngg                                        29

<210> SEQ ID NO 25
<211> LENGTH: 29
<212> TYPE: DNA
<213> ORGANISM: Artificial Sequence
<220> FEATURE:
<223> OTHER INFORMATION: aptamer 1642-31 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 6; 27
<223> OTHER INFORMATION: n is BzdU

<400> SEQUENCE: 25
tttggnggtg gtggttgtgg tggtggngg                                        29

<210> SEQ ID NO 26
<211> LENGTH: 29
<212> TYPE: DNA
<213> ORGANISM: Artificial Sequence
<220> FEATURE:
<223> OTHER INFORMATION: aptamer 1642-32 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 3; 27
<223> OTHER INFORMATION: n is BzdU

<400> SEQUENCE: 26
ttnggtggtg gtggttgtgg tggtggngg                                        29

<210> SEQ ID NO 27
<211> LENGTH: 29
<212> TYPE: DNA
<213> ORGANISM: Artificial Sequence
<220> FEATURE:
<223> OTHER INFORMATION: aptamer 1642-33 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 2; 27
<223> OTHER INFORMATION: n is BzdU

<400> SEQUENCE: 27
tntggtggtg gtggttgtgg tggtggngg                                        29

<210> SEQ ID NO 28
<211> LENGTH: 29
<212> TYPE: DNA
<213> ORGANISM: Artificial Sequence
<220> FEATURE:
<223> OTHER INFORMATION: aptamer 1642-34 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 1; 27
<223> OTHER INFORMATION: n is BzdU

<400> SEQUENCE: 28
nttggtggtg gtggttgtgg tggtggngg                                        29
```

```
<210> SEQ ID NO 29
<211> LENGTH: 29
<212> TYPE: DNA
<213> ORGANISM: Artificial Sequence
<220> FEATURE:
<223> OTHER INFORMATION: aptamer 1642-35 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 15..16; 27
<223> OTHER INFORMATION: n is BzdU

<400> SEQUENCE: 29
tttggtggtg gtggnngtgg tggtggngg                                       29

<210> SEQ ID NO 30
<211> LENGTH: 29
<212> TYPE: DNA
<213> ORGANISM: Artificial Sequence
<220> FEATURE:
<223> OTHER INFORMATION: aptamer 1642-36 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 2..3; 27
<223> OTHER INFORMATION: n is BzdU

<400> SEQUENCE: 30
tnnggtggtg gtggttgtgg tggtggngg                                       29

<210> SEQ ID NO 31
<211> LENGTH: 29
<212> TYPE: DNA
<213> ORGANISM: Artificial Sequence
<220> FEATURE:
<223> OTHER INFORMATION: aptamer 1642-37 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 1..2; 27
<223> OTHER INFORMATION: n is BzdU

<400> SEQUENCE: 31
nntggtggtg gtggttgtgg tggtggngg                                       29

<210> SEQ ID NO 32
<211> LENGTH: 29
<212> TYPE: DNA
<213> ORGANISM: Artificial Sequence
<220> FEATURE:
<223> OTHER INFORMATION: aptamer 1642-39 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 15..16
<223> OTHER INFORMATION: n is BzdU

<400> SEQUENCE: 32
tttggtggtg gtggnngtgg tggtggtgg                                       29

<210> SEQ ID NO 33
<211> LENGTH: 29
<212> TYPE: DNA
<213> ORGANISM: Artificial Sequence
<220> FEATURE:
<223> OTHER INFORMATION: aptamer 1642-40 which is modified GRO29A
      containing Bz at 5 position of dU (5-(N-benzylcarboxyamide)-2'-
```

```
        deoxyuridine, BzdU)
<220> FEATURE:
<221> NAME/KEY: misc_feature
<222> LOCATION: 15..16; 18
<223> OTHER INFORMATION: n is BzdU

<400> SEQUENCE: 33
tttggtggtg gtggnngngg tggtggtgg                                              29

<210> SEQ ID NO 34
<211> LENGTH: 29
<212> TYPE: DNA
<213> ORGANISM: Artificial Sequence
<220> FEATURE:
<223> OTHER INFORMATION: aptamer 1642-41 which is modified GRO29A
        containing Bz at 5 position of dU (5-(N-benzylcarboxyamide)-2'-
        deoxyuridine, BzdU)
<220> FEATURE:
<221> NAME/KEY: misc_feature
<222> LOCATION: 15..16; 21
<223> OTHER INFORMATION: n is BzdU

<400> SEQUENCE: 34
tttggtggtg gtggnngtgg nggtggtgg                                              29

<210> SEQ ID NO 35
<211> LENGTH: 29
<212> TYPE: DNA
<213> ORGANISM: Artificial Sequence
<220> FEATURE:
<223> OTHER INFORMATION: aptamer 1642-42 which is modified GRO29A
        containing Bz at 5 position of dU (5-(N-benzylcarboxyamide)-2'-
        deoxyuridine, BzdU)
<220> FEATURE:
<221> NAME/KEY: misc_feature
<222> LOCATION: 15..16; 24
<223> OTHER INFORMATION: n is BzdU

<400> SEQUENCE: 35
tttggtggtg gtggnngtgg tggnggtgg                                              29

<210> SEQ ID NO 36
<211> LENGTH: 29
<212> TYPE: DNA
<213> ORGANISM: Artificial Sequence
<220> FEATURE:
<223> OTHER INFORMATION: aptamer 1642-43 which is modified GRO29A
        containing Bz at 5 position of dU (5-(N-benzylcarboxyamide)-2'-
        deoxyuridine, BzdU)
<220> FEATURE:
<221> NAME/KEY: misc_feature
<222> LOCATION: 12; 15..16
<223> OTHER INFORMATION: n is BzdU

<400> SEQUENCE: 36
tttggtggtg gnggnngtgg tggtggtgg                                              29

<210> SEQ ID NO 37
<211> LENGTH: 29
<212> TYPE: DNA
<213> ORGANISM: Artificial Sequence
<220> FEATURE:
<223> OTHER INFORMATION: aptamer 1642-44 which is modified GRO29A
        containing Bz at 5 position of dU (5-(N-benzylcarboxyamide)-2'-
        deoxyuridine, BzdU)
<220> FEATURE:
<221> NAME/KEY: misc_feature
<222> LOCATION: 9; 15..16
<223> OTHER INFORMATION: n is BzdU

<400> SEQUENCE: 37
```

```
tttggtgggng gtggnngtgg tggtggtgg                                              29

<210> SEQ ID NO 38
<211> LENGTH: 29
<212> TYPE: DNA
<213> ORGANISM: Artificial Sequence
<220> FEATURE:
<223> OTHER INFORMATION: aptamer 1642-45 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 6; 15..16
<223> OTHER INFORMATION: n is BzdU

<400> SEQUENCE: 38
tttggnggtg gtggnngtgg tggtggtgg                                               29

<210> SEQ ID NO 39
<211> LENGTH: 29
<212> TYPE: DNA
<213> ORGANISM: Artificial Sequence
<220> FEATURE:
<223> OTHER INFORMATION: aptamer 1642-46 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 3; 15..16
<223> OTHER INFORMATION: n is BzdU

<400> SEQUENCE: 39
ttnggtggtg gtggnngtgg tggtggtgg                                               29

<210> SEQ ID NO 40
<211> LENGTH: 29
<212> TYPE: DNA
<213> ORGANISM: Artificial Sequence
<220> FEATURE:
<223> OTHER INFORMATION: aptamer 1642-47 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 2; 15..16
<223> OTHER INFORMATION: n is BzdU

<400> SEQUENCE: 40
tntggtggtg gtggnngtgg tggtggtgg                                               29

<210> SEQ ID NO 41
<211> LENGTH: 29
<212> TYPE: DNA
<213> ORGANISM: Artificial Sequence
<220> FEATURE:
<223> OTHER INFORMATION: aptamer 1642-48 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 1; 15..16
<223> OTHER INFORMATION: n is BzdU

<400> SEQUENCE: 41
nttggtggtg gtggnngtgg tggtggtgg                                               29

<210> SEQ ID NO 42
<211> LENGTH: 29
<212> TYPE: DNA
<213> ORGANISM: Artificial Sequence
<220> FEATURE:
```

<223> OTHER INFORMATION: aptamer 1642-49 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 2..3; 15..16
<223> OTHER INFORMATION: n is BzdU

<400> SEQUENCE: 42
tnnggtggtg gtggnngtgg tggtggtgg                                              29

<210> SEQ ID NO 43
<211> LENGTH: 29
<212> TYPE: DNA
<213> ORGANISM: Artificial Sequence
<220> FEATURE:
<223> OTHER INFORMATION: aptamer 1642-50 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 1..2; 15..16
<223> OTHER INFORMATION: n is BzdU

<400> SEQUENCE: 43
nntggtggtg gtggnngtgg tggtggtgg                                              29

<210> SEQ ID NO 44
<211> LENGTH: 29
<212> TYPE: DNA
<213> ORGANISM: Artificial Sequence
<220> FEATURE:
<223> OTHER INFORMATION: aptamer 1642-51 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 1; 3; 15..16
<223> OTHER INFORMATION: n is BzdU

<400> SEQUENCE: 44
ntnggtggtg gtggnngtgg tggtggtgg                                              29

<210> SEQ ID NO 45
<211> LENGTH: 29
<212> TYPE: DNA
<213> ORGANISM: Artificial Sequence
<220> FEATURE:
<223> OTHER INFORMATION: aptamer 1642-52 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 1..3; 15..16
<223> OTHER INFORMATION: n is BzdU

<400> SEQUENCE: 45
nnnggtggtg gtggnngtgg tggtggtgg                                              29

<210> SEQ ID NO 46
<211> LENGTH: 29
<212> TYPE: DNA
<213> ORGANISM: Artificial Sequence
<220> FEATURE:
<223> OTHER INFORMATION: aptamer 1642-53 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 12; 18
<223> OTHER INFORMATION: n is BzdU

```
<400> SEQUENCE: 46
tttggtggtg gnggttgngg tggtggtgg                                              29

<210> SEQ ID NO 47
<211> LENGTH: 29
<212> TYPE: DNA
<213> ORGANISM: Artificial Sequence
<220> FEATURE:
<223> OTHER INFORMATION: aptamer 1642-54 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 9; 21
<223> OTHER INFORMATION: n is BzdU

<400> SEQUENCE: 47
tttggtggng gtggttgtgg nggtggtgg                                              29

<210> SEQ ID NO 48
<211> LENGTH: 29
<212> TYPE: DNA
<213> ORGANISM: Artificial Sequence
<220> FEATURE:
<223> OTHER INFORMATION: aptamer 1642-55 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 6; 24
<223> OTHER INFORMATION: n is BzdU

<400> SEQUENCE: 48
tttggnggtg gtggttgtgg tggnggtgg                                              29

<210> SEQ ID NO 49
<211> LENGTH: 29
<212> TYPE: DNA
<213> ORGANISM: Artificial Sequence
<220> FEATURE:
<223> OTHER INFORMATION: aptamer 1642-56 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 9; 12; 18; 21; 24
<223> OTHER INFORMATION: n is BzdU

<400> SEQUENCE: 49
tttggtggng gnggttgngg nggnggtgg                                              29

<210> SEQ ID NO 50
<211> LENGTH: 29
<212> TYPE: DNA
<213> ORGANISM: Artificial Sequence
<220> FEATURE:
<223> OTHER INFORMATION: aptamer 1642-57 which is modified GRO29A
      containing Bz at 5 position of dU (5-(N-benzylcarboxyamide)-2'-
      deoxyuridine, BzdU)
<220> FEATURE:
<221> NAME/KEY: misc_feature
<222> LOCATION: 6; 9; 12; 18; 21; 27
<223> OTHER INFORMATION: n is BzdU

<400> SEQUENCE: 50
tttggnggng gnggttgngg nggtggngg                                              29

<210> SEQ ID NO 51
<211> LENGTH: 29
<212> TYPE: DNA
```

```
<213> ORGANISM: Artificial Sequence
<220> FEATURE:
<223> OTHER INFORMATION: aptamer CRO29A

<400> SEQUENCE: 51
tttcctcctc ctccttctcc tcctcctcc                                              29

<210> SEQ ID NO 52
<211> LENGTH: 26
<212> TYPE: DNA
<213> ORGANISM: Artificial Sequence
<220> FEATURE:
<223> OTHER INFORMATION: Aptamer 1641-8(Control AS1411)

<400> SEQUENCE: 52
cctcctcctc cttctcctcc tcctcc                                                 26

<210> SEQ ID NO 53
<211> LENGTH: 29
<212> TYPE: DNA
<213> ORGANISM: Artificial Sequence
<220> FEATURE:
<223> OTHER INFORMATION: aptamer 1642-59 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 6
<223> OTHER INFORMATION: n is NapdU

<400> SEQUENCE: 53
tttggnggtg gtggttgtgg tggtggtgg                                              29

<210> SEQ ID NO 54
<211> LENGTH: 29
<212> TYPE: DNA
<213> ORGANISM: Artificial Sequence
<220> FEATURE:
<223> OTHER INFORMATION: aptamer 1642-60 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 9
<223> OTHER INFORMATION: n is NapdU

<400> SEQUENCE: 54
tttggtggng gtggttgtgg tggtggtgg                                              29

<210> SEQ ID NO 55
<211> LENGTH: 29
<212> TYPE: DNA
<213> ORGANISM: Artificial Sequence
<220> FEATURE:
<223> OTHER INFORMATION: aptamer 1642-61 which is modified GRO29A
      containing Nap position of dU (5-(N-naphthylcarboxyamide)-2'-
      deoxyuridine NapdU)
<220> FEATURE:
<221> NAME/KEY: misc_feature
<222> LOCATION: 12
<223> OTHER INFORMATION: n is NapdU

<400> SEQUENCE: 55
tttggtggtg gnggttgtgg tggtggtgg                                              29

<210> SEQ ID NO 56
<211> LENGTH: 29
<212> TYPE: DNA
<213> ORGANISM: Artificial Sequence
<220> FEATURE:
```

<223> OTHER INFORMATION: aptamer 1642-62 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 27
<223> OTHER INFORMATION: n is NapdU

<400> SEQUENCE: 56
tttggtggtg gtggttgtgg tggtggngg                                    29

<210> SEQ ID NO 57
<211> LENGTH: 29
<212> TYPE: DNA
<213> ORGANISM: Artificial Sequence
<220> FEATURE:
<223> OTHER INFORMATION: aptamer 1642-63 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 9; 27
<223> OTHER INFORMATION: n is NapdU

<400> SEQUENCE: 57
tttggtggng gtggttgtgg tggtggngg                                    29

<210> SEQ ID NO 58
<211> LENGTH: 29
<212> TYPE: DNA
<213> ORGANISM: Artificial Sequence
<220> FEATURE:
<223> OTHER INFORMATION: aptamer 1642-64 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 6; 27
<223> OTHER INFORMATION: n is NapdU

<400> SEQUENCE: 58
tttggnggtg gtggttgtgg tggtggngg                                    29

<210> SEQ ID NO 59
<211> LENGTH: 29
<212> TYPE: DNA
<213> ORGANISM: Artificial Sequence
<220> FEATURE:
<223> OTHER INFORMATION: aptamer 1642-65 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 1..2; 27
<223> OTHER INFORMATION: n is NapdU

<400> SEQUENCE: 59
nntggtggtg gtggttgtgg tggtggngg                                    29

<210> SEQ ID NO 60
<211> LENGTH: 29
<212> TYPE: DNA
<213> ORGANISM: Artificial Sequence
<220> FEATURE:
<223> OTHER INFORMATION: aptamer 1642-66 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 15..16
<223> OTHER INFORMATION: n is NapdU

```
<400> SEQUENCE: 60
tttggtggtg gtggnngtgg tggtggtgg                                    29

<210> SEQ ID NO 61
<211> LENGTH: 29
<212> TYPE: DNA
<213> ORGANISM: Artificial Sequence
<220> FEATURE:
<223> OTHER INFORMATION: aptamer 1642-68 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 15..16; 18
<223> OTHER INFORMATION: n is NapdU

<400> SEQUENCE: 61
tttggtggtg gtggnngngg tggtggtgg                                    29

<210> SEQ ID NO 62
<211> LENGTH: 29
<212> TYPE: DNA
<213> ORGANISM: Artificial Sequence
<220> FEATURE:
<223> OTHER INFORMATION: aptamer 1642-67 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 15..16; 21
<223> OTHER INFORMATION: n is NapdU

<400> SEQUENCE: 62
tttggtggtg gtggnngtgg nggtggtgg                                    29

<210> SEQ ID NO 63
<211> LENGTH: 29
<212> TYPE: DNA
<213> ORGANISM: Artificial Sequence
<220> FEATURE:
<223> OTHER INFORMATION: aptamer 1642-69 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 2; 15..16
<223> OTHER INFORMATION: n is NapdU

<400> SEQUENCE: 63
tntggtggtg gtggnngtgg tggtggtgg                                    29

<210> SEQ ID NO 64
<211> LENGTH: 29
<212> TYPE: DNA
<213> ORGANISM: Artificial Sequence
<220> FEATURE:
<223> OTHER INFORMATION: aptamer 1642-70 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 1; 15..16
<223> OTHER INFORMATION: n is NapdU

<400> SEQUENCE: 64
nttggtggtg gtggnngtgg tggtggtgg                                    29

<210> SEQ ID NO 65
<211> LENGTH: 29
<212> TYPE: DNA
```

```
<213> ORGANISM: Artificial Sequence
<220> FEATURE:
<223> OTHER INFORMATION: aptamer 1642-71 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 2..3; 15..16
<223> OTHER INFORMATION: n is NapdU

<400> SEQUENCE: 65
tnnggtggtg gtggnngtgg tggtggtgg                                            29

<210> SEQ ID NO 66
<211> LENGTH: 29
<212> TYPE: DNA
<213> ORGANISM: Artificial Sequence
<220> FEATURE:
<223> OTHER INFORMATION: aptamer 1642-72 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 1; 3; 15..16
<223> OTHER INFORMATION: n is NapdU

<400> SEQUENCE: 66
ntnggtggtg gtggnngtgg tggtggtgg                                            29

<210> SEQ ID NO 67
<211> LENGTH: 29
<212> TYPE: DNA
<213> ORGANISM: Artificial Sequence
<220> FEATURE:
<223> OTHER INFORMATION: aptamer 1642-73 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 1..3; 15..16
<223> OTHER INFORMATION: n is NapdU

<400> SEQUENCE: 67
nnnggtggtg gtggnngtgg tggtggtgg                                            29

<210> SEQ ID NO 68
<211> LENGTH: 29
<212> TYPE: DNA
<213> ORGANISM: Artificial Sequence
<220> FEATURE:
<223> OTHER INFORMATION: aptamer 1642-74 which is modified GRO29A
      containing Nap at 5 position of dU (5-(N-naphthylcarboxyamide)-2'-
      deoxyuridine, NapdU)
<220> FEATURE:
<221> NAME/KEY: misc_feature
<222> LOCATION: 6; 9; 12; 18; 21; 27
<223> OTHER INFORMATION: n is NapdU

<400> SEQUENCE: 68
tttggnggng gnggttgngg nggtggngg                                            29

<210> SEQ ID NO 69
<211> LENGTH: 26
<212> TYPE: DNA
<213> ORGANISM: Artificial Sequence
<220> FEATURE:
<223> OTHER INFORMATION: aptamer 1642-88 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 3; 6; 9; 12..13; 15; 18; 21; 24
```

-continued

<223> OTHER INFORMATION: n is BzdU

<400> SEQUENCE: 69
ggnggnggng gnngnggngg nggngg        26

<210> SEQ ID NO 70
<211> LENGTH: 26
<212> TYPE: DNA
<213> ORGANISM: Artificial Sequence
<220> FEATURE:
<223> OTHER INFORMATION: aptamer 1642-89 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 3; 6; 9; 18; 21; 24
<223> OTHER INFORMATION: n is BzdU

<400> SEQUENCE: 70
ggnggnggng gttgtggngg nggngg        26

<210> SEQ ID NO 71
<211> LENGTH: 26
<212> TYPE: DNA
<213> ORGANISM: Artificial Sequence
<220> FEATURE:
<223> OTHER INFORMATION: aptamer 1642-90 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 3; 6; 21; 24
<223> OTHER INFORMATION: n is BzdU

<400> SEQUENCE: 71
ggnggnggtg gttgtggtgg nggngg        26

<210> SEQ ID NO 72
<211> LENGTH: 26
<212> TYPE: DNA
<213> ORGANISM: Artificial Sequence
<220> FEATURE:
<223> OTHER INFORMATION: aptamer 1642-91 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 6; 9; 18; 21
<223> OTHER INFORMATION: n is BzdU

<400> SEQUENCE: 72
ggtggnggng gttgtggngg nggtgg        26

<210> SEQ ID NO 73
<211> LENGTH: 26
<212> TYPE: DNA
<213> ORGANISM: Artificial Sequence
<220> FEATURE:
<223> OTHER INFORMATION: aptamer 1642-92 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 3; 24
<223> OTHER INFORMATION: n is BzdU

<400> SEQUENCE: 73
ggnggtggtg gttgtggtgg tggngg        26

<210> SEQ ID NO 74

```
<211> LENGTH: 26
<212> TYPE: DNA
<213> ORGANISM: Artificial Sequence
<220> FEATURE:
<223> OTHER INFORMATION: aptamer 1642-93 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 6; 21
<223> OTHER INFORMATION: n is BzdU

<400> SEQUENCE: 74
ggtggnggtg gttgtggtgg nggtgg                                            26

<210> SEQ ID NO 75
<211> LENGTH: 26
<212> TYPE: DNA
<213> ORGANISM: Artificial Sequence
<220> FEATURE:
<223> OTHER INFORMATION: aptamer 1642-94 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 9; 18
<223> OTHER INFORMATION: n is BzdU

<400> SEQUENCE: 75
ggtggtggng gttgtggngg tggtgg                                            26

<210> SEQ ID NO 76
<211> LENGTH: 26
<212> TYPE: DNA
<213> ORGANISM: Artificial Sequence
<220> FEATURE:
<223> OTHER INFORMATION: aptamer 1642-95 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 3; 9; 18; 24
<223> OTHER INFORMATION: n is BzdU

<400> SEQUENCE: 76
ggnggtggng gttgtggngg tggngg                                            26

<210> SEQ ID NO 77
<211> LENGTH: 26
<212> TYPE: DNA
<213> ORGANISM: Artificial Sequence
<220> FEATURE:
<223> OTHER INFORMATION: aptamer 1642-96 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 13
<223> OTHER INFORMATION: n is BzdU

<400> SEQUENCE: 77
ggtggtggtg gtngtggtgg tggtgg                                            26

<210> SEQ ID NO 78
<211> LENGTH: 26
<212> TYPE: DNA
<213> ORGANISM: Artificial Sequence
<220> FEATURE:
<223> OTHER INFORMATION: aptamer 1642-97 which is modified AS1411 having
      hydrophobic groups such as BN at 5 position of dU
      (5-(N-benzylcarboxyamide)-2'-deoxyuridine, BzdU)
<220> FEATURE:
```

```
<221> NAME/KEY: misc_feature
<222> LOCATION: 12..13; 15
<223> OTHER INFORMATION: n is BzdU

<400> SEQUENCE: 78
ggtggtggtg gnngnggtgg tggtgg                                           26

<210> SEQ ID NO 79
<211> LENGTH: 26
<212> TYPE: DNA
<213> ORGANISM: Artificial Sequence
<220> FEATURE:
<223> OTHER INFORMATION: aptamer 1642-98 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 12; 15;
<223> OTHER INFORMATION: n is BzdU

<400> SEQUENCE: 79
ggtggtggtg gntgnggtgg tggtgg                                           26

<210> SEQ ID NO 80
<211> LENGTH: 26
<212> TYPE: DNA
<213> ORGANISM: Artificial Sequence
<220> FEATURE:
<223> OTHER INFORMATION: aptamer 1642-82 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 3
<223> OTHER INFORMATION: n is BzdU

<400> SEQUENCE: 80
ggnggtggtg gttgtggtgg tggtgg                                           26

<210> SEQ ID NO 81
<211> LENGTH: 26
<212> TYPE: DNA
<213> ORGANISM: Artificial Sequence
<220> FEATURE:
<223> OTHER INFORMATION: aptamer 1642-99 which is modified AS1411 having
      hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 6
<223> OTHER INFORMATION: n is BzdU

<400> SEQUENCE: 81
ggtggnggtg gttgtggtgg tggtgg                                           26

<210> SEQ ID NO 82
<211> LENGTH: 26
<212> TYPE: DNA
<213> ORGANISM: Artificial Sequence
<220> FEATURE:
<223> OTHER INFORMATION: aptamer 1642-100 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 9
<223> OTHER INFORMATION: n is BzdU

<400> SEQUENCE: 82
ggtggtggng gttgtggtgg tggtgg                                           26
```

<210> SEQ ID NO 83
<211> LENGTH: 26
<212> TYPE: DNA
<213> ORGANISM: Artificial Sequence
<220> FEATURE:
<223> OTHER INFORMATION: aptamer 1642-101 which is modified AS1411
having hydrophobic groups such as BN at 5 position of dU
(5-(N-benzylcarboxyamide)-2'-deoxyuridine, BzdU)
<220> FEATURE:
<221> NAME/KEY: misc_feature
<222> LOCATION: 12
<223> OTHER INFORMATION: n is BzdU

<400> SEQUENCE: 83
ggtggtggtg gntgtggtgg tggtgg                                    26

<210> SEQ ID NO 84
<211> LENGTH: 26
<212> TYPE: DNA
<213> ORGANISM: Artificial Sequence
<220> FEATURE:
<223> OTHER INFORMATION: aptamer 1642-102 which is modified AS1411
having hydrophobic groups such as BN at 5 position of dU
(5-(N-benzylcarboxyamide)-2'-deoxyuridine, BzdU)
<220> FEATURE:
<221> NAME/KEY: misc_feature
<222> LOCATION: 13
<223> OTHER INFORMATION: n is BzdU

<400> SEQUENCE: 84
ggtggtggtg gtngtggtgg tggtgg                                    26

<210> SEQ ID NO 85
<211> LENGTH: 26
<212> TYPE: DNA
<213> ORGANISM: Artificial Sequence
<220> FEATURE:
<223> OTHER INFORMATION: aptamer 1642-103 which is modified AS1411
having hydrophobic groups such as BN at 5 position of dU
(5-(N-benzylcarboxyamide)-2'-deoxyuridine, BzdU)
<220> FEATURE:
<221> NAME/KEY: misc_feature
<222> LOCATION: 15
<223> OTHER INFORMATION: n is BzdU

<400> SEQUENCE: 85
ggtggtggtg gttgnggtgg tggtgg                                    26

<210> SEQ ID NO 86
<211> LENGTH: 26
<212> TYPE: DNA
<213> ORGANISM: Artificial Sequence
<220> FEATURE:
<223> OTHER INFORMATION: aptamer 1642-104 which is modified AS1411
having hydrophobic groups such as BN at 5 position of dU
(5-(N-benzylcarboxyamide)-2'-deoxyuridine, BzdU)
<220> FEATURE:
<221> NAME/KEY: misc_feature
<222> LOCATION: 18
<223> OTHER INFORMATION: n is BzdU

<400> SEQUENCE: 86
ggtggtggtg gttgtggngg tggtgg                                    26

<210> SEQ ID NO 87
<211> LENGTH: 26
<212> TYPE: DNA
<213> ORGANISM: Artificial Sequence
<220> FEATURE:
<223> OTHER INFORMATION: aptamer 1642-105 which is modified AS1411
having hydrophobic groups such as BN at 5 position of dU

```
           (5-(N-benzylcarboxyamide)-2'-deoxyuridine, BzdU)
<220> FEATURE:
<221> NAME/KEY: misc_feature
<222> LOCATION: 21
<223> OTHER INFORMATION: n is BzdU

<400> SEQUENCE: 87
ggtggtggtg gttgtggtgg nggtgg                                         26

<210> SEQ ID NO 88
<211> LENGTH: 26
<212> TYPE: DNA
<213> ORGANISM: Artificial Sequence
<220> FEATURE:
<223> OTHER INFORMATION: aptamer 1642-83 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 24
<223> OTHER INFORMATION: n is BzdU

<400> SEQUENCE: 88
ggtggtggtg gttgtggtgg tggngg                                         26

<210> SEQ ID NO 89
<211> LENGTH: 26
<212> TYPE: DNA
<213> ORGANISM: Artificial Sequence
<220> FEATURE:
<223> OTHER INFORMATION: aptamer 1642-106 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 21; 24
<223> OTHER INFORMATION: n is BzdU

<400> SEQUENCE: 89
ggtggtggtg gttgtggtgg nggngg                                         26

<210> SEQ ID NO 90
<211> LENGTH: 26
<212> TYPE: DNA
<213> ORGANISM: Artificial Sequence
<220> FEATURE:
<223> OTHER INFORMATION: aptamer 1642-107 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 18; 24
<223> OTHER INFORMATION: n is BzdU

<400> SEQUENCE: 90
ggtggtggtg gttgtggngg tggngg                                         26

<210> SEQ ID NO 91
<211> LENGTH: 26
<212> TYPE: DNA
<213> ORGANISM: Artificial Sequence
<220> FEATURE:
<223> OTHER INFORMATION: aptamer 1642-108 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 15; 24
<223> OTHER INFORMATION: n is BzdU

<400> SEQUENCE: 91
```
ggtggtggtg gttgnggtgg tggngg                                   26

<210> SEQ ID NO 92
<211> LENGTH: 26
<212> TYPE: DNA
<213> ORGANISM: Artificial Sequence
<220> FEATURE:
<223> OTHER INFORMATION: aptamer 1642-109 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 13; 24
<223> OTHER INFORMATION: n is BzdU

<400> SEQUENCE: 92
ggtggtggtg gtngtggtgg tggngg                                   26

<210> SEQ ID NO 93
<211> LENGTH: 26
<212> TYPE: DNA
<213> ORGANISM: Artificial Sequence
<220> FEATURE:
<223> OTHER INFORMATION: aptamer 1642-110 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 12; 24
<223> OTHER INFORMATION: n is BzdU

<400> SEQUENCE: 93
ggtggtggtg gntgtggtgg tggngg                                   26

<210> SEQ ID NO 94
<211> LENGTH: 26
<212> TYPE: DNA
<213> ORGANISM: Artificial Sequence
<220> FEATURE:
<223> OTHER INFORMATION: aptamer 1642-111 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 9; 24
<223> OTHER INFORMATION: n is BzdU

<400> SEQUENCE: 94
ggtggtggng gttgtggtgg tggngg                                   26

<210> SEQ ID NO 95
<211> LENGTH: 26
<212> TYPE: DNA
<213> ORGANISM: Artificial Sequence
<220> FEATURE:
<223> OTHER INFORMATION: aptamer 1642-112 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 6; 24
<223> OTHER INFORMATION: n is BzdU

<400> SEQUENCE: 95
ggtggnggtg gttgtggtgg tggngg                                   26

<210> SEQ ID NO 96
<211> LENGTH: 26
<212> TYPE: DNA
<213> ORGANISM: Artificial Sequence
<220> FEATURE:

-continued

<223> OTHER INFORMATION: aptamer 1642-113 which is modified AS1411
     having hydrophobic groups such as BN at 5 position of dU
     (5-(N-benzylcarboxyamide)-2'-deoxyuridine, BzdU)
<220> FEATURE:
<221> NAME/KEY: misc_feature
<222> LOCATION: 3; 24
<223> OTHER INFORMATION: n is BzdU

<400> SEQUENCE: 96
ggnggtggtg gttgtggtgg tggngg                                         26

<210> SEQ ID NO 97
<211> LENGTH: 26
<212> TYPE: DNA
<213> ORGANISM: Artificial Sequence
<220> FEATURE:
<223> OTHER INFORMATION: aptamer 1642-114 which is modified AS1411
     having hydrophobic groups such as BN at 5 position of dU
     (5-(N-benzylcarboxyamide)-2'-deoxyuridine, BzdU)
<220> FEATURE:
<221> NAME/KEY: misc_feature
<222> LOCATION: 12..13; 24
<223> OTHER INFORMATION: n is BzdU

<400> SEQUENCE: 97
ggtggtggtg gnngtggtgg tggngg                                         26

<210> SEQ ID NO 98
<211> LENGTH: 26
<212> TYPE: DNA
<213> ORGANISM: Artificial Sequence
<220> FEATURE:
<223> OTHER INFORMATION: aptamer 1642-115 which is modified AS1411
     having hydrophobic groups such as BN at 5 position of dU
     (5-(N-benzylcarboxyamide)-2'-deoxyuridine, BzdU)
<220> FEATURE:
<221> NAME/KEY: misc_feature
<222> LOCATION: 12..13
<223> OTHER INFORMATION: n is BzdU

<400> SEQUENCE: 98
ggtggtggtg gnngtggtgg tggtgg                                         26

<210> SEQ ID NO 99
<211> LENGTH: 26
<212> TYPE: DNA
<213> ORGANISM: Artificial Sequence
<220> FEATURE:
<223> OTHER INFORMATION: aptamer 1642-116 which is modified AS1411
     having hydrophobic groups such as BN at 5 position of dU
     (5-(N-benzylcarboxyamide)-2'-deoxyuridine, BzdU)
<220> FEATURE:
<221> NAME/KEY: misc_feature
<222> LOCATION: 12..13; 15
<223> OTHER INFORMATION: n is BzdU

<400> SEQUENCE: 99
ggtggtggtg gnngnggtgg tggtgg                                         26

<210> SEQ ID NO 100
<211> LENGTH: 26
<212> TYPE: DNA
<213> ORGANISM: Artificial Sequence
<220> FEATURE:
<223> OTHER INFORMATION: aptamer 1642-117 which is modified AS1411
     having hydrophobic groups such as BN at 5 position of dU
     (5-(N-benzylcarboxyamide)-2'-deoxyuridine, BzdU)
<220> FEATURE:
<221> NAME/KEY: misc_feature
<222> LOCATION: 12..13; 18
<223> OTHER INFORMATION: n is BzdU

```
<400> SEQUENCE: 100
ggtggtggtg gnngtggngg tggtgg                                          26

<210> SEQ ID NO 101
<211> LENGTH: 26
<212> TYPE: DNA
<213> ORGANISM: Artificial Sequence
<220> FEATURE:
<223> OTHER INFORMATION: aptamer 1642-118 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 12..13; 21
<223> OTHER INFORMATION: n is BzdU

<400> SEQUENCE: 101
ggtggtggtg gnngtggtgg nggtgg                                          26

<210> SEQ ID NO 102
<211> LENGTH: 26
<212> TYPE: DNA
<213> ORGANISM: Artificial Sequence
<220> FEATURE:
<223> OTHER INFORMATION: aptamer 1642-119 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 9; 12..13
<223> OTHER INFORMATION: n is BzdU

<400> SEQUENCE: 102
ggtggtggng gnngtggtgg tggtgg                                          26

<210> SEQ ID NO 103
<211> LENGTH: 26
<212> TYPE: DNA
<213> ORGANISM: Artificial Sequence
<220> FEATURE:
<223> OTHER INFORMATION: aptamer 1642-120 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 6; 12..13
<223> OTHER INFORMATION: n is BzdU

<400> SEQUENCE: 103
ggtggnggtg gnngtggtgg tggtgg                                          26

<210> SEQ ID NO 104
<211> LENGTH: 26
<212> TYPE: DNA
<213> ORGANISM: Artificial Sequence
<220> FEATURE:
<223> OTHER INFORMATION: aptamer 1642-121 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 3; 12..13
<223> OTHER INFORMATION: n is BzdU

<400> SEQUENCE: 104
ggnggtggtg gnngtggtgg tggtgg                                          26

<210> SEQ ID NO 105
<211> LENGTH: 26
<212> TYPE: DNA
```

```
<213> ORGANISM: Artificial Sequence
<220> FEATURE:
<223> OTHER INFORMATION: aptamer 1642-122 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 9; 15
<223> OTHER INFORMATION: n is BzdU

<400> SEQUENCE: 105
ggtggtggng gttgnggtgg tggtgg                                           26

<210> SEQ ID NO 106
<211> LENGTH: 26
<212> TYPE: DNA
<213> ORGANISM: Artificial Sequence
<220> FEATURE:
<223> OTHER INFORMATION: aptamer 1642-123 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 6; 18
<223> OTHER INFORMATION: n is BzdU

<400> SEQUENCE: 106
ggtggnggtg gttgtggngg tggtgg                                           26

<210> SEQ ID NO 107
<211> LENGTH: 26
<212> TYPE: DNA
<213> ORGANISM: Artificial Sequence
<220> FEATURE:
<223> OTHER INFORMATION: aptamer 1642-124 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 3; 21
<223> OTHER INFORMATION: n is BzdU

<400> SEQUENCE: 107
ggnggtggtg gttgtggtgg nggtgg                                           26

<210> SEQ ID NO 108
<211> LENGTH: 26
<212> TYPE: DNA
<213> ORGANISM: Artificial Sequence
<220> FEATURE:
<223> OTHER INFORMATION: aptamer 1642-125 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 6; 9; 15; 18; 21
<223> OTHER INFORMATION: n is BzdU

<400> SEQUENCE: 108
ggtggnggng gttgnggngg nggtgg                                           26

<210> SEQ ID NO 109
<211> LENGTH: 26
<212> TYPE: DNA
<213> ORGANISM: Artificial Sequence
<220> FEATURE:
<223> OTHER INFORMATION: aptamer 1642-126 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 3; 6; 9; 15; 18; 24
```

```
<223> OTHER INFORMATION: n is BzdU

<400> SEQUENCE: 109
ggnggnggng gttgnggngg tggngg                                26

<210> SEQ ID NO 110
<211> LENGTH: 28
<212> TYPE: DNA
<213> ORGANISM: Artificial Sequence
<220> FEATURE:
<223> OTHER INFORMATION: aptamer 1642-127 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 1; 28
<223> OTHER INFORMATION: n is BzdU

<400> SEQUENCE: 110
nggtggtggt ggttgtggtg gtggtggn                              28

<210> SEQ ID NO 111
<211> LENGTH: 26
<212> TYPE: DNA
<213> ORGANISM: Artificial Sequence
<220> FEATURE:
<223> OTHER INFORMATION: aptamer 1642-129 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 3; 6; 9; 12..13; 15; 18; 21; 24
<223> OTHER INFORMATION: n is BzdU

<400> SEQUENCE: 111
ccnccnccnc cnncnccncc nccncc                                26

<210> SEQ ID NO 112
<211> LENGTH: 26
<212> TYPE: DNA
<213> ORGANISM: Artificial Sequence
<220> FEATURE:
<223> OTHER INFORMATION: aptamer 1642-130 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 3; 6; 9; 18; 21; 24
<223> OTHER INFORMATION: n is BzdU

<400> SEQUENCE: 112
ccnccnccnc cttctccncc nccncc                                26

<210> SEQ ID NO 113
<211> LENGTH: 26
<212> TYPE: DNA
<213> ORGANISM: Artificial Sequence
<220> FEATURE:
<223> OTHER INFORMATION: aptamer 1642-131 which is modified AS1411
      having hydrophobic groups such as BN at 5 position of dU
      (5-(N-benzylcarboxyamide)-2'-deoxyuridine, BzdU)
<220> FEATURE:
<221> NAME/KEY: misc_feature
<222> LOCATION: 12..13; 15
<223> OTHER INFORMATION: n is BzdU

<400> SEQUENCE: 113
cctcctcctc cnncncctcc tcctcc                                26

<210> SEQ ID NO 114
```

```
<211> LENGTH: 26
<212> TYPE: DNA
<213> ORGANISM: Artificial Sequence
<220> FEATURE:
<223> OTHER INFORMATION: aptamer 1642-132 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 3; 6; 9; 12..13; 15; 18; 21; 24
<223> OTHER INFORMATION: n is NapdU

<400> SEQUENCE: 114
ggnggnggng gnngnggngg nggngg                                              26

<210> SEQ ID NO 115
<211> LENGTH: 26
<212> TYPE: DNA
<213> ORGANISM: Artificial Sequence
<220> FEATURE:
<223> OTHER INFORMATION: aptamer 1642-133 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 3; 6; 9; 18; 21; 24
<223> OTHER INFORMATION: n is NapdU

<400> SEQUENCE: 115
ggnggnggng gttgtggngg nggngg                                              26

<210> SEQ ID NO 116
<211> LENGTH: 26
<212> TYPE: DNA
<213> ORGANISM: Artificial Sequence
<220> FEATURE:
<223> OTHER INFORMATION: aptamer 1642-134 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 3; 6; 21; 24
<223> OTHER INFORMATION: n is NapdU

<400> SEQUENCE: 116
ggnggnggtg gttgtggtgg nggngg                                              26

<210> SEQ ID NO 117
<211> LENGTH: 26
<212> TYPE: DNA
<213> ORGANISM: Artificial Sequence
<220> FEATURE:
<223> OTHER INFORMATION: aptamer 1642-135 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 6; 9; 18; 21
<223> OTHER INFORMATION: n is NapdU

<400> SEQUENCE: 117
ggtggnggng gttgtggngg nggtgg                                              26

<210> SEQ ID NO 118
<211> LENGTH: 26
<212> TYPE: DNA
<213> ORGANISM: Artificial Sequence
<220> FEATURE:
<223> OTHER INFORMATION: aptamer 1642-136 which is modified AS1411
      having hydrophobic groups such as Nap at 5 position of dU
      (5-(N-naphthylcarboxyamide)-2'-deoxyuridine, NapdU)
<220> FEATURE:
```

<221> NAME/KEY: misc_feature
<222> LOCATION: 3; 24
<223> OTHER INFORMATION: n is NapdU

<400> SEQUENCE: 118
ggnggtggtg gttgtggtgg tggngg                                              26

<210> SEQ ID NO 119
<211> LENGTH: 26
<212> TYPE: DNA
<213> ORGANISM: Artificial Sequence
<220> FEATURE:
<223> OTHER INFORMATION: aptamer 1642-137 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 6; 21
<223> OTHER INFORMATION: n is NapdU

<400> SEQUENCE: 119
ggtggnggtg gttgtggtgg nggtgg                                              26

<210> SEQ ID NO 120
<211> LENGTH: 26
<212> TYPE: DNA
<213> ORGANISM: Artificial Sequence
<220> FEATURE:
<223> OTHER INFORMATION: aptamer 1642-138 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 9; 18
<223> OTHER INFORMATION: n is NapdU

<400> SEQUENCE: 120
ggtggtggng gttgtggngg tggtgg                                              26

<210> SEQ ID NO 121
<211> LENGTH: 26
<212> TYPE: DNA
<213> ORGANISM: Artificial Sequence
<220> FEATURE:
<223> OTHER INFORMATION: aptamer 1642-139 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 3; 9; 18; 24
<223> OTHER INFORMATION: n is NapdU

<400> SEQUENCE: 121
ggnggtggng gttgtggngg tggngg                                              26

<210> SEQ ID NO 122
<211> LENGTH: 26
<212> TYPE: DNA
<213> ORGANISM: Artificial Sequence
<220> FEATURE:
<223> OTHER INFORMATION: aptamer 1642-140 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 13
<223> OTHER INFORMATION: n is NapdU

<400> SEQUENCE: 122
ggtggtggtg gtngtggtgg tggtgg                                              26

<210> SEQ ID NO 123
<211> LENGTH: 26
<212> TYPE: DNA
<213> ORGANISM: Artificial Sequence
<220> FEATURE:
<223> OTHER INFORMATION: aptamer 1642-141 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 12..13; 15
<223> OTHER INFORMATION: n is NapdU

<400> SEQUENCE: 123
ggtggtggtg gnngnggtgg tggtgg                                              26

<210> SEQ ID NO 124
<211> LENGTH: 26
<212> TYPE: DNA
<213> ORGANISM: Artificial Sequence
<220> FEATURE:
<223> OTHER INFORMATION: aptamer 1642-142 which is modified AS1411
      having hydrophobic groups such as Nap at 5 position of dU
      (5-(N-naphthylcarboxyamide)-2'-deoxyuridine, NapdU), wherein
<220> FEATURE:
<221> NAME/KEY: misc_feature
<222> LOCATION: 12; 15
<223> OTHER INFORMATION: n is NapdU

<400> SEQUENCE: 124
ggtggtggtg gntgnggtgg tggtgg                                              26

<210> SEQ ID NO 125
<211> LENGTH: 26
<212> TYPE: DNA
<213> ORGANISM: Artificial Sequence
<220> FEATURE:
<223> OTHER INFORMATION: aptamer 1642-143 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 3
<223> OTHER INFORMATION: n is NapdU

<400> SEQUENCE: 125
ggnggtggtg gttgtggtgg tggtgg                                              26

<210> SEQ ID NO 126
<211> LENGTH: 26
<212> TYPE: DNA
<213> ORGANISM: Artificial Sequence
<220> FEATURE:
<223> OTHER INFORMATION: aptamer 1642-144 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 6
<223> OTHER INFORMATION: n is NapdU

<400> SEQUENCE: 126
ggtggnggtg gttgtggtgg tggtgg                                              26

<210> SEQ ID NO 127
<211> LENGTH: 26
<212> TYPE: DNA
<213> ORGANISM: Artificial Sequence
<220> FEATURE:
<223> OTHER INFORMATION: aptamer 1642-145 which is modified AS1411 having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 9
<223> OTHER INFORMATION: n is NapdU

<400> SEQUENCE: 127
ggtggtggng gttgtggtgg tggtgg                                          26

<210> SEQ ID NO 128
<211> LENGTH: 26
<212> TYPE: DNA
<213> ORGANISM: Artificial Sequence
<220> FEATURE:
<223> OTHER INFORMATION: aptamer 1642-146 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 12
<223> OTHER INFORMATION: n is NapdU

<400> SEQUENCE: 128
ggtggtggtg gntgtggtgg tggtgg                                          26

<210> SEQ ID NO 129
<211> LENGTH: 26
<212> TYPE: DNA
<213> ORGANISM: Artificial Sequence
<220> FEATURE:
<223> OTHER INFORMATION: aptamer 1642-147 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 13
<223> OTHER INFORMATION: n is NapdU

<400> SEQUENCE: 129
ggtggtggtg gtngtggtgg tggtgg                                          26

<210> SEQ ID NO 130
<211> LENGTH: 26
<212> TYPE: DNA
<213> ORGANISM: Artificial Sequence
<220> FEATURE:
<223> OTHER INFORMATION: aptamer 1642-148 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 15
<223> OTHER INFORMATION: n is NapdU

<400> SEQUENCE: 130
ggtggtggtg gttgnggtgg tggtgg                                          26

<210> SEQ ID NO 131
<211> LENGTH: 26
<212> TYPE: DNA
<213> ORGANISM: Artificial Sequence
<220> FEATURE:
<223> OTHER INFORMATION: aptamer 1642-149 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 18
<223> OTHER INFORMATION: n is NapdU

<400> SEQUENCE: 131

```
ggtggtggtg gttgtggngg tggtgg                                    26
```

<210> SEQ ID NO 132
<211> LENGTH: 26
<212> TYPE: DNA
<213> ORGANISM: Artificial Sequence
<220> FEATURE:
<223> OTHER INFORMATION: aptamer 1642-150 which is modified AS1411
      having hydrophobic groups such as Nap at 5 position of dU
      (5-(N-naphthylcarboxamide)-2'-deoxyuridine, NapdU)
<220> FEATURE:
<221> NAME/KEY: misc_feature
<222> LOCATION: 21
<223> OTHER INFORMATION: n is NapdU

<400> SEQUENCE: 132

```
ggtggtggtg gttgtggtgg nggtgg                                    26
```

<210> SEQ ID NO 133
<211> LENGTH: 26
<212> TYPE: DNA
<213> ORGANISM: Artificial Sequence
<220> FEATURE:
<223> OTHER INFORMATION: aptamer 1642-151 which is modified AS1411
      having hydrophobic groups such as Nap at 5 position of dU
      (5-(N-naphthylcarboxamide)-2'-deoxyuridine, NapdU)
<220> FEATURE:
<221> NAME/KEY: misc_feature
<222> LOCATION: 24
<223> OTHER INFORMATION: n is NapdU

<400> SEQUENCE: 133

```
ggtggtggtg gttgtggtgg tggngg                                    26
```

<210> SEQ ID NO 134
<211> LENGTH: 26
<212> TYPE: DNA
<213> ORGANISM: Artificial Sequence
<220> FEATURE:
<223> OTHER INFORMATION: aptamer 1642-152 which is modified AS1411
      having hydrophobic groups such as Nap at 5 position of dU
      (5-(N-naphthylcarboxamide)-2'-deoxyuridine, NapdU)
<220> FEATURE:
<221> NAME/KEY: misc_feature
<222> LOCATION: 21; 24
<223> OTHER INFORMATION: n is NapdU

<400> SEQUENCE: 134

```
ggtggtggtg gttgtggtgg nggngg                                    26
```

<210> SEQ ID NO 135
<211> LENGTH: 26
<212> TYPE: DNA
<213> ORGANISM: Artificial Sequence
<220> FEATURE:
<223> OTHER INFORMATION: aptamer 1642-153 which is modified AS1411
      having hydrophobic groups such as Nap at 5 position of dU
      (5-(N-naphthylcarboxamide)-2'-deoxyuridine, NapdU)
<220> FEATURE:
<221> NAME/KEY: misc_feature
<222> LOCATION: 18; 24
<223> OTHER INFORMATION: n is NapdU

<400> SEQUENCE: 135

```
ggtggtggtg gttgtggngg tggngg                                    26
```

<210> SEQ ID NO 136
<211> LENGTH: 26
<212> TYPE: DNA
<213> ORGANISM: Artificial Sequence

```
<220> FEATURE:
<223> OTHER INFORMATION: aptamer 1642-154 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 15; 24
<223> OTHER INFORMATION: n is NapdU

<400> SEQUENCE: 136
ggtggtggtg gttgnggtgg tggngg                                              26

<210> SEQ ID NO 137
<211> LENGTH: 26
<212> TYPE: DNA
<213> ORGANISM: Artificial Sequence
<220> FEATURE:
<223> OTHER INFORMATION: aptamer 1642-155 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 13; 24
<223> OTHER INFORMATION: n is NapdU

<400> SEQUENCE: 137
ggtggtggtg gtngtggtgg tggngg                                              26

<210> SEQ ID NO 138
<211> LENGTH: 26
<212> TYPE: DNA
<213> ORGANISM: Artificial Sequence
<220> FEATURE:
<223> OTHER INFORMATION: aptamer 1642-156 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 12; 24
<223> OTHER INFORMATION: n is NapdU

<400> SEQUENCE: 138
ggtggtggtg gntgtggtgg tggngg                                              26

<210> SEQ ID NO 139
<211> LENGTH: 26
<212> TYPE: DNA
<213> ORGANISM: Artificial Sequence
<220> FEATURE:
<223> OTHER INFORMATION: aptamer 1642-157 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 9; 24
<223> OTHER INFORMATION: n is NapdU

<400> SEQUENCE: 139
ggtggtggng gttgtggtgg tggngg                                              26

<210> SEQ ID NO 140
<211> LENGTH: 26
<212> TYPE: DNA
<213> ORGANISM: Artificial Sequence
<220> FEATURE:
<223> OTHER INFORMATION: aptamer 1642-158 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 6; 24
<223> OTHER INFORMATION: n is NapdU
```

<210> SEQ ID NO 141
<211> LENGTH: 26
<212> TYPE: DNA
<213> ORGANISM: Artificial Sequence
<220> FEATURE:
<223> OTHER INFORMATION: aptamer 1642-159 which is modified AS1411 having hydrophobic groups such as Nap at 5 position of dU (5-(N-naphthylcarboxyamide)-2'-deoxyuridine, NapdU)
<220> FEATURE:
<221> NAME/KEY: misc_feature
<222> LOCATION: 3; 24
<223> OTHER INFORMATION: n is NapdU

<400> SEQUENCE: 141
ggnggtggtg gttgtggtgg tggngg　　　　　　　　　　　　　　　26

<210> SEQ ID NO 142
<211> LENGTH: 26
<212> TYPE: DNA
<213> ORGANISM: Artificial Sequence
<220> FEATURE:
<223> OTHER INFORMATION: aptamer 1642-160 which is modified AS1411 having hydrophobic groups such as Nap at 5 position of dU (5-(N-naphthylcarboxyamide)-2'-deoxyuridine, NapdU)
<220> FEATURE:
<221> NAME/KEY: misc_feature
<222> LOCATION: 12..13; 24
<223> OTHER INFORMATION: n is NapdU

<400> SEQUENCE: 142
ggtggtggtg gnngtggtgg tggngg　　　　　　　　　　　　　　　26

<210> SEQ ID NO 143
<211> LENGTH: 26
<212> TYPE: DNA
<213> ORGANISM: Artificial Sequence
<220> FEATURE:
<223> OTHER INFORMATION: aptamer 1642-161 which is modified AS1411 having hydrophobic groups such as Nap at 5 position of dU (5-(N-naphthylcarboxyamide)-2'-deoxyuridine, NapdU)
<220> FEATURE:
<221> NAME/KEY: misc_feature
<222> LOCATION: 12..13
<223> OTHER INFORMATION: n is NapdU

<400> SEQUENCE: 143
ggtggtggtg gnngtggtgg tggtgg　　　　　　　　　　　　　　　26

<210> SEQ ID NO 144
<211> LENGTH: 26
<212> TYPE: DNA
<213> ORGANISM: Artificial Sequence
<220> FEATURE:
<223> OTHER INFORMATION: aptamer 1642-162 which is modified AS1411 having hydrophobic groups such as Nap at 5 position of dU (5-(N-naphthylcarboxyamide)-2'-deoxyuridine, NapdU)
<220> FEATURE:
<221> NAME/KEY: misc_feature
<222> LOCATION: 12..13; 15
<223> OTHER INFORMATION: n is NapdU

<400> SEQUENCE: 144
ggtggtggtg gnngnggtgg tggtgg　　　　　　　　　　　　　　　26

<210> SEQ ID NO 145
<211> LENGTH: 26

```
<212> TYPE: DNA
<213> ORGANISM: Artificial Sequence
<220> FEATURE:
<223> OTHER INFORMATION: aptamer 1642-163 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 12..13; 18
<223> OTHER INFORMATION: n is NapdU

<400> SEQUENCE: 145
ggtggtggtg gnngtggngg tggtgg                                           26

<210> SEQ ID NO 146
<211> LENGTH: 26
<212> TYPE: DNA
<213> ORGANISM: Artificial Sequence
<220> FEATURE:
<223> OTHER INFORMATION: aptamer 1642-164 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 12..13; 21
<223> OTHER INFORMATION: n is NapdU

<400> SEQUENCE: 146
ggtggtggtg gnngtggtgg nggtgg                                           26

<210> SEQ ID NO 147
<211> LENGTH: 26
<212> TYPE: DNA
<213> ORGANISM: Artificial Sequence
<220> FEATURE:
<223> OTHER INFORMATION: aptamer 1642-165 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 9; 12..13
<223> OTHER INFORMATION: n is NapdU

<400> SEQUENCE: 147
ggtggtggng gnngtggtgg tggtgg                                           26

<210> SEQ ID NO 148
<211> LENGTH: 26
<212> TYPE: DNA
<213> ORGANISM: Artificial Sequence
<220> FEATURE:
<223> OTHER INFORMATION: aptamer 1642-166 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 6; 12..13
<223> OTHER INFORMATION: n is NapdU

<400> SEQUENCE: 148
ggtggnggtg gnngtggtgg tggtgg                                           26

<210> SEQ ID NO 149
<211> LENGTH: 26
<212> TYPE: DNA
<213> ORGANISM: Artificial Sequence
<220> FEATURE:
<223> OTHER INFORMATION: aptamer 1642-167 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
```

<222> LOCATION: 3; 12..13
<223> OTHER INFORMATION: n is NapdU

<400> SEQUENCE: 149
ggnggtggtg gnngtggtgg tggtgg                                              26

<210> SEQ ID NO 150
<211> LENGTH: 26
<212> TYPE: DNA
<213> ORGANISM: Artificial Sequence
<220> FEATURE:
<223> OTHER INFORMATION: aptamer 1642-168 which is modified AS1411
      having hydrophobic groups such as Nap at 5 position of dU
      (5-(N-naphthylcarboxamide)-2'-deoxyuridine, NapdU)
<220> FEATURE:
<221> NAME/KEY: misc_feature
<222> LOCATION: 9; 15
<223> OTHER INFORMATION: n is NapdU

<400> SEQUENCE: 150
ggtggtggng gttgnggtgg tggtgg                                              26

<210> SEQ ID NO 151
<211> LENGTH: 26
<212> TYPE: DNA
<213> ORGANISM: Artificial Sequence
<220> FEATURE:
<223> OTHER INFORMATION: aptamer 1642-169 which is modified AS1411
      having hydrophobic groups such as Nap at 5 position of dU
      (5-(N-naphthylcarboxamide)-2'-deoxyuridine, NapdU)
<220> FEATURE:
<221> NAME/KEY: misc_feature
<222> LOCATION: 6; 18
<223> OTHER INFORMATION: n is NapdU

<400> SEQUENCE: 151
ggtggnggtg gttgtggngg tggtgg                                              26

<210> SEQ ID NO 152
<211> LENGTH: 26
<212> TYPE: DNA
<213> ORGANISM: Artificial Sequence
<220> FEATURE:
<223> OTHER INFORMATION: aptamer 1642-170 which is modified AS1411
      having hydrophobic groups such as Nap at 5 position of dU
      (5-(N-naphthylcarboxamide)-2'-deoxyuridine, NapdU)
<220> FEATURE:
<221> NAME/KEY: misc_feature
<222> LOCATION: 3; 21
<223> OTHER INFORMATION: n is NapdU

<400> SEQUENCE: 152
ggnggtggtg gttgtggtgg nggtgg                                              26

<210> SEQ ID NO 153
<211> LENGTH: 26
<212> TYPE: DNA
<213> ORGANISM: Artificial Sequence
<220> FEATURE:
<223> OTHER INFORMATION: aptamer 1642-171 which is modified AS1411
      having hydrophobic groups such as Nap at 5 position of dU
      (5-(N-naphthylcarboxamide)-2'-deoxyuridine, NapdU)
<220> FEATURE:
<221> NAME/KEY: misc_feature
<222> LOCATION: 6; 9; 15; 18; 21
<223> OTHER INFORMATION: n is NapdU

<400> SEQUENCE: 153
ggtggnggng gttgnggngg nggtgg                                              26

```
<210> SEQ ID NO 154
<211> LENGTH: 26
<212> TYPE: DNA
<213> ORGANISM: Artificial Sequence
<220> FEATURE:
<223> OTHER INFORMATION: aptamer 1642-172 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 3; 6; 9; 15; 18; 24
<223> OTHER INFORMATION: n is NapdU

<400> SEQUENCE: 154
ggnggnggng gttgnggngg tggngg                                    26

<210> SEQ ID NO 155
<211> LENGTH: 28
<212> TYPE: DNA
<213> ORGANISM: Artificial Sequence
<220> FEATURE:
<223> OTHER INFORMATION: aptamer 1642-173 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 1; 28
<223> OTHER INFORMATION: n is NapdU

<400> SEQUENCE: 155
nggtggtggt ggttgtggtg gtggtggn                                  28

<210> SEQ ID NO 156
<211> LENGTH: 26
<212> TYPE: DNA
<213> ORGANISM: Artificial Sequence
<220> FEATURE:
<223> OTHER INFORMATION: aptamer 1642-174 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 3; 6; 9; 12..13; 15; 18; 21; 24
<223> OTHER INFORMATION: n is NapdU

<400> SEQUENCE: 156
ccnccnccnc cnncnccncc nccncc                                    26

<210> SEQ ID NO 157
<211> LENGTH: 26
<212> TYPE: DNA
<213> ORGANISM: Artificial Sequence
<220> FEATURE:
<223> OTHER INFORMATION: aptamer 1642-175 which is modified AS1411
      having hydrophobic groups such as Nap at 5 position of dU
      (5-(N-naphthylcarboxyamide)-2'-deoxyuridine, NapdU)
<220> FEATURE:
<221> NAME/KEY: misc_feature
<222> LOCATION: 3; 6; 9; 18; 21; 24
<223> OTHER INFORMATION: n is NapdU

<400> SEQUENCE: 157
ccnccnccnc cttctccncc nccncc                                    26

<210> SEQ ID NO 158
<211> LENGTH: 26
<212> TYPE: DNA
<213> ORGANISM: Artificial Sequence
<220> FEATURE:
<223> OTHER INFORMATION: aptamer 1642-176 which is modified AS1411
      having hydrophobic groups such as Nap at 5 position of dU
      (5-(N-naphthylcarboxyamide)-2'-deoxyuridine, NapdU)
```

```
<220> FEATURE:
<221> NAME/KEY: misc_feature
<222> LOCATION: 12..13; 15
<223> OTHER INFORMATION: n is NapdU

<400> SEQUENCE: 158
cctcctcctc cnncncctcc tcctcc                                          26

<210> SEQ ID NO 159
<211> LENGTH: 26
<212> TYPE: DNA
<213> ORGANISM: Artificial Sequence
<220> FEATURE:
<223> OTHER INFORMATION: aptamer 1642-177 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3; 6; 9; 12..13; 15; 18; 21; 24
<223> OTHER INFORMATION: n is 4-PBdU

<400> SEQUENCE: 159
ggnggnggng gnngnggngg nggngg                                          26

<210> SEQ ID NO 160
<211> LENGTH: 26
<212> TYPE: DNA
<213> ORGANISM: Artificial Sequence
<220> FEATURE:
<223> OTHER INFORMATION: aptamer 1642-178 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3; 6; 9; 18; 21; 24
<223> OTHER INFORMATION: n is 4-PBdU

<400> SEQUENCE: 160
ggnggnggng gttgtggngg nggngg                                          26

<210> SEQ ID NO 161
<211> LENGTH: 26
<212> TYPE: DNA
<213> ORGANISM: Artificial Sequence
<220> FEATURE:
<223> OTHER INFORMATION: aptamer 1642-179 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3; 6; 21; 24
<223> OTHER INFORMATION: n is 4-PBdU

<400> SEQUENCE: 161
ggnggnggtg gttgtggtgg nggngg                                          26

<210> SEQ ID NO 162
<211> LENGTH: 26
<212> TYPE: DNA
<213> ORGANISM: Artificial Sequence
<220> FEATURE:
<223> OTHER INFORMATION: aptamer 1642-180 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 6; 9; 18; 21
<223> OTHER INFORMATION: n is 4-PBdU

<400> SEQUENCE: 162
ggtggnggng gttgtggngg nggtgg                                          26
```

<210> SEQ ID NO 163
<211> LENGTH: 26
<212> TYPE: DNA
<213> ORGANISM: Artificial Sequence
<220> FEATURE:
<223> OTHER INFORMATION: aptamer 1642-181 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3; 24
<223> OTHER INFORMATION: n is 4-PBdU

<400> SEQUENCE: 163
ggnggtggtg gttgtggtgg tggngg                                          26

<210> SEQ ID NO 164
<211> LENGTH: 26
<212> TYPE: DNA
<213> ORGANISM: Artificial Sequence
<220> FEATURE:
<223> OTHER INFORMATION: aptamer 1642-182 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 6; 21
<223> OTHER INFORMATION: n is 4-PBdU

<400> SEQUENCE: 164
ggtggnggtg gttgtggtgg nggtgg                                          26

<210> SEQ ID NO 165
<211> LENGTH: 26
<212> TYPE: DNA
<213> ORGANISM: Artificial Sequence
<220> FEATURE:
<223> OTHER INFORMATION: aptamer 1642-183 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 9; 18
<223> OTHER INFORMATION: n is 4-PBdU

<400> SEQUENCE: 165
ggtggtggng gttgtggngg tggtgg                                          26

<210> SEQ ID NO 166
<211> LENGTH: 26
<212> TYPE: DNA
<213> ORGANISM: Artificial Sequence
<220> FEATURE:
<223> OTHER INFORMATION: aptamer 1642-184 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3; 9; 18; 24
<223> OTHER INFORMATION: n is 4-PBdU

<400> SEQUENCE: 166
ggnggtggng gttgtggngg tggngg                                          26

<210> SEQ ID NO 167
<211> LENGTH: 26
<212> TYPE: DNA
<213> ORGANISM: Artificial Sequence
<220> FEATURE:
<223> OTHER INFORMATION: aptamer 1642-185 which is modified AS1411

```
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 13
<223> OTHER INFORMATION: n is 4-PBdU

<400> SEQUENCE: 167
ggtggtggtg gtngtggtgg tggtgg                                               26

<210> SEQ ID NO 168
<211> LENGTH: 26
<212> TYPE: DNA
<213> ORGANISM: Artificial Sequence
<220> FEATURE:
<223> OTHER INFORMATION: aptamer 1642-186 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 12..13; 15
<223> OTHER INFORMATION: n is 4-PBdU

<400> SEQUENCE: 168
ggtggtggtg gnngnggtgg tggtgg                                               26

<210> SEQ ID NO 169
<211> LENGTH: 26
<212> TYPE: DNA
<213> ORGANISM: Artificial Sequence
<220> FEATURE:
<223> OTHER INFORMATION: aptamer 1642-187 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 12; 15
<223> OTHER INFORMATION: n is 4-PBdU

<400> SEQUENCE: 169
ggtggtggtg gntgnggtgg tggtgg                                               26

<210> SEQ ID NO 170
<211> LENGTH: 26
<212> TYPE: DNA
<213> ORGANISM: Artificial Sequence
<220> FEATURE:
<223> OTHER INFORMATION: aptamer 1642-188 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3
<223> OTHER INFORMATION: n is 4-PBdU

<400> SEQUENCE: 170
ggnggtggtg gttgtggtgg tggtgg                                               26

<210> SEQ ID NO 171
<211> LENGTH: 26
<212> TYPE: DNA
<213> ORGANISM: Artificial Sequence
<220> FEATURE:
<223> OTHER INFORMATION: aptamer 1642-189 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 6
<223> OTHER INFORMATION: n is 4-PBdU

<400> SEQUENCE: 171
```
ggtggnggtg gttgtggtgg tggtgg                                              26

<210> SEQ ID NO 172
<211> LENGTH: 26
<212> TYPE: DNA
<213> ORGANISM: Artificial Sequence
<220> FEATURE:
<223> OTHER INFORMATION: aptamer 1642-190 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 9
<223> OTHER INFORMATION: n is 4-PBdU

<400> SEQUENCE: 172
ggtggtggng gttgtggtgg tggtgg                                              26

<210> SEQ ID NO 173
<211> LENGTH: 26
<212> TYPE: DNA
<213> ORGANISM: Artificial Sequence
<220> FEATURE:
<223> OTHER INFORMATION: aptamer 1642-191 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 12
<223> OTHER INFORMATION: n is 4-PBdU

<400> SEQUENCE: 173
ggtggtggtg gntgtggtgg tggtgg                                              26

<210> SEQ ID NO 174
<211> LENGTH: 26
<212> TYPE: DNA
<213> ORGANISM: Artificial Sequence
<220> FEATURE:
<223> OTHER INFORMATION: aptamer 1642-192 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 13
<223> OTHER INFORMATION: n is 4-PBdU

<400> SEQUENCE: 174
ggtggtggtg gtngtggtgg tggtgg                                              26

<210> SEQ ID NO 175
<211> LENGTH: 26
<212> TYPE: DNA
<213> ORGANISM: Artificial Sequence
<220> FEATURE:
<223> OTHER INFORMATION: aptamer 1642-193 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 15
<223> OTHER INFORMATION: n is 4-PBdU

<400> SEQUENCE: 175
ggtggtggtg gttgnggtgg tggtgg                                              26

<210> SEQ ID NO 176
<211> LENGTH: 26
<212> TYPE: DNA
<213> ORGANISM: Artificial Sequence

```
<220> FEATURE:
<223> OTHER INFORMATION: aptamer 1642-194 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 18
<223> OTHER INFORMATION: n is 4-PBdU

<400> SEQUENCE: 176
ggtggtggtg gttgtggngg tggtgg                                          26

<210> SEQ ID NO 177
<211> LENGTH: 26
<212> TYPE: DNA
<213> ORGANISM: Artificial Sequence
<220> FEATURE:
<223> OTHER INFORMATION: aptamer 1642-195 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 21
<223> OTHER INFORMATION: n is 4-PBdU

<400> SEQUENCE: 177
ggtggtggtg gttgtggtgg nggtgg                                          26

<210> SEQ ID NO 178
<211> LENGTH: 26
<212> TYPE: DNA
<213> ORGANISM: Artificial Sequence
<220> FEATURE:
<223> OTHER INFORMATION: aptamer 1642-196 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 24
<223> OTHER INFORMATION: n is 4-PBdU

<400> SEQUENCE: 178
ggtggtggtg gttgtggtgg tggngg                                          26

<210> SEQ ID NO 179
<211> LENGTH: 26
<212> TYPE: DNA
<213> ORGANISM: Artificial Sequence
<220> FEATURE:
<223> OTHER INFORMATION: aptamer 1642-197 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 21; 24
<223> OTHER INFORMATION: n is 4-PBdU

<400> SEQUENCE: 179
ggtggtggtg gttgtggtgg nggngg                                          26

<210> SEQ ID NO 180
<211> LENGTH: 26
<212> TYPE: DNA
<213> ORGANISM: Artificial Sequence
<220> FEATURE:
<223> OTHER INFORMATION: aptamer 1642-198 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 18; 24
<223> OTHER INFORMATION: n is 4-PBdU
```

```
<400> SEQUENCE: 180
ggtggtggtg gttgtggngg tggngg                                          26

<210> SEQ ID NO 181
<211> LENGTH: 26
<212> TYPE: DNA
<213> ORGANISM: Artificial Sequence
<220> FEATURE:
<223> OTHER INFORMATION: aptamer 1642-199 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 15; 24
<223> OTHER INFORMATION: n is 4-PBdU

<400> SEQUENCE: 181
ggtggtggtg gttgnggtgg tggngg                                          26

<210> SEQ ID NO 182
<211> LENGTH: 26
<212> TYPE: DNA
<213> ORGANISM: Artificial Sequence
<220> FEATURE:
<223> OTHER INFORMATION: aptamer 1642-200 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 13; 24
<223> OTHER INFORMATION: n is 4-PBdU

<400> SEQUENCE: 182
ggtggtggtg gtngtggtgg tggngg                                          26

<210> SEQ ID NO 183
<211> LENGTH: 26
<212> TYPE: DNA
<213> ORGANISM: Artificial Sequence
<220> FEATURE:
<223> OTHER INFORMATION: aptamer 1642-201 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 12; 24
<223> OTHER INFORMATION: n is 4-PBdU

<400> SEQUENCE: 183
ggtggtggtg gntgtggtgg tggngg                                          26

<210> SEQ ID NO 184
<211> LENGTH: 26
<212> TYPE: DNA
<213> ORGANISM: Artificial Sequence
<220> FEATURE:
<223> OTHER INFORMATION: aptamer 1642-202 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 9; 24
<223> OTHER INFORMATION: n is 4-PBdU

<400> SEQUENCE: 184
ggtggtggng gttgtggtgg tggngg                                          26

<210> SEQ ID NO 185
<211> LENGTH: 26
```

```
<212> TYPE: DNA
<213> ORGANISM: Artificial Sequence
<220> FEATURE:
<223> OTHER INFORMATION: aptamer 1642-203 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 6; 24
<223> OTHER INFORMATION: n is 4-PBdU

<400> SEQUENCE: 185
ggtggnggtg gttgtggtgg tggngg                                       26

<210> SEQ ID NO 186
<211> LENGTH: 26
<212> TYPE: DNA
<213> ORGANISM: Artificial Sequence
<220> FEATURE:
<223> OTHER INFORMATION: aptamer 1642-204 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3; 24
<223> OTHER INFORMATION: n is 4-PBdU

<400> SEQUENCE: 186
ggnggtggtg gttgtggtgg tggngg                                       26

<210> SEQ ID NO 187
<211> LENGTH: 26
<212> TYPE: DNA
<213> ORGANISM: Artificial Sequence
<220> FEATURE:
<223> OTHER INFORMATION: aptamer 1642-205 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 12..13; 24
<223> OTHER INFORMATION: n is 4-PBdU

<400> SEQUENCE: 187
ggtggtggtg gnngtggtgg tggngg                                       26

<210> SEQ ID NO 188
<211> LENGTH: 26
<212> TYPE: DNA
<213> ORGANISM: Artificial Sequence
<220> FEATURE:
<223> OTHER INFORMATION: aptamer 1642-206 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 12..13
<223> OTHER INFORMATION: n is 4-PBdU

<400> SEQUENCE: 188
ggtggtggtg gnngtggtgg tggtgg                                       26

<210> SEQ ID NO 189
<211> LENGTH: 26
<212> TYPE: DNA
<213> ORGANISM: Artificial Sequence
<220> FEATURE:
<223> OTHER INFORMATION: aptamer 1642-207 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
```

```
<222> LOCATION: 12..13; 15
<223> OTHER INFORMATION: n is 4-PBdU

<400> SEQUENCE: 189
ggtggtggtg gnngnggtgg tggtgg                                           26

<210> SEQ ID NO 190
<211> LENGTH: 26
<212> TYPE: DNA
<213> ORGANISM: Artificial Sequence
<220> FEATURE:
<223> OTHER INFORMATION: aptamer 1642-208 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 12..13; 18
<223> OTHER INFORMATION: n is 4-PBdU

<400> SEQUENCE: 190
ggtggtggtg gnngtggngg tggtgg                                           26

<210> SEQ ID NO 191
<211> LENGTH: 26
<212> TYPE: DNA
<213> ORGANISM: Artificial Sequence
<220> FEATURE:
<223> OTHER INFORMATION: aptamer 1642-209 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 12..13; 21
<223> OTHER INFORMATION: n is 4-PBdU

<400> SEQUENCE: 191
ggtggtggtg gnngtggtgg nggtgg                                           26

<210> SEQ ID NO 192
<211> LENGTH: 26
<212> TYPE: DNA
<213> ORGANISM: Artificial Sequence
<220> FEATURE:
<223> OTHER INFORMATION: aptamer 1642-210 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 9; 12..13
<223> OTHER INFORMATION: n is 4-PBdU

<400> SEQUENCE: 192
ggtggtggng gnngtggtgg tggtgg                                           26

<210> SEQ ID NO 193
<211> LENGTH: 26
<212> TYPE: DNA
<213> ORGANISM: Artificial Sequence
<220> FEATURE:
<223> OTHER INFORMATION: aptamer 1642-211 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 6; 12..13
<223> OTHER INFORMATION: n is 4-PBdU

<400> SEQUENCE: 193
ggtggnggtg gnngtggtgg tggtgg                                           26
```

```
<210> SEQ ID NO 194
<211> LENGTH: 26
<212> TYPE: DNA
<213> ORGANISM: Artificial Sequence
<220> FEATURE:
<223> OTHER INFORMATION: aptamer 1642-212 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3; 12..13
<223> OTHER INFORMATION: n is 4-PBdU

<400> SEQUENCE: 194
ggnggtggtg gnngtggtgg tggtgg                                        26

<210> SEQ ID NO 195
<211> LENGTH: 26
<212> TYPE: DNA
<213> ORGANISM: Artificial Sequence
<220> FEATURE:
<223> OTHER INFORMATION: aptamer 1642-213 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 9; 15
<223> OTHER INFORMATION: n is 4-PBdU

<400> SEQUENCE: 195
ggtggtggng gttgnggtgg tggtgg                                        26

<210> SEQ ID NO 196
<211> LENGTH: 26
<212> TYPE: DNA
<213> ORGANISM: Artificial Sequence
<220> FEATURE:
<223> OTHER INFORMATION: aptamer 1642-214 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 6; 18
<223> OTHER INFORMATION: n is 4-PBdU

<400> SEQUENCE: 196
ggtggnggtg gttgtggngg tggtgg                                        26

<210> SEQ ID NO 197
<211> LENGTH: 26
<212> TYPE: DNA
<213> ORGANISM: Artificial Sequence
<220> FEATURE:
<223> OTHER INFORMATION: aptamer 1642-215 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3; 21
<223> OTHER INFORMATION: n is 4-PBdU

<400> SEQUENCE: 197
ggnggtggtg gttgtggtgg nggtgg                                        26

<210> SEQ ID NO 198
<211> LENGTH: 26
<212> TYPE: DNA
<213> ORGANISM: Artificial Sequence
<220> FEATURE:
<223> OTHER INFORMATION: aptamer 1642-216 which is modified AS1411
      having hydrophobic groups such as 4-PB at 5 position of dU
      (5-(N-4-pyrrolebenzylcarboxyamide)-2'-deoxyuridine, 4-PBdU)
```

```
<220> FEATURE:
<221> NAME/KEY: misc_feature
<222> LOCATION: 6; 9; 15; 18; 21
<223> OTHER INFORMATION: n is 4-PBdU

<400> SEQUENCE: 198
ggtggnggng gttgnggngg nggtgg                                          26

<210> SEQ ID NO 199
<211> LENGTH: 26
<212> TYPE: DNA
<213> ORGANISM: Artificial Sequence
<220> FEATURE:
<223> OTHER INFORMATION: aptamer 1642-217 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3; 6; 9; 15; 18; 24
<223> OTHER INFORMATION: n is 4-PBdU

<400> SEQUENCE: 199
ggnggnggng gttgnggngg tggngg                                          26

<210> SEQ ID NO 200
<211> LENGTH: 28
<212> TYPE: DNA
<213> ORGANISM: Artificial Sequence
<220> FEATURE:
<223> OTHER INFORMATION: aptamer 1642-218 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 1; 28
<223> OTHER INFORMATION: n is 4-PBdU

<400> SEQUENCE: 200
nggtggtggt ggttgtggtg gtggtggn                                        28

<210> SEQ ID NO 201
<211> LENGTH: 26
<212> TYPE: DNA
<213> ORGANISM: Artificial Sequence
<220> FEATURE:
<223> OTHER INFORMATION: aptamer 1642-219 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3; 6; 9; 12..13; 15; 18; 21; 24
<223> OTHER INFORMATION: n is 4-PBdU

<400> SEQUENCE: 201
ccnccnccnc cnnncccncc nccncc                                          26

<210> SEQ ID NO 202
<211> LENGTH: 26
<212> TYPE: DNA
<213> ORGANISM: Artificial Sequence
<220> FEATURE:
<223> OTHER INFORMATION: aptamer 1642-220 which is modified AS1411
      having hydrophobic groups such as 4-PB at 5 position of dU
      (5-(N-4-pyrrolebenzylcarboxyamide)-2'-deoxyuridine, 4-PBdU)
<220> FEATURE:
<221> NAME/KEY: misc_feature
<222> LOCATION: 3; 6; 9; 18; 21; 24
<223> OTHER INFORMATION: n is 4-PBdU

<400> SEQUENCE: 202
ccnccnccnc cttctccncc nccncc                                          26
```

<210> SEQ ID NO 203
<211> LENGTH: 26
<212> TYPE: DNA
<213> ORGANISM: Artificial Sequence
<220> FEATURE:
<223> OTHER INFORMATION: aptamer 1642-221 which is modified AS1411
having hydrophobic groups such as 4-PB at 5 position of dU
(5-(N-4-pyrrolebenzylcarboxyamide)-2'-deoxyuridine, 4-PBdU)
<220> FEATURE:
<221> NAME/KEY: misc_feature
<222> LOCATION: 12..13; 15
<223> OTHER INFORMATION: n is 4-PBdU

<400> SEQUENCE: 203
cctcctcctc cnncncctcc tcctcc                                          26

<210> SEQ ID NO 204
<211> LENGTH: 29
<212> TYPE: DNA
<213> ORGANISM: Artificial Sequence
<220> FEATURE:
<223> OTHER INFORMATION: Aptamer which is modified GRO29A containing Bz
at 5 position of dU (5-(N-benzylcarboxyamide)-2'-deoxyuridine,
BzdU)
<220> FEATURE:
<221> NAME/KEY: misc_feature
<222> LOCATION: 1..2
<223> OTHER INFORMATION: n is BzdU

<400> SEQUENCE: 204
nntggtggtg gtggttgtgg tggtggtgg                                       29

<210> SEQ ID NO 205
<211> LENGTH: 29
<212> TYPE: DNA
<213> ORGANISM: Artificial Sequence
<220> FEATURE:
<223> OTHER INFORMATION: Aptamer which is modified GRO29A containing Bz
at 5 position of dU (5-(N-benzylcarboxyamide)-2'-deoxyuridine,
BzdU)
<220> FEATURE:
<221> NAME/KEY: misc_feature
<222> LOCATION: 1; 3
<223> OTHER INFORMATION: n is BzdU

<400> SEQUENCE: 205
ntnggtggtg gtggttgtgg tggtggtgg                                       29

<210> SEQ ID NO 206
<211> LENGTH: 29
<212> TYPE: DNA
<213> ORGANISM: Artificial Sequence
<220> FEATURE:
<223> OTHER INFORMATION: Aptamer which is modified GRO29A containing Bz
at 5 position of dU (5-(N-benzylcarboxyamide)-2'-deoxyuridine,
BzdU)
<220> FEATURE:
<221> NAME/KEY: misc_feature
<222> LOCATION: 1..3; 6; 9; 12; 15..16; 18; 21; 24; 27
<223> OTHER INFORMATION: n is BzdU

<400> SEQUENCE: 206
nnnggnggng gnggnngngg nggnggngg                                       29

<210> SEQ ID NO 207
<211> LENGTH: 26
<212> TYPE: DNA
<213> ORGANISM: Artificial Sequence
<220> FEATURE:
<223> OTHER INFORMATION: Aptamer which is control AS1411, wherein all

```
            'T' is substituted with NapdU
<220> FEATURE:
<221> NAME/KEY: misc_feature
<222> LOCATION: 3; 6; 9; 12..13; 15; 18; 21; 24
<223> OTHER INFORMATION: n is NapdU

<400> SEQUENCE: 207
ccnccnccnc cnncnccncc nccncc                                          26

<210> SEQ ID NO 208
<211> LENGTH: 26
<212> TYPE: DNA
<213> ORGANISM: Artificial Sequence
<220> FEATURE:
<223> OTHER INFORMATION: Aptamer which is AS1411, wherein all 'T' is
      substituted with NapdU
<220> FEATURE:
<221> NAME/KEY: misc_feature
<222> LOCATION: 3; 6; 9; 12..13; 15; 18; 21; 24
<223> OTHER INFORMATION: n is NapdU

<400> SEQUENCE: 208
ggnggnggng gnngnggngg nggngg                                          26

<210> SEQ ID NO 209
<211> LENGTH: 26
<212> TYPE: DNA
<213> ORGANISM: Artificial Sequence
<220> FEATURE:
<223> OTHER INFORMATION: Aptamer which is control AS1411, wherein all
      'T' is substituted with 4-PBdU
<220> FEATURE:
<221> NAME/KEY: misc_feature
<222> LOCATION: 3; 6; 9; 12..13; 15; 18; 21; 24
<223> OTHER INFORMATION: n is 4-PBdU

<400> SEQUENCE: 209
ccnccnccnc cnncnccncc nccncc                                          26

<210> SEQ ID NO 210
<211> LENGTH: 26
<212> TYPE: DNA
<213> ORGANISM: Artificial Sequence
<220> FEATURE:
<223> OTHER INFORMATION: Aptamer which is AS1411, wherein all 'T' is
      substituted with 4-PBdU
<220> FEATURE:
<221> NAME/KEY: misc_feature
<222> LOCATION: 3; 6; 9; 12..13; 15; 18; 21; 24
<223> OTHER INFORMATION: n is 4-PBdU

<400> SEQUENCE: 210
ggnggnggng gnngnggngg nggngg                                          26
```

NUCLEOLIN SPECIFIC APTAMER AND USE THEREOF

CROSS-REFERENCE TO RELATED APPLICATION

This application claims the benefit of U.S. Provisional Application No. 61/169,348, filed Apr. 15, 2009, which is incorporated by reference herein in its entirety for any purpose.

TECHNICAL FIELD

The present invention relates to improved G-rich oligonucleotide (GRO) aptamers specific to nucleolin, a method of preparing the aptamers and a use of the aptamers for diagnosing and/or treating a nucleolin-associated disease.

BACKGROUND

Nucleolin is a protein that is expressed at elevated levels in transformed cells. Tumor cells have been shown to present nucleolin on the cell surface as well as expressing it in the cytoplasm and nucleus. Nucleolin plays multiple roles in the cell and is involved in ribosome biogenesis, cell growth, and DNA replication.

Aptamers are about 60~80mers of synthetic ribonucleic acid (RNA) or deoxyribonucleic acid (DNA) oligonucleotides which are known to be discovered by the process called systematic evolution of ligands by exponential enrichment (SELEX) based on high affinity and specific molecular fit with their targets of interest.

Aptamer have recently preferred to be applied for diagnosing and treating cancers as imaging target agents rather than monoclonal antibodies due to the following characteristics: inexpensive, efficient and rapid for production, highly stable for long-term storage, versatile molecules that can be easily modified with imaging probe, small size (8-15 kDa) resulting low immune risk and better penetration into target tissues in vivo, and high affinity molecular probe.

A large number of aptamers targeting cancer-related proteins, such as Wilim's tumor protein 1 (WT1), transcription factor 1 (TCF-1), human epidermal growth factor receptor 3 (HER-3), prostate-specific membrane antigene (PSMA), tenascin-C, nucleolin, pigpen and vascular endothelial growth factor (VEGF), have been developed to target and image cancers.

Some chemical modifications on the ribose backbone of aptamer nucleotides using 2'-amino or 2'-fluoro pyrimidines have been in situ and in vitro studied with the existing aptamers to be resistant to nucleases, more capable of transfer across membranes or more capable of specific binding to the target of interest, but they influence the structure of aptamers, resulting in the loss of aptamer properties.

SUMMARY OF THE INVENTION

The present inventors found that chemically 5-modified deoxyuridine (dU)-containing GRO29A (SEQ ID NO: 1) and AS1411 (SEQ ID NO: 2) exhibit much higher affinity to nucloelin protein than that of non-modified AS1411 and GRO29A in various cancer cell types, to complete the present invention.

An embodiment provides a nucleolin-specific aptamer having the nucleotide sequence of SEQ ID NO: 1 or 2, wherein one or more thymidines (T) are independently substituted with a modified deoxyuridine (dU), and wherein the modified dU is a deoxyuridine having a hydrophobic group at 5 position. The modified deoxyuridine may be 5-(N-benzylcarboxyamide)-2'-deoxyuridine (BzdU), 5-(N-naphthylcarboxyamide) -2'-deoxyuridine (NapdU), or 5-(N-4-pyrrolebenzylcarboxyamide) -2'-deoxyuridine (4-PBdU).

Another embodiment provides a pharmaceutical composition containing the nucleolin-specific aptamer. The pharmaceutical composition may a nucleolin inhibitor or agent for inhibiting an abnormal hyper-proliferation of cell, for example an anticancer agent.

Another embodiment provides a method of diagnosing a hyper-proliferative cell disorder, such as cancer using the nucleolin-specific aptamer labeled with a detectable label.

Another embodiment provides a method of treating a nucleolin-associated cancer using the nucleolin-specific aptamer.

Another embodiment provides a method of inhibiting an abnormal hyper-proliferation of call using the nucleolin-specific aptamer.

Still another embodiment provides a method of inhibiting nucleolin using the nucleolin-specific aptamer.

DETAILED DESCRIPTION OF THE INVENTION

The present invention relates to improved G-rich oligonucleotide (GRO) aptamers specific to nucleolin, a method of preparing the aptamers and a use of the aptamers for diagnosing and/or treating a cancer.

GRO29A (TTTGGTGGTGGTGGTTGTGGTGGTGGTGG; SEQ ID NO: 1) and AS1411 (GGTGGTGGTGGTTGTGGTGGTGGTGG; SEQ ID NO: 2) are G-rich oligonucleotide (GRO) aptamers comprising a single-strand DNA chain of 29 or 26 bases with unmodified phosphodiester linkages. G-rich oligonucleotide (GROs) are a class of non-antisense nucleic acids that exhibit potent anti-proliferative effects against almost every cancer cell type that was tested and thus, appears to have broad therapeutic potential. GRO29A and AS1411 have been known to bind to the nucleolin protein, which is expressed at elevated levels in transformed cells. Almost all tumor cells have been shown to present nucleolin on the cell surface as well as expressing it in the cytoplasm and nucleus. Nucleolin plays multiple roles in the cell and is involved in ribosome biogenesis, cell growth and DNA replication. The mechanism of GRO anti-proliferative activity appears to depend on their binding to the nucleolin protein.

GRO29A and AS1411 self-anneal to form a biomolecular quadruplex structure that is extremely stable and resistant to degradation by serum enzyme. GRO29A and AS1411 have shown activity against a wide range of solid and blood cancer cell lines in preclinical experiments and could therefore have potential against a variety of human cancers.

The inventors directly applied chemically modified pyrimidine-based nucleoside(s) (e.g., deoxyuridine (dU), deoxycytidine (dC), uridine (U), cytidine (C), etc.) into the GRO aptamers (AS1411and GRO29A), which binds to nucleolin protein expressed in abnormally hyperproliferative cells, such as cancer cells, to find a type of GRO aptamer more capable of specific binding to abnormally hyperproliferative cells, such as cancer cells. The modified nucleoside may be a pyrimidine nucleoside modified by a hydrophobic group, such as benzyl group, a naphthyl group, or a pyrrolebenzyl group, at its 5 position. Modified nucleoside may be exemplified as 5-(N-benzylcarboxyamide) -2'-deoxyuridine (called BzdU), 5-(N-naphthylcarboxyamide)-2'-deoxyuridine (called NapdU), 5-(N-4-pyrrolebenzylcarboxyamide)-2'-deoxyuridine(called 4-PBdU), 5-(N- benzylcarboxyamide)-2'-deoxycytidine (called BzdC), 5-(N-naphthylcarboxyamide) -2'-deoxycytidine (called NapdC), 5-(N-4-pyrrolebenzylcarboxyamide) -2'-deoxycytidine (called 4-PBdC), 5-(N-benzylcarboxyamide) -2'-uridine (called BzU), 5-(N-naphthylcarboxyamide)-2'-uridine (called NapU), 5-(N-4-pyrrolebenzylcarboxyamide)-2'-uridine(called 4-PBU), 5-(N-benzylcarboxyamide)-2'-cytidine (called BzC), 5-(N-napthylcarboxyamide)-2'- cytidine (called NapC), 5-(N-4-pyrrolebenzylcarboxyamide)-2'-cytidine (called 4-PBC), and the like.

In the concrete embodiment, several hundred compounds of GRO aptamer (AS1411 and GRO29A)-containing modified dU such as BzdU, NapdU and 4-PBdU (BzdU-containing-, NapdU-containing- and 4-PBdU-containing GRO aptamer) were exemplarily synthesized by randomly substituting one to twelve thymidines(T) in GRO29A (SEQ ID NO: 1) and one to nine thymidine in AS1411 (SEQ ID NO: 2) with modified dUs. The modified pyrimidine nucleoside having a hydrophobic group, such as benzyl group, a naphthyl group, or a pyrrolebenzyl group, at its 5 position can be sufficiently exemplified by the modified dUs as described above. Several statistically quantified fluorescence measurement, qualified confocal imaging analysis, FACS analysis, and MTT assay demonstrated with replaced T by modified dUs of a particular position of GRO aptamers (AS1411 and GRO29A). The results show that the modified dU-containing GRO aptamers significantly increased the targeting affinity to various cell lines, implying that the position and number of substituents in GRO aptamers (AS1411and GRO29A) are critical parameters to improve the aptamer function. In the present invention, it is revealed that chemical modification on the existing aptamers would enhance the binding and targeting affinity to targets of interest without additional SELEX procedure.

The inventors also found that AS1411, which is a modified form of GRO29A by deletion of 'TTT' present at 5' end of GRO29A, has similar or higher affinity to nucleolin compared to GRO29A, indicating that the three bases present at 5' end of GRO29A (SEQ ID NO: 1) play no important role in the affinity to nucleolin. Therefore, the sequence and/or presence/absence of the three bases may not matter in the present invention, and thus following SEQ ID NO: 3 can also be included in the present invention:

```
NGGTGGTGGTGGTTGTGGTGGTGGTGGN    (SEQ ID NO: 3)
``` wherein 'N' may be absent or 1 to 20 nucleosides, preferably 1 to 10 nucleosides, which is independently selected from the group consisting of adenosine (A), thymidine (T)/uridine (U), cytidine (C), and guanosine (G).

Hereinafter, the present invention is described in detail.

In an aspect, a nucleolin-specific aptamer is provided. As used herein, 'nucleolin-specific aptamer' means an aptamer having a specifically high affinity to nucleolin protein, thereby being capable of specifically binding to nucleolin protein.

The aptamer has the nucleotide sequence of SEQ ID NO: 3, preferably SEQ ID NO: 1 or 2, wherein one or more thymidines (T) are independently substituted with a modified pyrimidine nucleoside (e.g., deoxyuridine (dU), deoxycytidine (dC), uridine (U), cytidine (C), etc.). The modified pyrimidine nucleoside may be a pyrimidine nucleoside having a hydrophobic group at 5 position. The hydrophobic group may have a benzyl group, a naphthyl group, or a pyrrolebenzyl group. By such modification of pyrimidine nucleoside with a hydrophobic group, the affinity of the aptamer to nucleolin is considerably improved compared with that of non-modified aptamer.

In a concrete embodiment, the hydrophobic group may be benzylcarboxyamide, naphthylcarboxyamide, pyrrolebenzylcarboxyamide and the like, and accordingly, the modified pyrimidine nucleoside may be 5-(N-benzylcarboxyamide)-2'-deoxyuridine (called BzdU), 5-(N-naphthylcarboxyamide)-2'-deoxyuridine (called NapdU), 5-(N-4-pyrrolebenzylcarboxyamide)-2'-deoxyuridine (called 4-PBdU), 5-(N-benzylcarboxyamide)-2'-deoxycytidine (called BzdC), 5-(N-naphthylcarboxyamide)-2'-deoxycytidine (called NapdC), 5-(N-4-pyrrolebenzylcarboxyamide)-2'-deoxycytidine (called 4-PBdC), 5-(N-benzylcarboxyamide)-2'-uridine (called BzU), 5-(N-naphthylcarboxyamide)-2'-uridine (called NapU), 5-(N-4-pyrrolebenzylcarboxyamide)-2'-uridine (called 4-PBU), 5-(N-benzylcarboxyamide)-2'-cytidine (called BzC), 5-(N-naphthylcarboxyamide)-2'-cytidine (called NapC), 5-(N-4-pyrrolebenzylcarboxyamide)-2'-cytidine (called 4-PBC), and the like.

The inventors found that the position of thymidine to be modified is also important to improve the affinity to nucleolin. The modification of thymidines present at central region of the aptamer considerably contributes to improve the affinity to nucleolin. The central region may be a loop site of the aptamer. More specifically, the central region may be $12^{th}$ to $18^{th}$ positions, preferably $15^{th}$ and $16^{th}$ positions of SEQ ID NO: 1, or $9^{th}$ to $18^{th}$ positions, preferably $12^{th}$ and $13^{th}$ positions of SEQ ID NO: 2 or SEQ ID NO: 3 (when the positions are counted starting from 'G' after 'N' at 5'-end). As shown in FIG. 23, it is found that a more modification on any position in addition to central double modified dU-containing GRO29A or AS1411 did not increase binding to nucleolin on various cancer cell lines, indicating that the central region (2 bases) of the aptamer may be a critical region for the modification of the aptamer to effect on the affinity of the aptamer to nucleolin.

Therefore, in a preferable embodiment, at least two thymidines present in $12^{th}$ to $18^{th}$ positions, preferably at $15^{th}$ and $16^{th}$ positions of SEQ ID NO: 1, or present in $9^{th}$ to $18^{th}$ positions, preferably at $12^{th}$ and $13^{th}$ positions of SEQ ID NO: 2 or SEQ ID NO: 3 (when the positions are counted starting from 'G' after 'N' at 5'-end) are substituted with the modified deoxyuridine. In a concrete embodiment, the aptamer has the nucleotide sequence of SEQ ID NO: 1, wherein 2 to 12 thymidines essentially comprising two thymidines present in $12^{th}$ to $18^{th}$ positions, preferably at $15^{th}$ and $16^{th}$ positions are replaced with modified deoxyuridines. In another concrete embodiment, the aptamer has the nucleotide sequence of SEQ ID NO: 2 or SEQ ID NO: 3 (when the positions are counted starting from 'G' after 'N' at 5'-end), wherein 2 to 9 thymidines essentially comprising two thymidines present in $9^{th}$ to $18^{th}$ positions, preferably at $12^{th}$ and $13^{th}$ positions are replaced with modified deoxyuridines.

In another aspect, a method of preparing the nucleolin-specific aptamer according to the present invention is provided. The method may comprise the steps of replacing one or more thymidines (T) present in the nucleotide sequence of SEQ ID NO: 1 or 2 with the modified pyrimidine nucleoside (s) (e.g., dU, dC, U, C, etc.) as described above.

Nucleolin functions as a marker of hyper-proliferative cells, such as cancer cells, since nucleolin is specifically expressed on surface of hyper-proliferative cells, such as cancer cells. Therefore, the nucleolin-specific aptamer according to the present invention can be useful in diagnosing various hyper-proliferative cell disorders.

As used herein, the hyper-proliferative cell disorder refers to excess (abnormally high) cell proliferation (abnormal hyper-proliferation of cell), relative to that occurring with the same type of cell in the general population and/or the same type of cell obtained from a patient at an earlier time. The term denotes malignant as well as non-malignant cell populations. Such disorders have an excess cell proliferation of one or more subsets of cells, which often appear to differ from the surrounding tissue both morphologically and genotypically. The excess cell proliferation can be determined by reference to the general population and/or by reference to a particular patient, e.g. at an earlier point in the individual's life. Hyperproliferative cell disorders can occur in different types of animals and in humans, and produce different physical manifestations depending upon the affected cells. The hyper-proliferative cell disorders may include various cancers.

Therefore, in another aspect, a method of diagnosing a hyper-proliferative cell disorder, such as a cancer, using the nucleolin-specific aptamer according to the present invention is provided. The method may comprise the steps of:

contacting the nucleolin-specific aptamer with a sample from a subject, wherein the aptamer is labeled with a detectable label; and detecting a signal from the label.

In the method, the subject is determined as having a hyper-proliferative cell disorder, such as a cancer, when the signal is detected. The nucleolin specific aptamer is as described above.

The subject to be diagnosed may be from any mammalian species, e.g. primate sp., particularly humans; rodents including mice, rats and hamsters; rabbits; equines, bovines, canines, felines; and the like. Animal models may be of interest for experimental investigations, providing a model for treatment of human disease. The sample may be any bio-sample from the subject, such as cells, tissues, blood, body fluid, and the like.

The cancer that can be diagnosed by the present invention may be any nucleolin-associated cancer including any solid cancers and blood cancers, including leukemias, lymphomas (Hodgkins and non-Hodgkins), and other myeloproliferative disorders; carcinomas of solid tissue, sarcomas, melanomas, adenomas, hypoxic tumors, squamous cell carcinomas of the mouth, throat, larynx, or lung, genitourinary cancers such as cervical and bladder cancer, hematopoietic cancers, head and neck cancers, and nervous system cancers, benign lesions such as papillomas, and the like. The nucleolin-associated cancer may be selected from the group consisting of leukemia, lymphoma, breast cancer, liver cancer, gastric cancer, ovarian carcinoma, cervical carcinoma, glioma cancer, colon cancer, lung cancer, pancreas cancer, prostate cancer, liver cancer, stomach cancer, uterine cancer, bladder cancer, thyroid cancer, ovary cancer, melanoma cancer, cervical cancer, and the like, but not be limited thereto.

The label may be any one which can be detectable by any conventional means. For example, the label may be one or more selected from the group consisting of a fluorescence material, infrared material, quantum dots, ion oxide bead, PET probe (e.g., $^{68}$gallium), T1 MR probe including iron oxide (e.g., $Fe_3O_4$), T2 MR probe (e.g., $MnFe_2O_4$, or $GdFe_2O_4$ nanoparticles), and the like, but not be limited thereto.

When the labeled-nucleolin specific aptamer is contacted with the sample, and then, non-reacted aptamer is removed (for example, by washing), if nucleolin is present in the sample (i.e., the subject having abnormally hyper-proliferative cells, such as cancer cells, resulted from the presence of nucleolin), the aptamer specifically binds to nucleolin on cells, and the signal from the label attached to the aptaemer is detected, allowing to diagnose a hyper-proliferative cell disease, such as a cancer, as described above.

Nucleolin is associated with cell cycle and cell division, and thus, when the nucleolin specific aptamer of the present invention binds to nucleolin, thereby interfering with the function of nucleolin, resulting in interfering with the cell cycle, arresting cell-cycle, for example at the S-phase, inhibiting DNA replication, inducing cell death, etc. Therefore, the nucleolin specific aptamer of the present invention can function as an inhibitor of nucleolin, and agent for inhibiting hyperproliferation of cell, and thereby being useful in treating a hyper-proliferative cell disease, such as cancer, as described above.

Therefore, in another aspect, a method of inhibiting nucleolin using the nucleolin-specific aptamer is provided. The method may comprise the step of administering the nucleolin-specific aptamer according to the present invention to a subject or a sample comprising nucleolin-expressing cells. In addition, a method of inhibiting hyperproliferation of cell cased by nucleolin using the nucleolin-specific aptamer is also provided. The method may comprise the step of administering the nucleolin-specific aptamer of claim 1 to a subject or a sample comprising nucleolin-expressing cells.

The nucleolin-specific aptamer is as described above. The subject may be from any mammalian species, e.g. primate sp., particularly humans; rodents including mice, rats and hamsters; rabbits; equines, bovines, canines, felines; and the like, who is in need of the inhibition of nucleolin and/or hyper-priliferation of cell caused by nucleolin. Animal models may be of interest for experimental investigations, providing a model for treatment of human disease. The sample may be any bio-sample from the subject, such as cells, tissues, blood, body fluid, and the like.

In another aspect, a method of inhibiting an abnormal hyper-proliferation of cell using the nucleolin-specific aptamer according to the present invention is provided. In addition, a method of treating a hyper-proliferative cell disorder, such as a cancer (nucleolin-associated cancer) using the nucleolin-specific aptamer according to the present invention is also provided.

The method may comprise the step of administering an effective amount of the nucleolin-specific aptamer to a subject who needs the inhibition of the abnormal hyper-proliferation of cell and/or the treatment of the abnormal hyper-proliferation of cell, for example, the treatment of a cancer. As described above, the nucleolin-specific aptamer has an excellent affinity to nucleolin to inhibit nucleolin, thereby exhibiting a treatment effect for cell hyper-proliferation, such as a cancer.

The nucleolin specific aptamer is as described above. The subject may be from any mammalian species, e.g. primate sp., particularly humans; rodents including mice, rats and hamsters; rabbits; equines, bovines, canines, felines; and the like, who needs the inhibition of the abnormal hyper-proliferation of cell and/or the treatment of the abnormal hyper-proliferation of cell, for example, the treatment of a cancer. Animal models may be of interest for experimental investigations, providing a model for treatment of human disease. The cancer that can be treated by the present invention may be any nucleolin-associated cancer including any solid cancers and blood cancers, including leukemias, lymphomas (Hodgkins and non-Hodgkins), and other myeloproliferative disorders; carcinomas of solid tissue, sarcomas, melanomas, adenomas, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, and the like. The nucleolin-associated cancer may be selected from the group consisting of leukemia, lymphoma, breast cancer, liver cancer, gastric cancer, ovarian carcinoma, cervical carcinoma, glioma cancer, colon cancer, lung cancer, pancreas cancer, prostate cancer, liver cancer, stomach cancer, uterine cancer, bladder cancer, thyroid cancer, ovary cancer, melanoma cancer, cervical cancer, and the like, but not be limited thereto.

The effective amount means an amount exhibiting a therapeutic effect on the inhibition of nucleolin or hyper-proliferation of cell, for example treating a cancer, and may be properly controlled depending on the condition of the subject and/or severity of disease. The effective amount can be administered in one or more administrations. The administration may be performed by oral or parenteral (e.g., intravenous, subcutaneous, intramuscular, and the like) pathway, but not limited thereto.

In still another aspect, a pharmaceutical composition containing the nucleolin-specific aptamer according to the present invention as an active ingredient is provided. The pharmaceutical composition may a nucleolin inhibitor or agent for inhibiting an abnormal hyper-proliferation of cell, for example an anticancer agent.

EXAMPLES

A better understanding of the present invention may be obtained in light of the following examples that are set forth to illustrate, but are not to be construed to limit, the present invention.

Example 1

Figure 1:
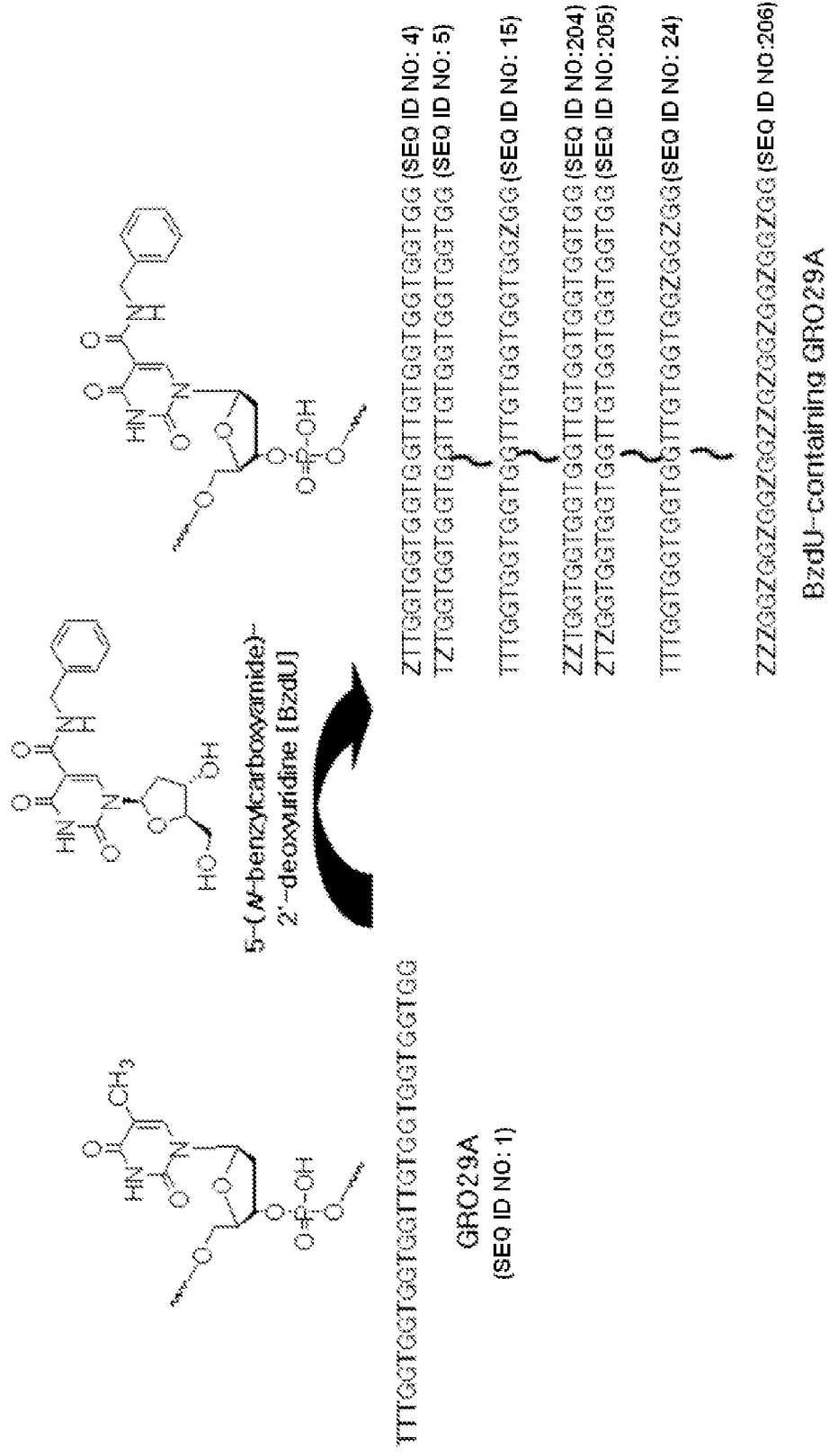
FIG. 1 shows a schematic diagram to synthesize nucleolin aptamer containing 5-(N-benzylcarboxyamide)-2'-deoxyuridine (BzdU-containing GRO29A), wherein Z indicates that thymidines in GRO29A oligonucleotides were substituted with 5-(N-benzylcarboxyamide)-2'-deoxyuridine (BzdU).

Preparation of Cy3-Labeled Modified dU AS1411 and GRO29A 1.1: Design of Cy3-Labeled Modified dU AS1411 and GRO29A Forty-seven different compounds of Cy3-labeled BzdU-containing GRO29A were designed and synthesized. The GRO29A oligonucleotides (TTTGGTGGTGGTGGT-TGTGGTGGTGGTGG, SEQ ID NO: 1) incorporated with 5-(N-benzylcarboxyamide)-2'-deoxyuridine (BzdU) and labeled with Cy3 were prepared according to the following synthesis procedure of Example 1.2. One to twelve thymidines in GRO29A oligonucleotides were randomly replaced with BzdU (see FIG. 1). FIG. 1 is a schematic diagram to synthesize nucleolin aptamer containing 5-(N-benzylcarboxyamide)-2'-deoxyuridine (BzdU-containing GRO29A), wherein Z indicated where thymidines in GRO29A oligonucleotides were substituted with 5-(N-benzylcarboxyamide)-2'-deoxyuridine (BzdU).

The designed forty-seven Cy3-labeled BzdU-containing GRO29A are summarized in Table 1.

TABLE 1

A list of modified GRO29A containing Bz at 5 position of dU (5-(N-benzylcarboxyamide)-2'-deoxyuridine, BzdU)

| Comp. No. | Cy3-labeled Modified dU-GRO29A Sequence (5'→3') | Cal. MS | Obs. MS |
| --- | --- | --- | --- |
| Cy3-1642-8 | Cy3-labeled-ZTTGGTGGTGGTGGTTGTGGTGGTGGTGG (SEQ ID NO: 4) | 9811.71 | 9812.32 |
| Cy3-1642-9 | Cy3-labeled-TZTGGTGGTGGTGGTTGTGGTGGTGGTGG (SEQ ID NO: 5) | 9811.71 | 9811.72 |
| Cy3-1642-10 | Cy3-labeled-TTZGGTGGTGGTGGTTGTGGTGGTGGTGG (SEQ ID NO: 6) | 9811.71 | 9811.92 |
| Cy3-1642-11 | Cy3-labeled-TTTGGZGGTGGTGGTTGTGGTGGTGGTGG (SEQ ID NO: 7) | 9811.71 | 9812.27 |
| Cy3-1642-12 | Cy3-labeled-TTTGGTGGZGGTGGTTGTGGTGGTGGTGG (SEQ ID NO: 8) | 9811.71 | 9811.83 |
| Cy3-1642-13 | Cy3-labeled-TTTGGTGGTGGZGGTTGTGGTGGTGGTGG (SEQ ID NO: 9) | 9811.71 | 9812.38 |
| Cy3-1642-14 | Cy3-labeled-TTTGGTGGTGGTGGZTGTGGTGGTGGTGG (SEQ ID NO: 10) | 9811.71 | 9812.18 |
| Cy3-1642-15 | Cy3-labeled-TTTGGTGGTGGTGGTZGTGGTGGTGGTGG (SEQ ID NO: 11) | 9811.71 | 9812.22 |
| Cy3-1642-16 | Cy3-labeled-TTTGGTGGTGGTGGTTGZGGTGGTGGTGG (SEQ ID NO: 12) | 9811.71 | 9812.01 |
| Cy3-1642-17 | Cy3-labeled-TTTGGTGGTGGTGGTTGTGGZGGTGGTGG (SEQ ID NO: 13) | 9811.71 | 9812.10 |
| Cy3-1642-18 | Cy3-labeled-TTTGGTGGTGGTGGTTGTGGTGGZGGTGG (SEQ ID NO: 14) | 9811.71 | 9812.69 |
| Cy3-1642-19 | Cy3-labeled-TTTGGTGGTGGTGGTTGTGGTGGTGGZGG (SEQ ID NO: 15) | 9811.71 | 9811.78 |
| Cy3-1642-21 | Cy3-labeled-TZZGGTGGTGGTGGTTGTGGTGGTGGTGG (SEQ ID NO: 16) | 9930.82 | 9931.40 |
| Cy3-1642-23 | Cy3-labeled-ZZZGGTGGTGGTGGTTGTGGTGGTGGTGG (SEQ ID NO: 17) | 9930.82 | 9931.24 |
| Cy3-1642-24 | Cy3-labeled-TTTGGTGGTGGTGGTTGTGGTGGZGGZGG (SEQ ID NO: 18) | 9930.82 | 9931.02 |
| Cy3-1642-25 | Cy3-labeled-TTTGGTGGTGGTGGTTGTGGZGGTGGZGG (SEQ ID NO: 19) | 9930.82 | 9931.10 |
| Cy3-1642-26 | Cy3-labeled-TTTGGTGGTGGTGGTTGZGGTGGTGGZGG (SEQ ID NO: 20) | 9930.82 | 9931.81 |
| Cy3-1642-27 | Cy3-labeled-TTTGGTGGTGGTGGTZGTGGTGGTGGZGG (SEQ ID NO: 21) | 9930.82 | 9930.93 |
| Cy3-1642-28 | Cy3-labeled-TTTGGTGGTGGTGGZTGTGGTGGTGGZGG (SEQ ID NO: 22) | 9930.82 | |
| Cy3-1642-29 | Cy3-labeled-TTTGGTGGTGGZGGTTGTGGTGGTGGZGG (SEQ ID NO: 23) | 9930.82 | |
| Cy3-1642-30 | Cy3-labeled-TTTGGTGGZGGTGGTTGTGGTGGTGGZGG (SEQ ID NO: 24) | 9930.82 | |
| Cy3-1642-31 | Cy3-labeled-TTTGGZGGTGGTGGTTGTGGTGGTGGZGG (SEQ ID NO: 25) | 9930.82 | 9931.81 |
| Cy3-1642-32 | Cy3-labeled-TTZGGTGGTGGTGGTTGTGGTGGTGGZGG (SEQ ID NO: 26) | 9930.82 | |
| Cy3-1642-33 | Cy3-labeled-TZTGGTGGTGGTGGTTGTGGTGGTGGZGG (SEQ ID NO: 27) | 9930.82 | |
| Cy3-1642-34 | Cy3-labeled-ZTTGGTGGTGGTGGTTGTGGTGGTGGZGG (SEQ ID NO: 28) | 9930.82 | |

TABLE 1-continued

A list of modified GRO29A containing Bz at 5 position of dU (5-(N-benzylcarboxyamide)-2'-deoxyuridine, BzdU)

| Comp. No. | Cy3-labeled Modified dU-GRO29 Sequence (5'→3') | Cal. MS | Obs. MS |
|---|---|---|---|
| Cy3-1642-35 | Cy3-labeled-TTTGGTGGTGGTGGZZGTGGTGGTGGZGG (SEQ ID NO: 29) | 10049.93 | |
| Cy3-1642-36 | Cy3-labeled-TZZGGTGGTGGTGGTTGTGGTGGTGGZGG (SEQ ID NO: 30) | 10049.93 | |
| Cy3-1642-37 | Cy3-labeled-ZZTGGTGGTGGTGGTTGTGGTGGTGGZGG (SEQ ID NO: 31) | 10049.93 | 10051.40 |
| Cy3-1642-39 | Cy3-labeled-TTTGGTGGTGGTGGZZGTGGTGGTGGTGG (SEQ ID NO: 32) | 9930.82 | |
| Cy3-1642-40 | Cy3-labeled-TTTGGTGGTGGTGGZZGZGGTGGTGGTGG (SEQ ID NO: 33) | 10049.93 | |
| Cy3-1642-41 | Cy3-labeled-TTTGGTGGTGGTGGZZGTGGZGGTGGTGG (SEQ ID NO: 34) | 10049.93 | |
| Cy3-1642-42 | Cy3-labeled-TTTGGTGGTGGTGGZZGTGGTGGZGGTGG (SEQ ID NO: 35) | 10049.93 | |
| Cy3-1642-43 | Cy3-labeled-TTTGGTGGTGGZGGZZGTGGTGGTGGTGG (SEQ ID NO: 36) | 10049.93 | |
| Cy3-1642-44 | Cy3-labeled-TTTGGTGGZGGTGGZZGTGGTGGTGGTGG (SEQ ID NO: 37) | 10049.93 | |
| Cy3-1642-45 | Cy3-labeled-TTTGGZGGTGGTGGZZGTGGTGGTGGTGG (SEQ ID NO: 38) | 10049.93 | 10050.99 |
| Cy3-1642-46 | Cy3-labeled-TTZGGTGGTGGTGGZZGTGGTGGTGGTGG (SEQ ID NO: 39) | 10049.93 | |
| Cy3-1642-47 | Cy3-labeled-TZTGGTGGTGGTGGZZGTGGTGGTGGTGG (SEQ ID NO: 40) | 10049.93 | |
| Cy3-1642-48 | Cy3-labeled-ZTTGGTGGTGGTGGZZGTGGTGGTGGTGG (SEQ ID NO: 41) | 10049.93 | |
| Cy3-1642-49 | Cy3-labeled-TZZGGTGGTGGTGGZZGTGGTGGTGGTGG (SEQ ID NO: 42) | 10169.04 | |
| Cy3-1642-50 | Cy3-labeled-ZZTGGTGGTGGTGGZZGTGGTGGTGGTGG (SEQ ID NO: 43) | 10169.04 | |
| Cy3-1642-51 | Cy3-labeled-ZTZGGTGGTGGTGGZZGTGGTGGTGGTGG (SEQ ID NO: 44) | 10169.04 | |
| Cy3-1642-52 | Cy3-labeled-ZZZGGTGGTGGTGGZZGTGGTGGTGGTGG (SEQ ID NO: 45) | 10288.15 | 10288.41 |
| Cy3-1642-53 | Cy3-labeled-TTTGGTGGTGGZGGTTGZGGTGGTGGTGG (SEQ ID NO: 46) | 9930.82 | |
| Cy3-1642-54 | Cy3-labeled-TTTGGTGGZGGTGGTTGTGGZGGTGGTGG (SEQ ID NO: 47) | 9930.82 | |
| Cy3-1642-55 | Cy3-labeled-TTTGGZGGTGGTGGTTGTGGTGGZGGTGG (SEQ ID NO: 48) | 9930.82 | |
| Cy3-1642-56 | Cy3-labeled-TTTGGTGGZGGZGGTTGZGGZGGZGGTGG (SEQ ID NO: 49) | 10288.15 | |
| Cy3-1642-57 | Cy3-labeled-TTTGGZGGZGGZGGTTGZGGZGGTGGZGG (SEQ ID NO: 50) | 10407.26 | |
| Cy3-1641-3(GRO29A) | Cy3-labeled-TTTGGTGGTGGTGGTTGTGGTGGTGGTGG (SEQ ID NO: 1) | 9692.60 | 9693.85 |
| Cy3-1641-8(CRO29A) | Cy3-labeled-TTTCCTCCTCCTCCTTCTCCTCCTCCTCC (SEQ ID NO: 51) | 9012.09 | 9012.70 |

Z: BzdU

Cy3-labeled BzdU-containing GRO29A derivatives contained 5-(N-benzylcarboxyamide)-2'-deoxyuridine (BzdU) in Z. CRO29A indicated the control form of GRO29A, wherein all 'G's in GRO29A are substituted with 'C'.

The GRO29A oligonucleotides incorporated with 5-(N-napthylcarboxyamide)-2'-deoxyuridine (NapdU) instead of BzdU and labeled with Cy3 were also designed (see Table 2), and prepared according to the following synthesis procedure of Example 1.2.

TABLE 2

A list of modified GRO29A containing Nap at 5 position of dU (5-(N-naphthylcarboxyamide)-2'-deoxyuridine, NapdU)

| Comp. No. | Cy3-labeled Modified dU-GRO29A Sequence (5'→3') | MS |
|---|---|---|
| 1642-59 | TTTGGZGGTGGTGGTTGTGGTGGTGGTGG (SEQ ID NO: 53) | 9861.77 |
| 1642-60' | TTTGGTGGZGGTGGTTGTGGTGGTGGTGG (SEQ ID NO: 54) | 9861.77 |
| 1642-61 | TTTGGTGGTGGZGGTTGTGGTGGTGGTGG (SEQ ID NO: 55) | 9861.77 |
| 1642-62 | TTTGGTGGTGGTGGTTGTGGTGGTGGZGG (SEQ ID NO: 56) | 9861.77 |
| 1642-63 | TTTGGTGGZGGTGGTTGTGGTGGTGGZGG (SEQ ID NO: 57) | 10030.94 |
| 1642-64 | TTTGGZGGTGGTGGTTGTGGTGGTGGZGG (SEQ ID NO: 58) | 10030.94 |
| 1642-65 | ZZTGGTGGTGGTGGTTGTGGTGGTGGZGG (SEQ ID NO: 59) | 10220.11 |
| 1642-66 | TTTGGTGGTGGTGGZZGTGGTGGTGGTGG (SEQ ID NO: 60) | 10030.94 |
| 1642-68 | TTTGGTGGTGGTGGZZGZGGTGGTGGTGG (SEQ ID NO: 61) | 10200.11 |
| 1642-67 | TTTGGTGGTGGTGGZZGTGGZGGTGGTGG (SEQ ID NO: 62) | 10200.11 |
| 1642-69 | TZTGGTGGTGGTGGZZGTGGTGGTGGTGG (SEQ ID NO: 63) | 10200.11 |
| 1642-70 | ZTTGGTGGTGGTGGZZGTGGTGGTGGTGG (SEQ ID NO: 64) | 10200.11 |
| 1642-71 | TZZGGTGGTGGTGGZZGTGGTGGTGGTGG (SEQ ID NO: 65) | 10369.28 |
| 1642-72 | ZTZGGTGGTGGTGGZZGTGGTGGTGGTGG (SEQ ID NO: 66) | 10369.28 |
| 1642-73 | ZZZGGTGGTGGTGGZZGTGGTGGTGGTGG (SEQ ID NO: 67) | 10538.45 |
| 1642-74 | TTTGGZGGZGGZGGTTGZGGZGGTGGZGG (SEQ ID NO: 68) | 10707.62 |
| GRO29A | TTTGGTGGTGGTGGTTGTGGTGGTGGTGG (SEQ ID NO: 1) | 9692.6 |
| CRO29A | TTTCCTCCTCCTCCTTCTCCTCCTCCTCC (SEQ ID NO: 51) | 9012.09 |

Z = NapdU

Cy3-labeled NapdU-containing GRO29A derivatives contained 5-(N-napthylcarboxyamide)-2'-deoxyuridine (NapdU) in Z. CRO29A indicated the control form of GRO29A, wherein all 'G's in GRO29A are substituted with 'C'.

Modified dU-containing AS1411 derivatives were also designed and synthesized by randomly substituting one to nine thymidine (T) in AS1411 (GGTGGTGGTGGTTGTGGTGGTGG, SEQ ID NO: 2). Modified dU inserting on AS1411 is independently selected from 5-(N-benzylcorboxyamide)-2'-deoxyuridine[BzdU] and 5-(N-naphthylcarboxyamide)-2'-deoxyuridine[NapdU] and 5-(N-4-pyrrimidylbenzylcarboxyamide)-2'-deoxyuridine[4-PBdU]. The modified dU-containing AS1411 derivatives were summarized in Tables 3-5.

TABLE 3

A list of modified AS1411 having hydrophobic groups such as Bz at 5 position of dU (5-(N-benzylcarboxyamide)-2'-deoxyuridine, BzdU)

| Comp. No. | Cy3-labeled Modified dU-AS1411 sequence | MS |
| --- | --- | --- |
| Cy3-1642-88 | Cy3-GGZGGZGGZGGZZGZGGZGGZGGZGG (SEQ ID NO: 69) | 9851.99 |
| Cy3-1642-89 | Cy3-GGZGGZGGZGGTTGTGGZGGZGGZGG (SEQ ID NO: 70) | 9494.66 |
| Cy3-1642-90 | Cy3-GGZGGZGGTGGTTGTGGTGGZGGZGG (SEQ ID NO: 71) | 9256.44 |
| Cy3-1642-91 | Cy3-GGTGGZGGZGGTTGTGGZGGZGGTGG (SEQ ID NO: 72) | 9256.44 |
| Cy3-1642-92 | Cy3-GGZGGTGGTGGTTGTGGTGGTGGZGG (SEQ ID NO: 73) | 9018.22 |
| Cy3-1642-93 | Cy3-GGTGGZGGTGGTTGTGGTGGZGGTGG (SEQ ID NO: 74) | 9018.22 |
| Cy3-1642-94 | Cy3-GGTGGTGGZGGTTGTGGZGGTGGTGG (SEQ ID NO: 75) | 9018.22 |
| Cy3-1642-95 | Cy3-GGZGGTGGZGGTTGTGGZGGTGGZGG (SEQ ID NO: 76) | 9256.44 |
| Cy3-1642-96 | Cy3-GGTGGTGGTGGTZGTGGTGGTGGTGG (SEQ ID NO: 77) | 8899.11 |
| Cy3-1642-97 | Cy3-GGTGGTGGTGGZZGZGGTGGTGGTGG (SEQ ID NO: 78) | 9137.33 |
| Cy3-1642-98 | Cy3-GGTGGTGGTGGZTGZGGTGGTGGTGG (SEQ ID NO: 79) | 9018.22 |
| Cy3-1642-82 | Cy3-GGZGGTGGTGGTTGTGGTGGTGGTGG (SEQ ID NO: 80) | 8899.11 |
| Cy3-1642-99 | Cy3-GGTGGZGGTGGTTGTGGTGGTGGTGG (SEQ ID NO: 81) | 8899.11 |
| Cy3-1642-100 | Cy3-GGTGGTGGZGGTTGTGGTGGTGGTGG (SEQ ID NO: 82) | 8899.11 |
| Cy3-1642-101 | Cy3-GGTGGTGGTGGZTGTGGTGGTGGTGG (SEQ ID NO: 83) | 8899.11 |
| Cy3-1642-102 | Cy3-GGTGGTGGTGGTZGTGGTGGTGGTGG (SEQ ID NO: 84) | 8899.11 |
| Cy3-1642-103 | Cy3-GGTGGTGGTGGTTGZGGTGGTGGTGG (SEQ ID NO: 85) | 8899.11 |
| Cy3-1642-104 | Cy3-GGTGGTGGTGGTTGTGGZGGTGGTGG (SEQ ID NO: 86) | 8899.11 |
| Cy3-1642-105 | Cy3-GGTGGTGGTGGTTGTGGTGGZGGTGG (SEQ ID NO: 87) | 8899.11 |
| Cy3-1642-83 | Cy3-GGTGGTGGTGGTTGTGGTGGTGGZGG (SEQ ID NO: 88) | 8899.11 |
| Cy3-1642-106 | Cy3-GGTGGTGGTGGTTGTGGTGGZGGZGG (SEQ ID NO: 89) | 9018.22 |
| Cy3-1642-107 | Cy3-GGTGGTGGTGGTTGTGGZGGTGGZGG (SEQ ID NO: 90) | 9018.22 |
| Cy3-1642-108 | Cy3-GGTGGTGGTGGTTGZGGTGGTGGZGG (SEQ ID NO: 91) | 9018.22 |
| Cy3-1642-109 | Cy3-GGTGGTGGTGGTZGTGGTGGTGGZGG (SEQ ID NO: 92) | 9018.22 |
| Cy3-1642-110 | Cy3-GGTGGTGGTGGZTGTGGTGGTGGZGG (SEQ ID NO: 93) | 9018.22 |

TABLE 3-continued

A list of modified AS1411 having hydrophobic groups such as Bz at 5 position of dU (5-(N-benzylcarboxyamide)-2'-deoxyuridine, BzdU)

| Comp. No. | Cy3-labeled Modified dU-AS1411 sequence | MS |
| --- | --- | --- |
| Cy3-1642-111 | Cy3-GGTGGTGGZGGTTGTGGTGGTGGZGG (SEQ ID NO: 94) | 9018.22 |
| Cy3-1642-112 | Cy3-GGTGGZGGTGGTTGTGGTGGTGGZGG (SEQ ID NO: 95) | 9018.22 |
| Cy3-1642-113 | Cy3-GGZGGTGGTGGTTGTGGTGGTGGZGG (SEQ ID NO: 96) | 9018.22 |
| Cy3-1642-114 | Cy3-GGTGGTGGTGGZZGTGGTGGTGGZGG (SEQ ID NO: 97) | 9137.33 |
| Cy3-1642-115 | Cy3-GGTGGTGGTGGZZGTGGTGGTGGTGG (SEQ ID NO: 98) | 9018.22 |
| Cy3-1642-116 | Cy3-GGTGGTGGTGGZZGZGGTGGTGGTGG (SEQ ID NO: 99) | 9137.33 |
| Cy3-1642-117 | Cy3-GGTGGTGGTGGZZGTGGZGGTGGTGG (SEQ ID NO: 100) | 9137.33 |
| Cy3-1642-118 | Cy3-GGTGGTGGTGGZZGTGGTGGZGGTGG (SEQ ID NO: 101) | 9137.33 |
| Cy3-1642-119 | Cy3-GGTGGTGGZGGZZGTGGTGGTGGTGG (SEQ ID NO: 102) | 9137.33 |
| Cy3-1642-120 | Cy3-GGTGGZGGTGGZZGTGGTGGTGGTGG (SEQ ID NO: 103) | 9137.33 |
| Cy3-1642-121 | Cy3-GGZGGTGGTGGZZGTGGTGGTGGTGG (SEQ ID NO: 104) | 9137.33 |
| Cy3-1642-122 | Cy3-GGTGGTGGZGGTTGZGGTGGTGGTGG (SEQ ID NO: 105) | 9018.22 |
| Cy3-1642-123 | Cy3-GGTGGZGGTGGTTGTGGZGGTGGTGG (SEQ ID NO: 106) | 9018.22 |
| Cy3-1642-124 | Cy3-GGZGGTGGTGGTTGTGGTGGZGGTGG (SEQ ID NO: 107) | 9018.22 |
| Cy3-1642-125 | Cy3-GGTGGZGGZGGTTGZGGZGGZGGTGG (SEQ ID NO: 108) | 9375.55 |
| Cy3-1642-126 | Cy3-GGZGGZGGZGGTTGZGGZGGTGGZGG (SEQ ID NO: 109) | 9494.66 |
| Cy3-1642-127 | Cy3-ZGGTGGTGGTGGTTGTGGTGGTGGZ (SEQ ID NO: 110) | 9626.62 |
| Cy3-1642-129 | Cy3-CCZCCZCCZCCZZCZCCZCCZCCZCC (SEQ ID NO: 111) | 9171.48 |
| Cy3-1642-130 | Cy3-CCZCCZCCZCCTTCTCCZCCZCCZCC (SEQ ID NO: 112) | 8814.15 |
| Cy3-1642-131 | Cy3-CCTCCTCCTCCZZCZCCTCCTCCTCC (SEQ ID NO: 113) | 8456.82 |
| Cy3-1642-80 (AS1411) | Cy3-GGTGGTGGTGGTTGTGGTGGTGGTGG (SEQ ID NO: 2) | 8780.0 |
| Cy3-1642-81 (Control AS1411) | Cy3-CCTCCTCCTCCTTCTCCTCCTCCTCC (SEQ ID NO: 52) | 8099.49 |

Z = BzdU

Cy3-labeled BzdU-containing AS1411 derivatives contained 5-(N-benzylcarboxyamide)-2'-deoxyuridine (BzdU) in Z. Control AS1411 indicated the control form of AS1411, wherein all 'G's in AS1411 are substituted with 'C'.

TABLE 4

A list of modified AS1411 having hydrophobic groups such as Nap at 5 position of dU (5-(N-naphthylcarboxyamide)-2'-deoxyuridine, NapdU)

| Comp. No. | Cy3-labeled Modified dU-AS1411 sequence | MS |
| --- | --- | --- |
| Cy3-1642-132 | Cy3-GGZGGZGGZGGZZGZGGZGGZGGZGG (SEQ ID NO: 114) | 10302.53 |
| Cy3-1642-133 | Cy3-GGZGGZGGZGGTTGTGGZGGZGGZGG (SEQ ID NO: 115) | 9795.02 |
| Cy3-1642-134 | Cy3-GGZGGZGGTGGTTGTGGTGGZGGZGG (SEQ ID NO: 116) | 9456.68 |
| Cy3-1642-135 | Cy3-GGTGGZGGZGGTTGTGGZGGZGGTGG (SEQ ID NO: 117) | 9456.68 |
| Cy3-1642-136 | Cy3-GGZGGTGGTGGTTGTGGTGGTGGZGG (SEQ ID NO: 118) | 9118.34 |
| Cy3-1642-137 | Cy3-GGTGGZGGTGGTTGTGGTGGZGGTGG (SEQ ID NO: 119) | 9118.34 |
| Cy3-1642-138 | Cy3-GGTGGTGGZGGTTGTGGZGGTGGTGG (SEQ ID NO: 120) | 9118.34 |
| Cy3-1642-139 | Cy3-GGZGGTGGZGGTTGTGGZGGTGGZGG (SEQ ID NO: 121) | 9456.68 |
| Cy3-1642-140 | Cy3-GGTGGTGGTGGTZGTGGTGGTGGTGG (SEQ ID NO: 122) | 8949.17 |
| Cy3-1642-141 | Cy3-GGTGGTGGTGGZZGZGGTGGTGGTGG (SEQ ID NO: 123) | 9287.51 |
| Cy3-1642-142 | Cy3-GGTGGTGGTGGZTGZGGTGGTGGTGG (SEQ ID NO: 124) | 9118.34 |
| Cy3-1642-143 | Cy3-GGZGGTGGTGGTTGTGGTGGTGGTGG (SEQ ID NO: 125) | 8949.17 |
| Cy3-1642-144 | Cy3-GGTGGZGGTGGTTGTGGTGGTGGTGG (SEQ ID NO: 126) | 8949.17 |
| Cy3-1642-145 | Cy3-GGTGGTGGZGGTTGTGGTGGTGGTGG (SEQ ID NO: 127) | 8949.17 |
| Cy3-1642-146 | Cy3-GGTGGTGGTGGZTGTGGTGGTGGTGG (SEQ ID NO: 128) | 8949.17 |
| Cy3-1642-147 | Cy3-GGTGGTGGTGGTZGTGGTGGTGGTGG (SEQ ID NO: 129) | 8949.17 |
| Cy3-1642-148 | Cy3-GGTGGTGGTGGTTGZGGTGGTGGTGG (SEQ ID NO: 130) | 8949.17 |
| Cy3-1642-149 | Cy3-GGTGGTGGTGGTTGTGGZGGTGGTGG (SEQ ID NO: 131) | 8949.17 |
| Cy3-1642-150 | Cy3-GGTGGTGGTGGTTGTGGTGGZGGTGG (SEQ ID NO: 132) | 8949.17 |
| Cy3-1642-151 | Cy3-GGTGGTGGTGGTTGTGGTGGTGGZGG (SEQ ID NO: 133) | 8949.17 |
| Cy3-1642-152 | Cy3-GGTGGTGGTGGTTGTGGTGGZGGZGG (SEQ ID NO: 134) | 9118.34 |
| Cy3-1642-153 | Cy3-GGTGGTGGTGGTTGTGGZGGTGGZGG (SEQ ID NO: 135) | 9118.34 |
| Cy3-1642-154 | Cy3-GGTGGTGGTGGTTGZGGTGGTGGZGG (SEQ ID NO: 136) | 9118.34 |
| Cy3-1642-155 | Cy3-GGTGGTGGTGGTZGTGGTGGTGGZGG (SEQ ID NO: 137) | 9118.34 |
| Cy3-1642-156 | Cy3-GGTGGTGGTGGZTGTGGTGGTGGZGG (SEQ ID NO: 138) | 9118.34 |

TABLE 4-continued

A list of modified AS1411 having hydrophobic groups such as Nap at 5 position of dU (5-(N-naphthylcarboxyamide)-2'-deoxyuridine, NapdU)

| Comp. No. | Cy3-labeled Modified dU-AS1411 sequence | MS |
| --- | --- | --- |
| Cy3-1642-157 | Cy3-GGTGGTGGZGGTTGTGGTGGTGGZGG (SEQ ID NO: 139) | 9118.34 |
| Cy3-1642-158 | Cy3-GGTGGZGGTGGTTGTGGTGGTGGZGG (SEQ ID NO: 140) | 9118.34 |
| Cy3-1642-159 | Cy3-GGZGGTGGTGGTTGTGGTGGTGGZGG (SEQ ID NO: 141) | 9118.34 |
| Cy3-1642-160 | Cy3-GGTGGTGGTGGZZGTGGTGGTGGZGG (SEQ ID NO: 142) | 9287.51 |
| Cy3-1642-161 | Cy3-GGTGGTGGTGGZZGTGGTGGTGGTGG (SEQ ID NO: 143) | 9118.34 |
| Cy3-1642-162 | Cy3-GGTGGTGGTGGZZGZGGTGGTGGTGG (SEQ ID NO: 144) | 9287.51 |
| Cy3-1642-163 | Cy3-GGTGGTGGTGGZZGTGGZGGTGGTGG (SEQ ID NO: 145) | 9287.51 |
| Cy3-1642-164 | Cy3-GGTGGTGGTGGZZGTGGTGGZGGTGG (SEQ ID NO: 146) | 9287.51 |
| Cy3-1642-165 | Cy3-GGTGGTGGZGGZZGTGGTGGTGGTGG (SEQ ID NO: 147) | 9287.51 |
| Cy3-1642-166 | Cy3-GGTGGZGGTGGZZGTGGTGGTGGTGG (SEQ ID NO: 148) | 9287.51 |
| Cy3-1642-167 | Cy3-GGZGGTGGTGGZZGTGGTGGTGGTGG (SEQ ID NO: 149) | 9287.51 |
| Cy3-1642-168 | Cy3-GGTGGTGGZGGTTGZGGTGGTGGTGG (SEQ ID NO: 150) | 9118.34 |
| Cy3-1642-169 | Cy3-GGTGGZGGTGGTTGTGGZGGTGGTGG (SEQ ID NO: 151) | 9118.34 |
| Cy3-1642-170 | Cy3-GGZGGTGGTGGTTGTGGTGGZGGTGG (SEQ ID NO: 152) | 9118.34 |
| Cy3-1642-171 | Cy3-GGTGGZGGZGGTTGZGGZGGZGGTGG (SEQ ID NO: 153) | 9625.85 |
| Cy3-1642-172 | Cy3-GGZGGZGGZGGTTGZGGZGGTGGZGG (SEQ ID NO: 154) | 9795.02 |
| Cy3-1642-173 | Cy3-ZGGTGGTGGTGGTTGTGGTGGTGGZ (SEQ ID NO: 155) | 9726.74 |
| Cy3-1642-174 | Cy3-CCZCCZCCZCCZZCZCCZCCZCCZCC (SEQ ID NO: 156) | 9622.02 |
| Cy3-1642-175 | Cy3-CCZCCZCCZCCTTCTCCZCCZCCZCC (SEQ ID NO: 157) | 9114.51 |
| Cy3-1642-176 | Cy3-CCTCCTCCTCCZZCZCCTCCTCCTCC (SEQ ID NO: 158) | 8607 |

Z = NapdU

TABLE 5

A list of modified AS1411 having hydrophobic
groups such as 4-PB at 5 position of dU (5-(N-4-
pyrrolebenzylcarboxyamide)-2'-deoxyuridine,
4-PBdU)

| Comp. No. | Cy3-labeled Modified dU-AS1411 sequence | MS |
|---|---|---|
| Cy3-1642-177 | Cy3-GGZGGZGGZGGZZGZGGZGGZGGZGG (SEQ ID NO: 159) | 10437.26 |
| Cy3-1642-178 | Cy3-GGZGGZGGZGGTTGTGGZGGZGGZGG (SEQ ID NO: 160) | 9884.84 |
| Cy3-1642-179 | Cy3-GGZGGZGGTGGTTGTGGTGGZGGZGG (SEQ ID NO: 161) | 9516.56 |
| Cy3-1642-180 | Cy3-GGTGGZGGZGGTTGTGGZGGZGGTGG (SEQ ID NO: 162) | 9516.56 |
| Cy3-1642-181 | Cy3-GGZGGTGGTGGTTGTGGTGGTGGZGG (SEQ ID NO: 163) | 9148.28 |
| Cy3-1642-182 | Cy3-GGTGGZGGTGGTTGTGGTGGZGGTGG (SEQ ID NO: 164) | 9148.28 |
| Cy3-1642-183 | Cy3-GGTGGTGGZGGTTGTGGZGGTGGTGG (SEQ ID NO: 165) | 9148.28 |
| Cy3-1642-184 | Cy3-GGZGGTGGZGGTTGTGGZGGTGGZGG (SEQ ID NO: 166) | 9516.56 |
| Cy3-1642-185 | Cy3-GGTGGTGGTGGTZGTGGTGGTGGTGG (SEQ ID NO: 167) | 8964.14 |
| Cy3-1642-186 | Cy3-GGTGGTGGTGGZZGZGGTGGTGGTGG (SEQ ID NO: 168) | 9332.42 |
| Cy3-1642-187 | Cy3-GGTGGTGGTGGZTGZGGTGGTGGTGG (SEQ ID NO: 169) | 9148.28 |
| Cy3-1642-188 | Cy3-GGZGGTGGTGGTTGTGGTGGTGGTGG (SEQ ID NO: 170) | 8964.14 |
| Cy3-1642-189 | Cy3-GGTGGZGGTGGTTGTGGTGGTGGTGG (SEQ ID NO: 171) | 8964.14 |
| Cy3-1642-190 | Cy3-GGTGGTGGZGGTTGTGGTGGTGGTGG (SEQ ID NO: 172) | 8964.14 |
| Cy3-1642-191 | Cy3-GGTGGTGGTGGZTGTGGTGGTGGTGG (SEQ ID NO: 173) | 8964.14 |
| Cy3-1642-192 | Cy3-GGTGGTGGTGGTZGTGGTGGTGGTGG (SEQ ID NO: 174) | 8964.14 |
| Cy3-1642-193 | Cy3-GGTGGTGGTGGTTGZGGTGGTGGTGG (SEQ ID NO: 175) | 8964.14 |
| Cy3-1642-194 | Cy3-GGTGGTGGTGGTTGTGGZGGTGGTGG (SEQ ID NO: 176) | 8964.14 |
| Cy3-1642-195 | Cy3-GGTGGTGGTGGTTGTGGTGGZGGTGG (SEQ ID NO: 177) | 8964.14 |
| Cy3-1642-196 | Cy3-GGTGGTGGTGGTTGTGGTGGTGGZGG (SEQ ID NO: 178) | 8964.14 |
| Cy3-1642-197 | Cy3-GGTGGTGGTGGTTGTGGTGGZGGZGG (SEQ ID NO: 179) | 9148.28 |
| Cy3-1642-198 | Cy3-GGTGGTGGTGGTTGTGGZGGTGGZGG (SEQ ID NO: 180) | 9148.28 |
| Cy3-1642-199 | Cy3-GGTGGTGGTGGTTGZGGTGGTGGZGG (SEQ ID NO: 181) | 9148.28 |
| Cy3-1642-200 | Cy3-GGTGGTGGTGGTZGTGGTGGTGGZGG (SEQ ID NO: 182) | 9148.28 |

TABLE 5-continued

A list of modified AS1411 having hydrophobic groups such as 4-PB at 5 position of dU (5-(N-4-pyrrolebenzylcarboxyamide)-2'-deoxyuridine, 4-PBdU)

| Comp. No. | Cy3-labeled Modified dU-AS1411 sequence | MS |
|---|---|---|
| Cy3-1642-201 | Cy3-GGTGGTGGTGGZTGTGGTGGTGGZGG (SEQ ID NO: 183) | 9148.28 |
| Cy3-1642-202 | Cy3-GGTGGTGGZGGTTGTGGTGGTGGZGG (SEQ ID NO: 184) | 9148.28 |
| Cy3-1642-203 | Cy3-GGTGGZGGTGGTTGTGGTGGTGGZGG (SEQ ID NO: 185) | 9148.28 |
| Cy3-1642-204 | Cy3-GGZGGTGGTGGTTGTGGTGGTGGZGG (SEQ ID NO: 186) | 9148.28 |
| Cy3-1642-205 | Cy3-GGTGGTGGTGGZZGTGGTGGTGGZGG (SEQ ID NO: 187) | 9332.42 |
| Cy3-1642-206 | Cy3-GGTGGTGGTGGZZGTGGTGGTGGTGG (SEQ ID NO: 188) | 9148.28 |
| Cy3-1642-207 | Cy3-GGTGGTGGTGGZZGZGGTGGTGGTGG (SEQ ID NO: 189) | 9332.42 |
| Cy3-1642-208 | Cy3-GGTGGTGGTGGZZGTGGZGGTGGTGG (SEQ ID NO: 190) | 9332.42 |
| Cy3-1642-209 | Cy3-GGTGGTGGTGGZZGTGGTGGZGGTGG (SEQ ID NO: 191) | 9332.42 |
| Cy3-1642-210 | Cy3-GGTGGTGGZGGZZGTGGTGGTGGTGG (SEQ ID NO: 192) | 9332.42 |
| Cy3-1642-211 | Cy3-GGTGGZGGTGGZZGTGGTGGTGGTGG (SEQ ID NO: 193) | 9332.42 |
| Cy3-1642-212 | Cy3-GGZGGTGGTGGZZGTGGTGGTGGTGG (SEQ ID NO: 194) | 9332.42 |
| Cy3-1642-213 | Cy3-GGTGGTGGZGGTTGZGGTGGTGGTGG (SEQ ID NO: 195) | 9148.28 |
| Cy3-1642-214 | Cy3-GGTGGZGGTGGTTGTGGZGGTGGTGG (SEQ ID NO: 196) | 9148.28 |
| Cy3-1642-215 | Cy3-GGZGGTGGTGGTTGTGGTGGZGGTGG (SEQ ID NO: 197) | 9148.28 |
| Cy3-1642-216 | Cy3-GGTGGZGGZGGTTGZGGZGGTGG (SEQ ID NO: 198) | 9700.7 |
| Cy3-1642-217 | Cy3-GGZGGZGGTGGTTGZGGZGGTGGZGG (SEQ ID NO: 199) | 9884.84 |
| Cy3-1642-218 | Cy3-ZGGTGGTGGTGGTTGTGGTGGTGGTGGZ (SEQ ID NO: 200) | 9756.68 |
| Cy3-1642-219 | Cy3-CCZCCZCCZCCZZCZCCZCCZCC (SEQ ID NO: 201) | 9756.75 |
| Cy3-1642-220 | Cy3-CCZCCZCCZCCTTCTCCZCCZCCZCC (SEQ ID NO: 202) | 9204.33 |
| Cy3-1642-221 | Cy3-CCTCCTCCTCCZZCZCCTCCTCCTCC (SEQ ID NO: 203) | 8651.91 |

Z = 4-PBdU 1.2: Synthesis of Cy3-Labeled Modified dU AS1411 and GRO29A

Cy3-labeled AS1411 (GGTGGTGGTGGTTGTGGTGGTGG, SEQ ID NO: 2) and GRO29A (TTTGGTGGTGGTGGTTGTGGTGGTGGTGG, SEQ ID NO: 1), and Cy3-labeled modified dU-containing AS1411 and GRO29A were synthesized using a Mermade 12 DNA synthesizer (Bio-Automation Manufacturing, Irging, Tex.) with standard solid phase phosphoramidite chemistry. 5-(N-benzylcarboxyamide)-2'-deoxyuridine (BzdU), 5-(N-naphthylcarboxyamide)-2'-deoxyuridine (NapdU), and 5-(N-4-Pyrrolebenzylcarboxyamide)-2'-deoxyuridine (4-PBdU)-phosphoramidite were offered by Samchully Pharmaceutical (Seoul, Korea). All oligonucleotide syntheses were performed in house.

All oligonucleotides were synthesized on functionalized controlled pore glass (CPG) synthesized using a Mermade 12 DNA synthesizer (BioAutomation Manufacturing, Irging, Tex.) with 0.067 M solution of the modified dU (BzdU, NapdU or 4-PBdU)-amidite in anhydrous acetonitrile. For incorporation of dA, dG, dC and dT residues standard phosphoramidites with excyclic amino groups protected with benzoyl group (for dA and dC) and isobutyryl group (for G) were used. For incorporation of modified dU-amidite, phosphoramidite solution was delivered in two portions, each followed by a 5 min coupling wait time. Oxidation of the internucleotide phosphate to phosphate was carried out using an oxidizer [tetrahydrofuran (THF), pyridine, 0.02 M iodine and water] with waiting time. All other steps in the protocol supplied by the manufacturer were used without modification. The coupling efficiencies were >97%. After completion of the synthesis, the next step is treatment with the cleavage solution (t-butylamine:methanol:water, 1:1:2) at 70° C. for 5 hours to hydrolyze the ester linking the DNA to the support and to remove protecting groups from the purine and pyrimidine bases and followed by freezing, filtration, and speed-vac evaporation to dryness.

Crude oligonucleotides were purified by high performance liquid chromatography (AKTA basic HPLC, XBridge OST C18 10×50 mm, A=100 mM buffer triethylammoniumbiocarbonate (TEAB), pH=7, B=acetonitrile, 8% to 40% B in 20 min, flow 5 mL min-1, at 65° C., 1=254 and 290 nm). Purified aptamers were precipitated by ethanol and desalted by Centricon (Millipore Bedford, Mass.). Finally, desalted aptamers were resuspened in water or phosphate buffered saline and sterilized by filtration through a 0.2-μm syringe filter. Molecular weight and purity of each aptamer was checked by Q-TRAP 2000 ESI-MS spectroscopy (Applied Biosystems foster city, CA) and P/ACE™ 2000 capillary gel electrophoresis (Beckman coulter. fullerton, CA).

Example 2

Affinity of the Aptamer to Nucleolin 2.1: Cell Culture

C6 cells (American type culture collection), which are a rat glioma cell lines, were maintained in DMEM (Gibco, Grand Island, N.Y.) supplemented with 10% fetal bovine serum (FBS, Invitrogen, Grand Island, N.Y.), 10 U/ml penicillin (Invitrogen, Grand Island, N.Y.), and 10 μg/ml streptomycin in a 5% $CO_2$-humidified chamber at 37° C. The cells were cultured in multiwell chamber slides overnight or 2 days till they reach about 50-80% confluence. After confluent of cells 90-100%, cells were aspirated off media with transfer pipettes and washed with PBS (1× Phosphate Buffered Saline) briefly. After trypsinization, cells were collected by standard culture media and ⅕ cells that were centrifuged 1000 rpm for 5 min were transferred into T75 flask holding 10 ml media.

2.2: Protein Assay

To normalize fluorescence signals of forty-seven Cy3-labeled BzdU-containing GRO29A and eighteen Cy3-labeled NapdU-containing GRO29A compounds, cells treated with each compound were collected with 120 μl PBS buffer after trypsinization and followed with BCA protein assay (Thermo Fisher Scientific Inc. Waltham, Mass.). Then, the collected cells were moved into 96-microplate well and treated mixture of reagent A and B (1:50 (v/v)) and incubated at 37° C. for 30 min. After the buret reaction, the absorbance at or near 562 nm reader measured on a plate.

2.3: Fluorescence Intensity

To determine the targeting efficiency of the cancers, fluorescence intensities of forty-seven Cy3-labeled BzdU-containing GRO29A and eighteen Cy3-labeled NapdU-containing GRO29A compounds were quantified to evaluate their targeting efficiency at C6 cells by the Varioskan Flash spectral scanning multimode reader (Thermo Fisher Scientific Inc. Waltham, Mass.; excitation: 535 nm, scanning wavelength: 570 nm with a band width: 12 nm). C6 cells were seeded $1 \times 10^5$ cell density onto Magne to FACTION 24 plate (Chemicell, GmbH, Germany) and caring at a 5% $CO_2$-humidified chamber. After 24 hours of grown, these seeded cells were incubated in DMEM (Dubelocos' modified essential media) with 20 nM of Cy3-labeled GRO29A or AS1411, or 20 nM of each of the Cy3-labeled modified dU-containing GRO29A or AS1411 compounds at for 30 minute at 4° C. for decreasing non-specific binding during 30 min and rinsed by PBS (1×), then replaced to 200 μl Tris buffer, and then treated with each of 47 different compounds (20 pmole). Then, seeded cells was washed with PBS (phosphate buffered saline) two times each for 10 min at RT using shaking incubation (30 rpm) to remove the unbound Cy3-labeled modified dU-containing GRO29A or AS1411 compounds, and subjected to trypsinization to detach from the plate surface. These cells were collected by PBS (1×) (120 μl) and transferred into 96-well plate (Chemicell, GmbH, Germany) for measurement of fluorescence intensity (100 μl).

The fluorescence intensities of the Cy3-labeled modified dU-containing GRO29A or AS1411 compounds, targeting the nucleolin proteins expressed in the cellular membrane of the C6 cells, were quantified and normalized by units of the cells measured by the Bradford protein assay using Varioskan Flash spectral scanning multimode reader.

2.4: Confocal Laser Microscopy Assay

To further validate the increased binding affinity of modified dU-containing GRO29A or AS1411 by confocal microscopy analysis. Confocal microscopy imaging a laser scanning microscope (Carl Zeiss, Inc., Weimer, Germany; HFT 405/488 nm, DAPI imaging: 420-480 nm, Cy3-labeled compounds: 488/543) was used and each C6 cell was seeded $1 \times 10^5$ cells onto 12 mm sterile coverslip in 24-well plate. After 24 hr, C6 cells were incubated in PBS for 30 min at 4° C. with Cy3-GRO29A or AS1411, or Cy3-(5-BzdU)-modified GRO29A or AS1411 compounds (respectively, 20 nM).

To remove the unbound conjugates, the cells were washed three times during 10 min using shaking incubation (30 rpm) in PBS (1×) and fixed with 200 ul of 3.7% formaldehyde solution (Sigma, Saint Louis, Mo.) that was treated 200 μl into cells and incubated at shaking incubation (20 rpm) each for 20 min. After washed three times with PBS for 10 min into shaking incubation, this was followed by staining of the nucleus with a 4',6-diamidino-2-phenylindole dihydrochloride (DAPI; emission: 460 nm, blue color) using the mounting solution (Vector Laboratories, Inc., Burlingame, Calif.). Fluorescent imaging of targeting C6 cells was visualized by red color. All fluorescence data were acquired at an excitation of 535 nm and emission of 570 nm. The side of fixed cells onto coverslip was put on 10 μl of mountain solution (Vector Resources Inc, Torrance, Calif. USA). The confocal images were acquired at low magnifications (200×).

2.5: Statistical Analysis

Fold ratio of fluorescence activity for 47 different compounds of Cy3-labeled BzdU-containing GRO29A and eighteen Cy3-labeled NapdU-containing GRO29A and the Cy3- labeled CRO29A was normalized to the fluorescence signals of Cy3-AS1411 and p-values were calculated using the Student's t-test.

2.6: Results

Figure 2:
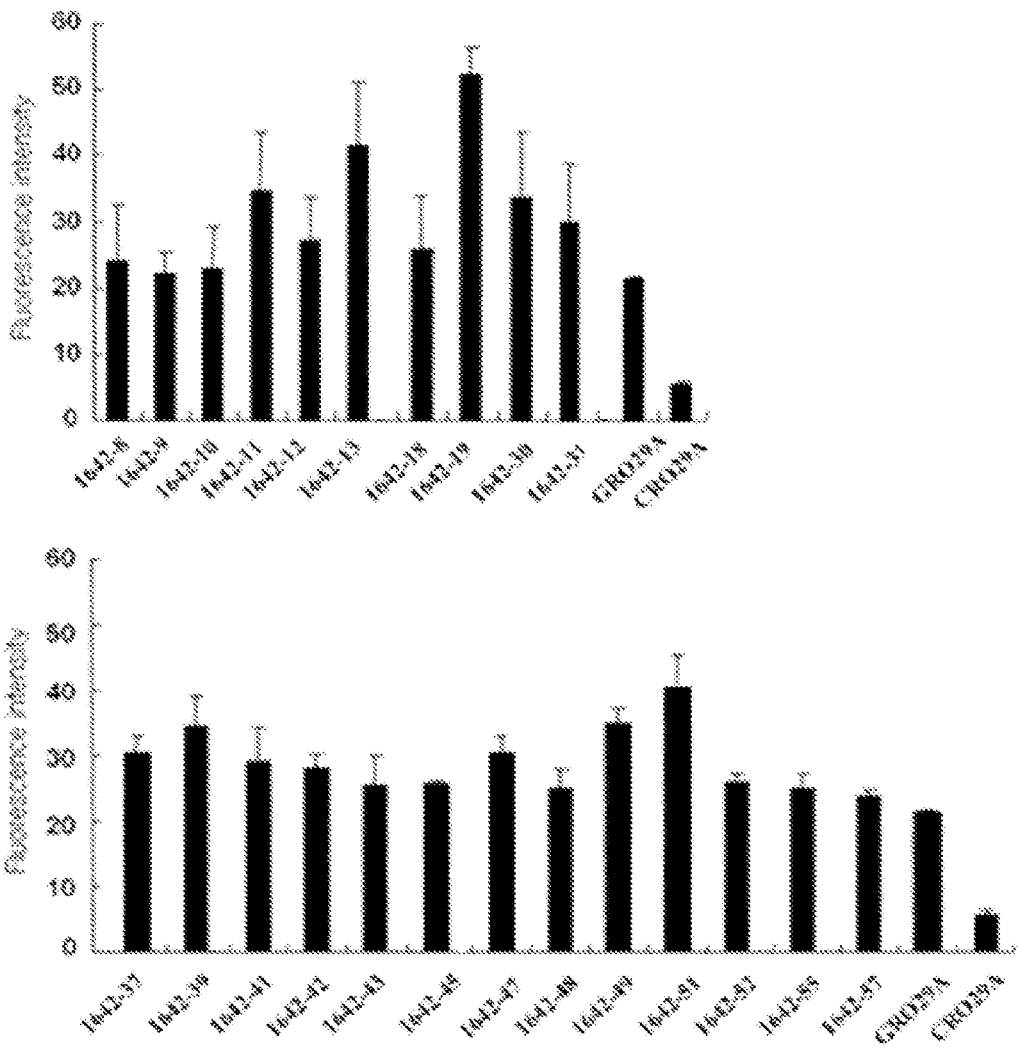
FIG. 2 shows results of fluorescence analysis of Cy3-labeled BzdU-containing GRO29A compounds targeting C6 cells.

The results of fluorescence analysis for several Cy3-labeled BzdU-containing GRO29A compounds are shown in FIG. 2. FIG. 2 shows the results of fluorescence analysis of Cy3-labeled BzdU-containing GRO29A compounds targeting C6 cells. The fluorescence of the Cy3-labeled BzdU-containing GRO29A compounds that were bound and targeted the nucleolin protein in the C6 cells was quantified. The X-axis indicates numbers of compounds. These data are presented as the means±SD calculated from quadruple wells. All fluorescence data were obtained at an excitation of 488 nm and emission of 543 nm. FIG. 2 presents comparison of the fluorescent intensity of the Cy3-labeled GRO29A with excitation at 488 nm and emission at 543 nm, showing that Cy3-labeled BzdU-containing GRO29A compounds showed either a slightly or a significantly greater fluorescent activity in the C6 cells compared to Cy3-labeled GRO29A or CRO29A.

The fold ratio of which the fluorescence signals for 47 different compounds of Cy3-labeled BzdU-containing GRO29A was normalized to that of Cy3-labeled GRO29A showed that seven different compounds, Compound No. 1642-11, 1642-13, 1642-19, 1642-30, 1642-39, 1642-49, and 1642-51 had about a 1.5 fold or more binding affinity to C6 cells as shown in FIG. 2. In particular, No. 1642-19 compound had approximately 2.5 fold higher fluorescent signals than Cy3-labeled GRO29A. The statistical analysis using Student-t test demonstrated that p-value with higher than 0.05 was found in 18 different compounds of Cy3-labeled BzdU-containing GRO29A including No. 1642-19, 1642-39, 1642-49, and 1642-51. This result implied that BzdU modification, such as compounds No. 1642-19, 1642-39, 1642-49, and 1642-51, significantly increased targeting affinity to C6 cells.

Figure 3:
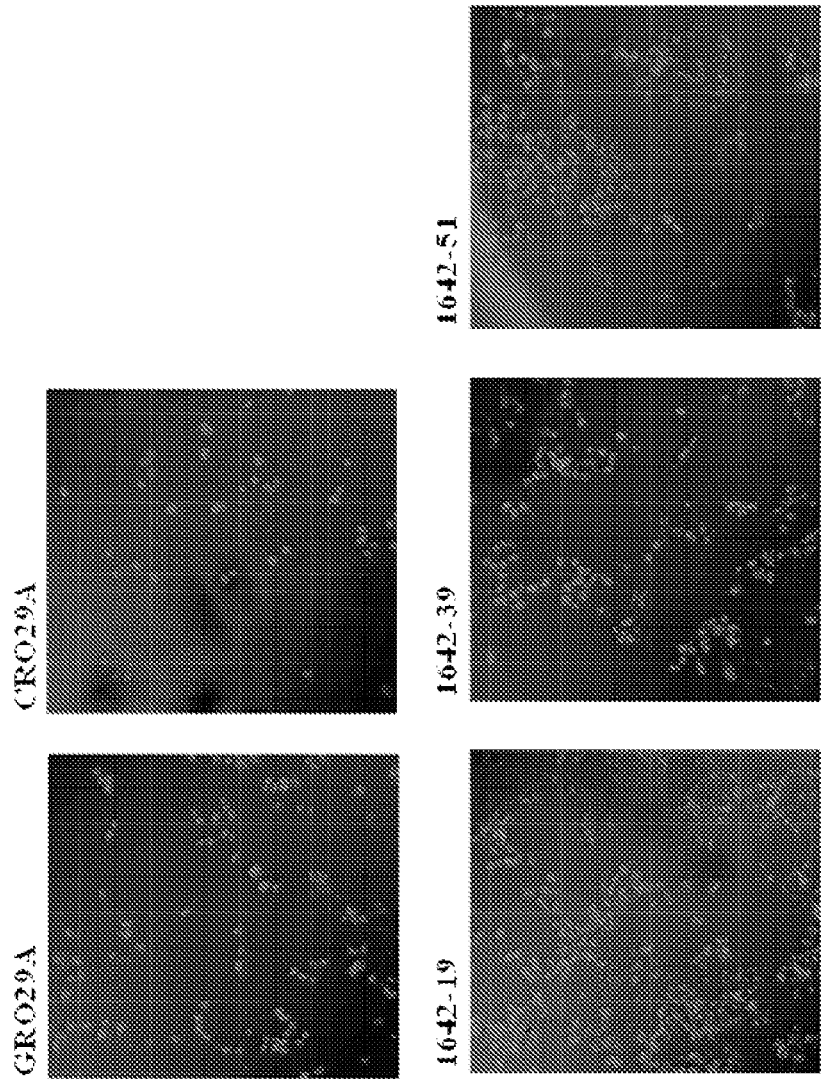
FIG. 3 shows confocal microscopy images of Cy3-labeled BzdU-containing GRO29A targeting C6 cells.

To further validate the increased binding affinity of Cy3-labeled BzdU-containing GRO29A by confocal microscopy analysis, compounds No. 1642-19, 1642-39 and 1642-51 were incubated and visualized in C6 cells with Cy3-labeled GRO29A and Cy3-labeled CRO29A (negative control). Twenty 20 nM of each compound was targeted in the C6 cells. The results of confocal microscopy analysis for compounds No. 1642-19, 1642-39, and 1642-51 were shown in FIG. 3. As shown in FIG. 3, comparison of the phase-contrast image and the nuclear DAPI staining revealed that numbers 1642-19, 1642-39, and 1642-51, and Cy3-labeled GRO29A were extensively bound to the plasma membrane of the C6 cells while the Cy3-labeled CRO29A was not clearly visualized in the C6 cells. The targeting affinity to C6 cells, shown in FIG. 3, demonstrated that compounds 1642-19, 1642-39, and 1642-51 had better targeting affinity than did Cy3-labeled GRO29A. The 1642-19 compound showed the highest fluorescent brightness in C6 cells.

To test functional activity of BzdU-containing GRO29A, the compounds numbers 1642-39, 1642-51 and 1642-19, in other cancer cells, the inventors first extended cancer targeting assay by selecting another cancer cells, HeLa (human cervix cancer cell line, ATCC), and a normal healthy cell line, CHO (chinese hamster ovary cell line, ATCC). The measurement of fluorescence intensity was performed as described above for C6 cells. The obtained results are shown in FIG. 4.

Figure 4:
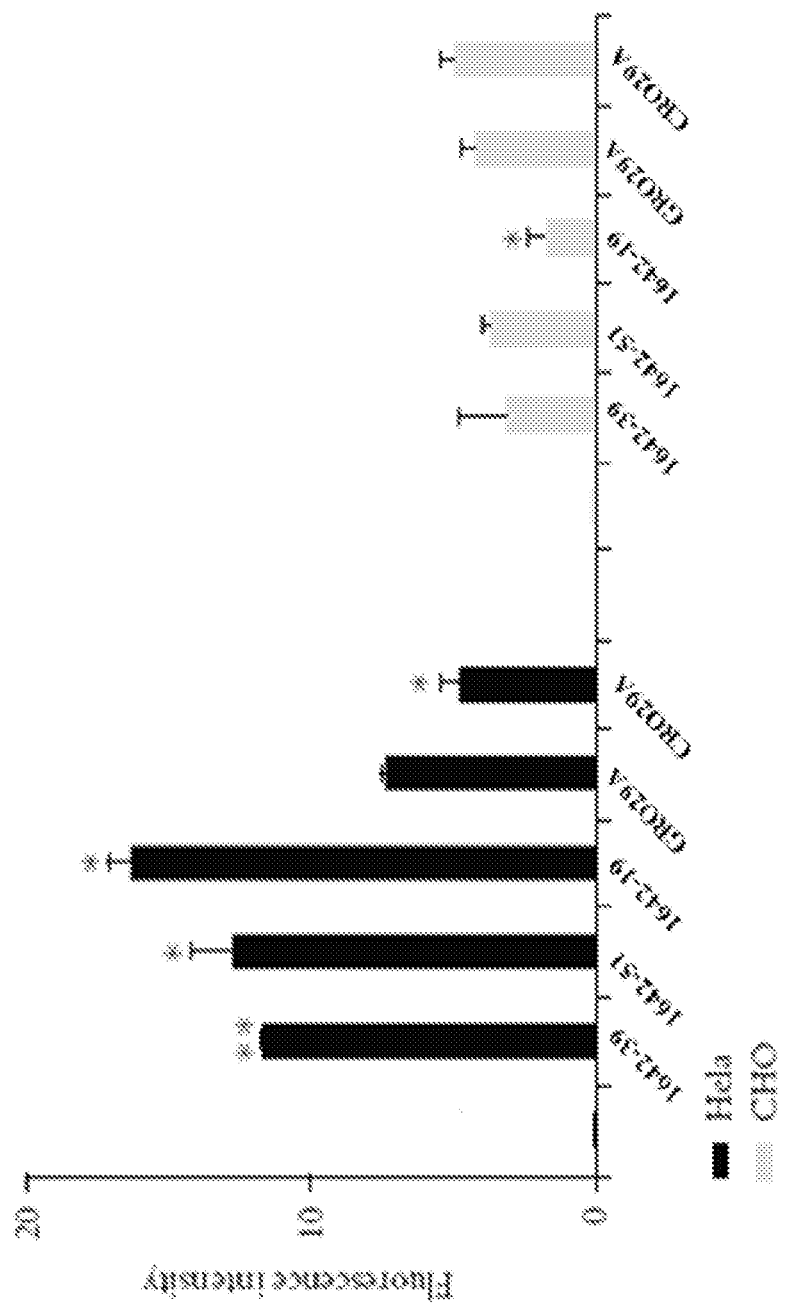
FIG. 4 shows fluorescence intensities measured by fluorescence analysis of numbers 1642-39, 1642-51, 1642-19 and Cy3-labeled GRO29A, and Cy3-labeled CRO29A (the control form of GRO29A labeled with Cy3) in HeLa and CHO cells.

FIG. 4 shows the results of fluorescence analysis of numbers 1642-39, 1642-51, 1642-19 and Cy3-labeled GRO29A, and Cy3-labeled CRO29A (the control form of GRO29A labeled with Cy3). Quantitative fluorescence intensity in HeLa and CHO cells. Data are represented as means±standard error of means (*$p<0.05$, **$P<0.005$ unpaired t-test). Similar results with C6 cell quantitative fluorescence intensity showed that compounds 1642-39, 1642-51 and 1642-19 had the higher binding affinity for the HeLa cells than the Cy3-labeled GRO29A, while the CRO29A had no significant fluorescent signal in HeLa cells. Especially, the 1642-19 compound had approximately a 2.3-fold higher fluorescent activity in HeLa cells than the Cy3-labeled GRO29A. However, in CHO cells, the compounds including numbers 1642-39, 1642- and 1642-19, Cy3-labeled CRO29A, and Cy3-labeled GRO29A showed undetectable fluorescence intensity. These results indicate that BzdU-containing GRO29A high-specifically targets to cancer cell compared with GRO29A.

Figure 5A:
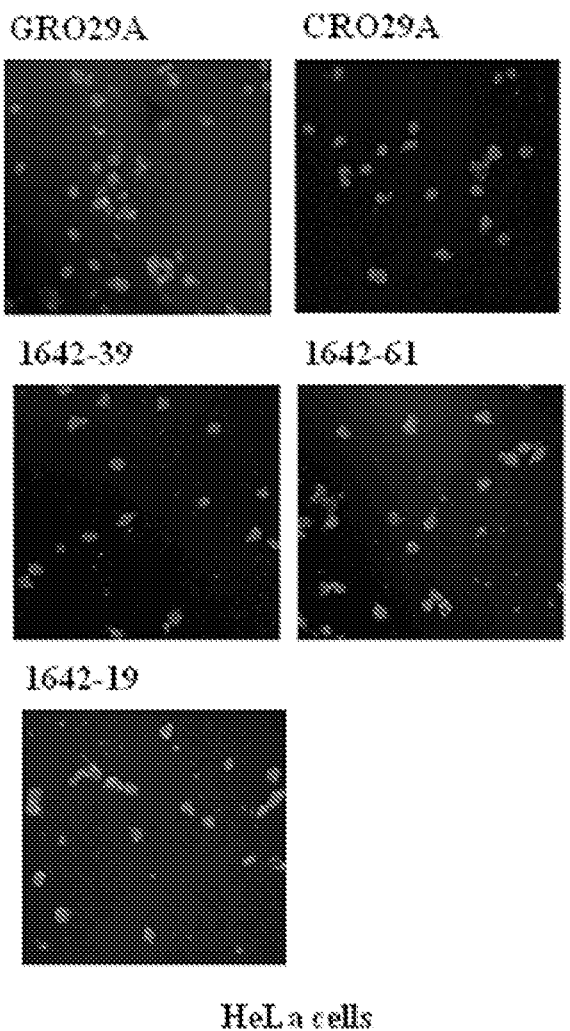
FIGS. 5A and 5B show confocal microscopy images in HeLa cells (5A) and CHO cells (5B).
Figure 5B:
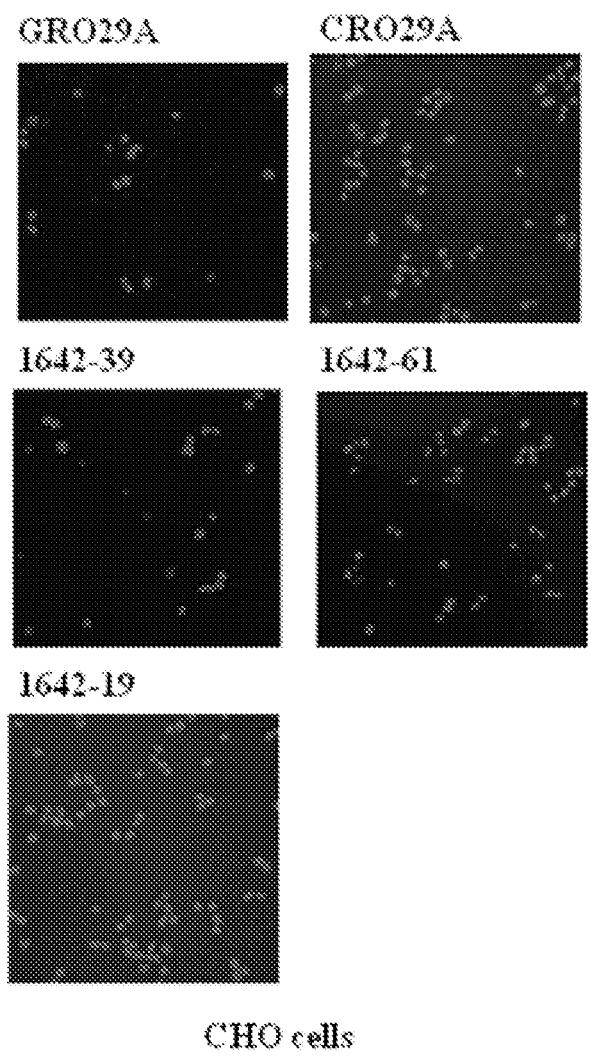

As shown in FIG. 4, there was no significant difference in binding affinity to CHO cells compared with the mutant. To confirm that the modified GRO29A has increased affinity compared to non-modified GRO29A other cells than C6, confocal microscopy analyses for HeLa cells and CHO cells were performed as the same method described above. The observed confocal microscopy images in HeLa cells and CHO cells are shown in FIG. 5A (Hela cell) and 5B (CHO cell). Confocal microscopy analysis validated that the compounds numbers 1642-39, 1642-51 and 1642-19 had extensively and better binding affinity to the plasma membrane of the HeLa cells than the Cy3-labeled GRO29A, while the CRO29A was not significantly visualized in the HeLa cells. There was no significant difference in binding affinity to CHO cells compared with the mutant. Confocal microscopy analysis validated that the compounds numbers 1642-39, 1642-51 and 1642-19 had extensively and better binding affinity to the plasma membrane of the HeLa cells than the Cy3-labeled GRO29A, while the CRO29A was not significantly visualized in the HeLa cells. As expected, the compounds including numbers 1642-39, 1642-51 and 1642-19, CRO29A, and GRO29A were not clearly visualized in CHO cells.

Figure 7:
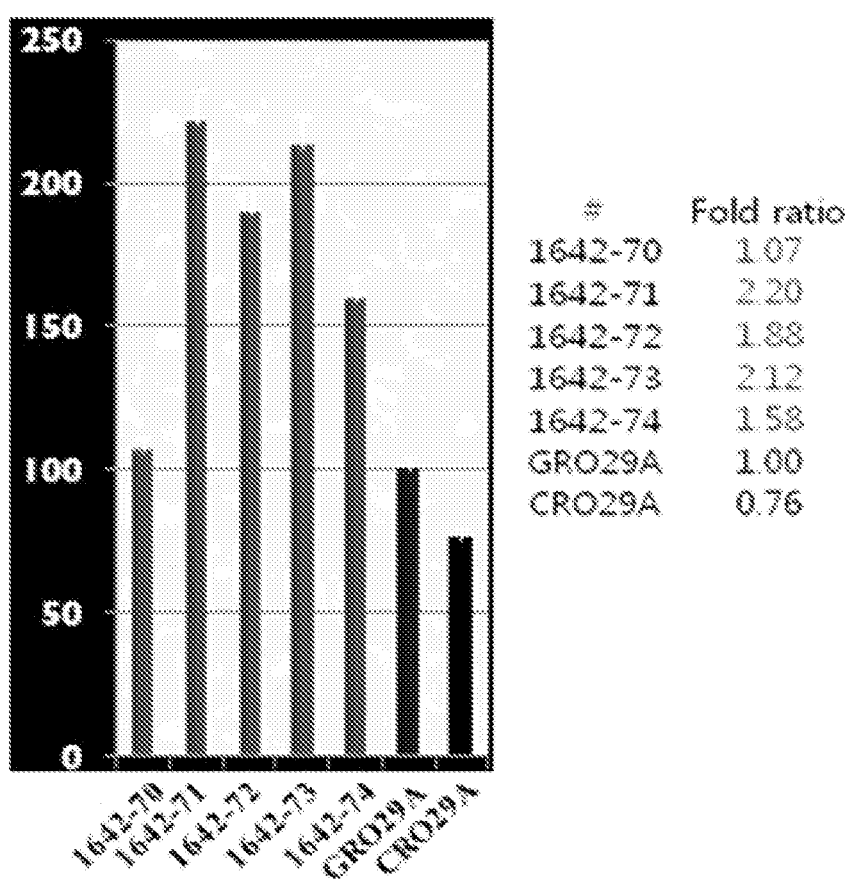
FIG. 7 shows results of fluorescence analysis of Cy3-labeled NapdU-containing GRO29A compounds targeting C6 cells.
Figure 8:
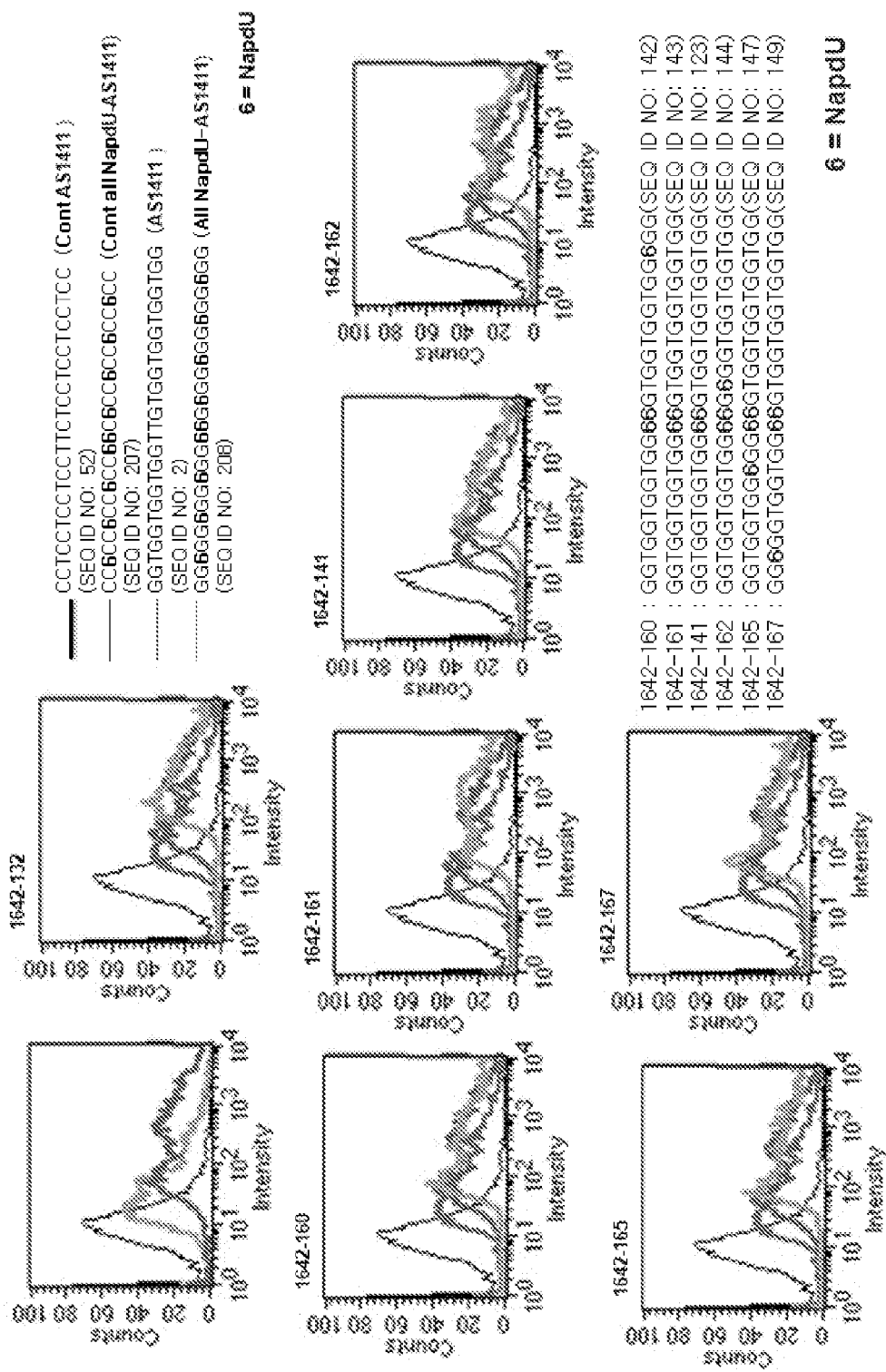
FIG. 8 shows results of a flow cytometric analysis of MDA-MB231 cells treated with NapdU-containing AS1411.
Figure 9:
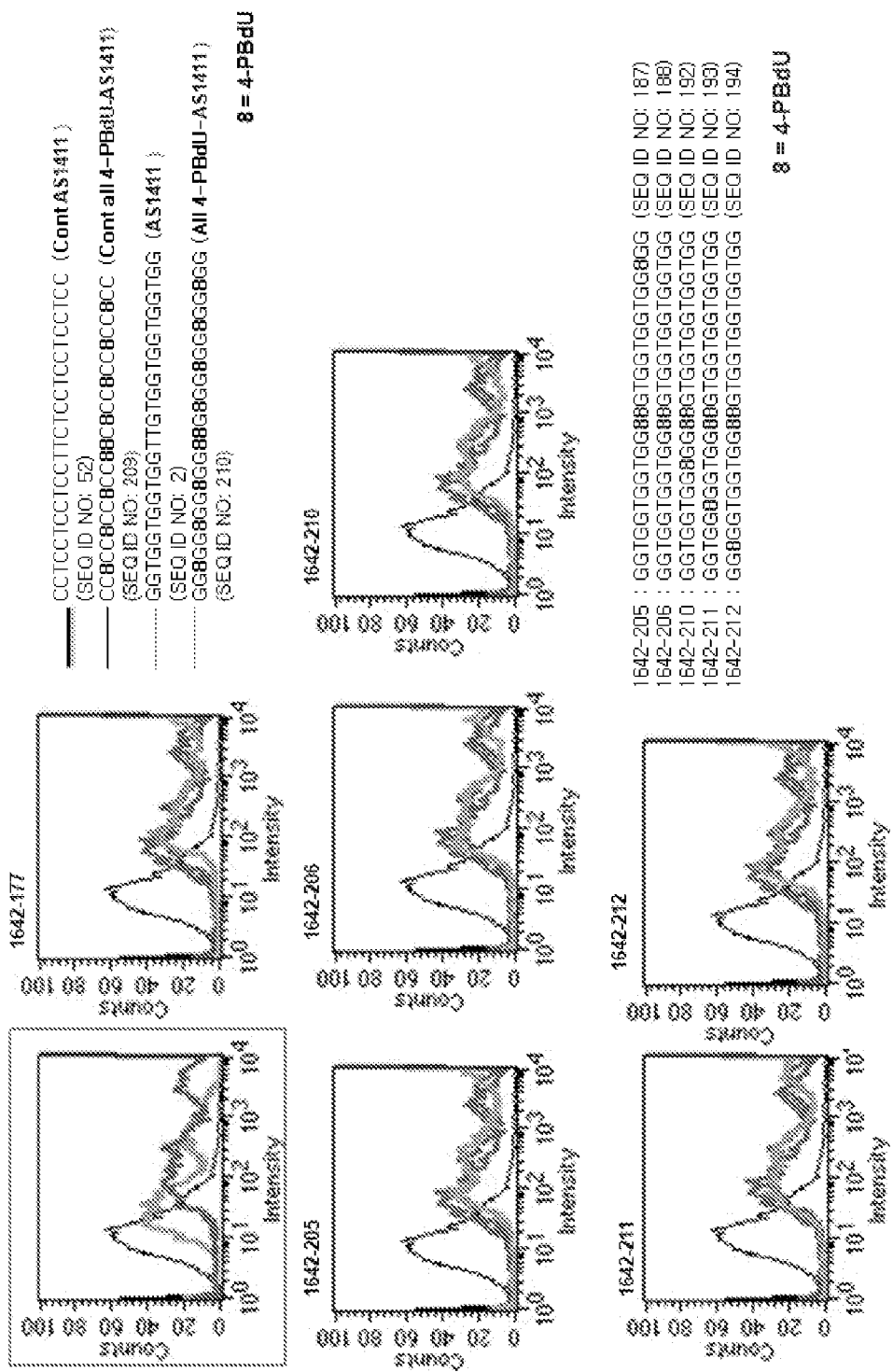
FIG. 9 shows results of a flow cytometric analysis of MDA-MB231 cells treated with 4-PBdU-containing AS1411.
Figure 10:
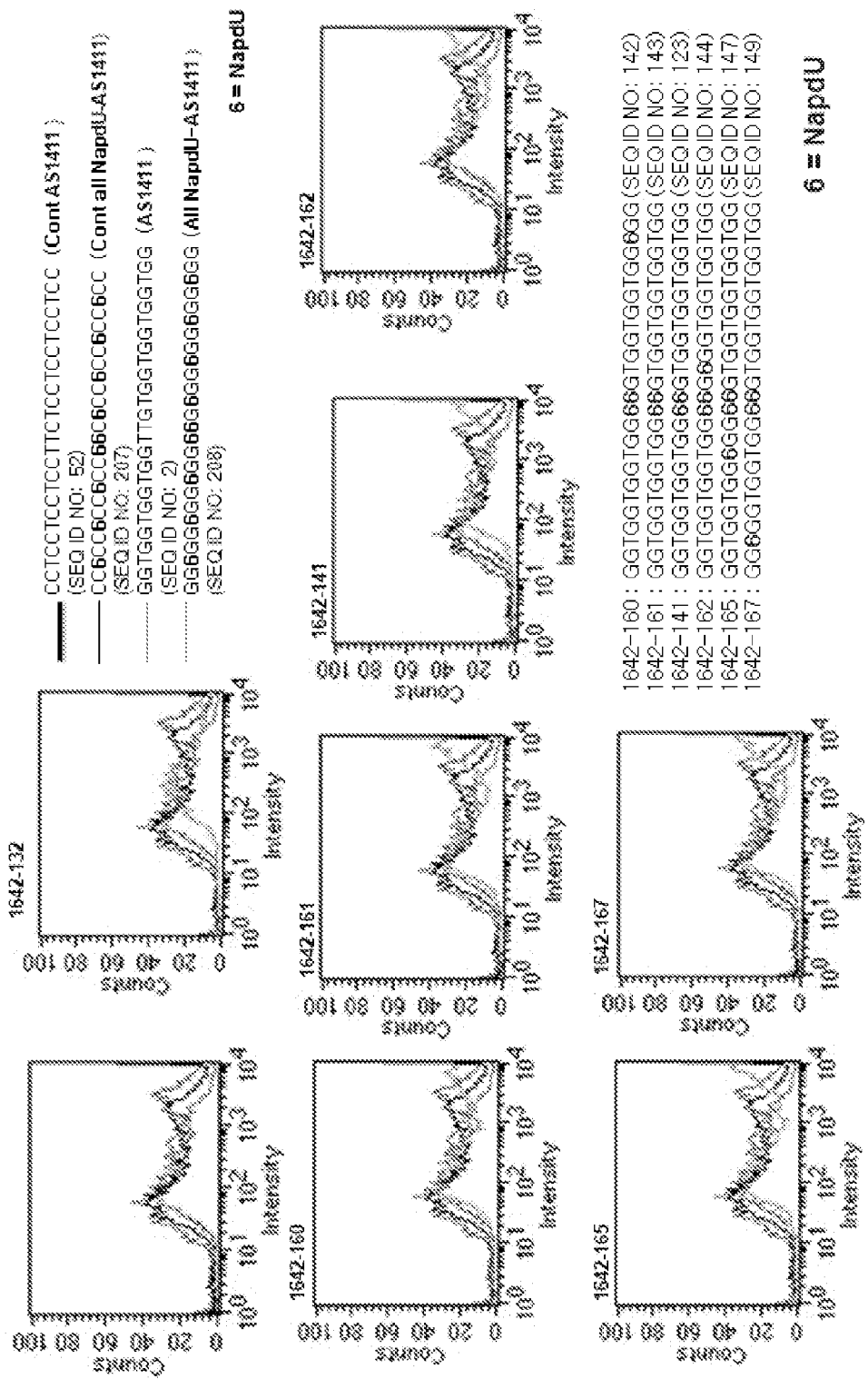
FIG. 10 shows results of a flow cytometric analysis of HepG2 cells treated with NapdU-containing AS1411.
Figure 11:
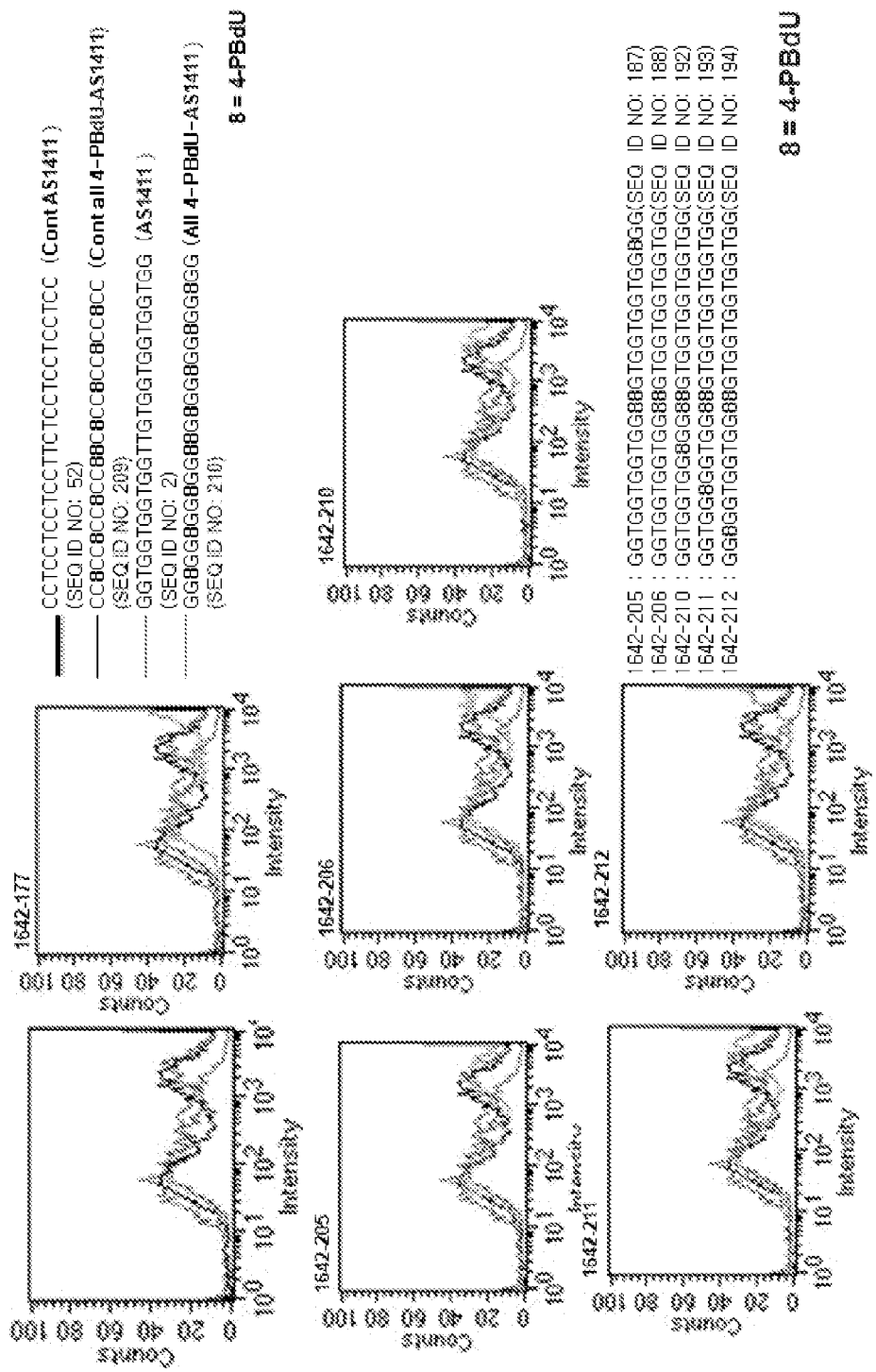
FIG. 11 shows results of a flow cytometric analysis of HepG2 cells treated with 4-PBdU-containing AS1411.
Figure 12:
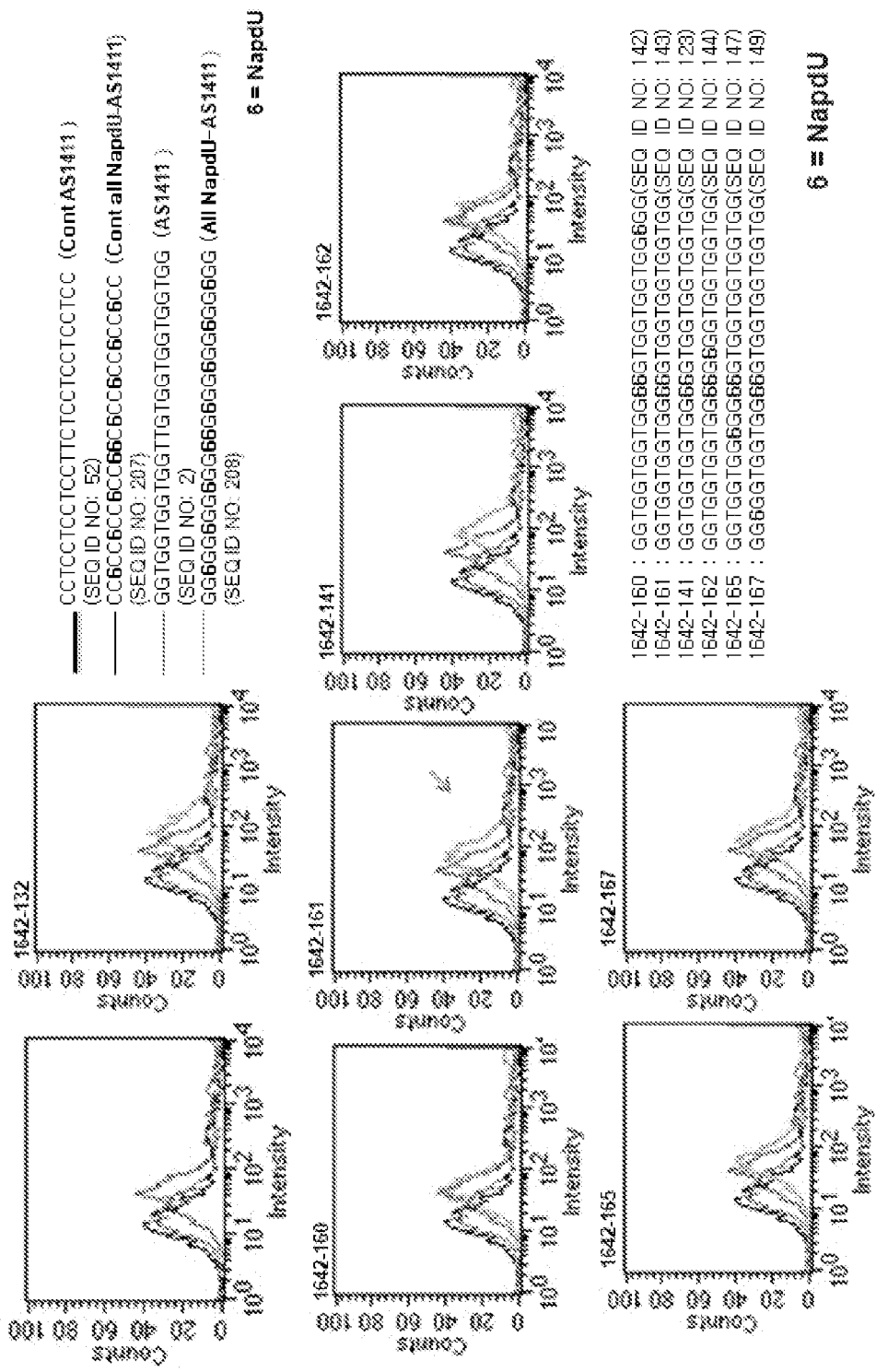
FIG. 12 shows results of a flow cytometric analysis of AGS cells treated with NapdU-containing AS1411.
Figure 13:
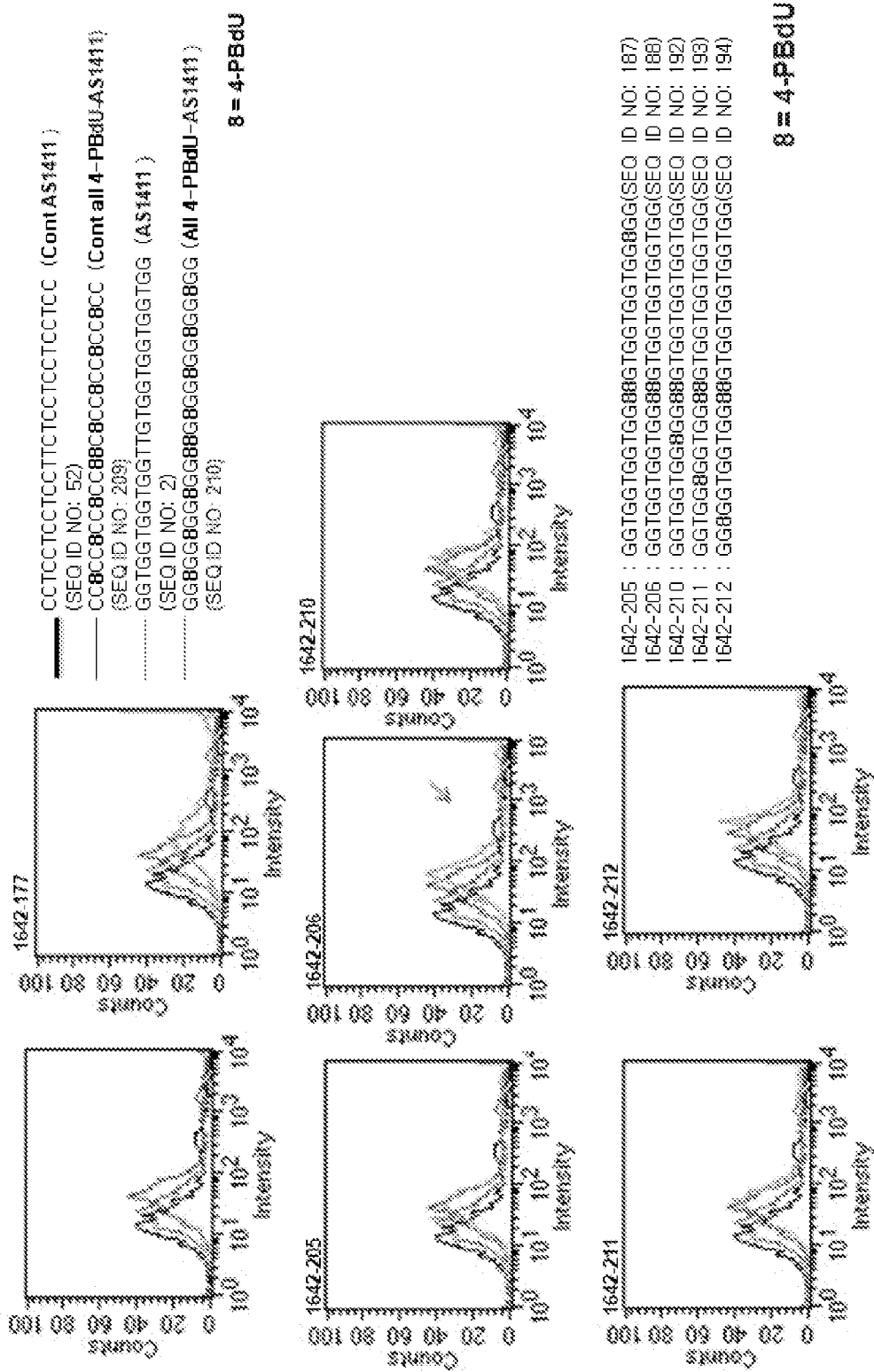
FIG. 13 shows results of a flow cytometric analysis of AGS cells treated with 4-PBdU-containing AS1411.
Figure 14:
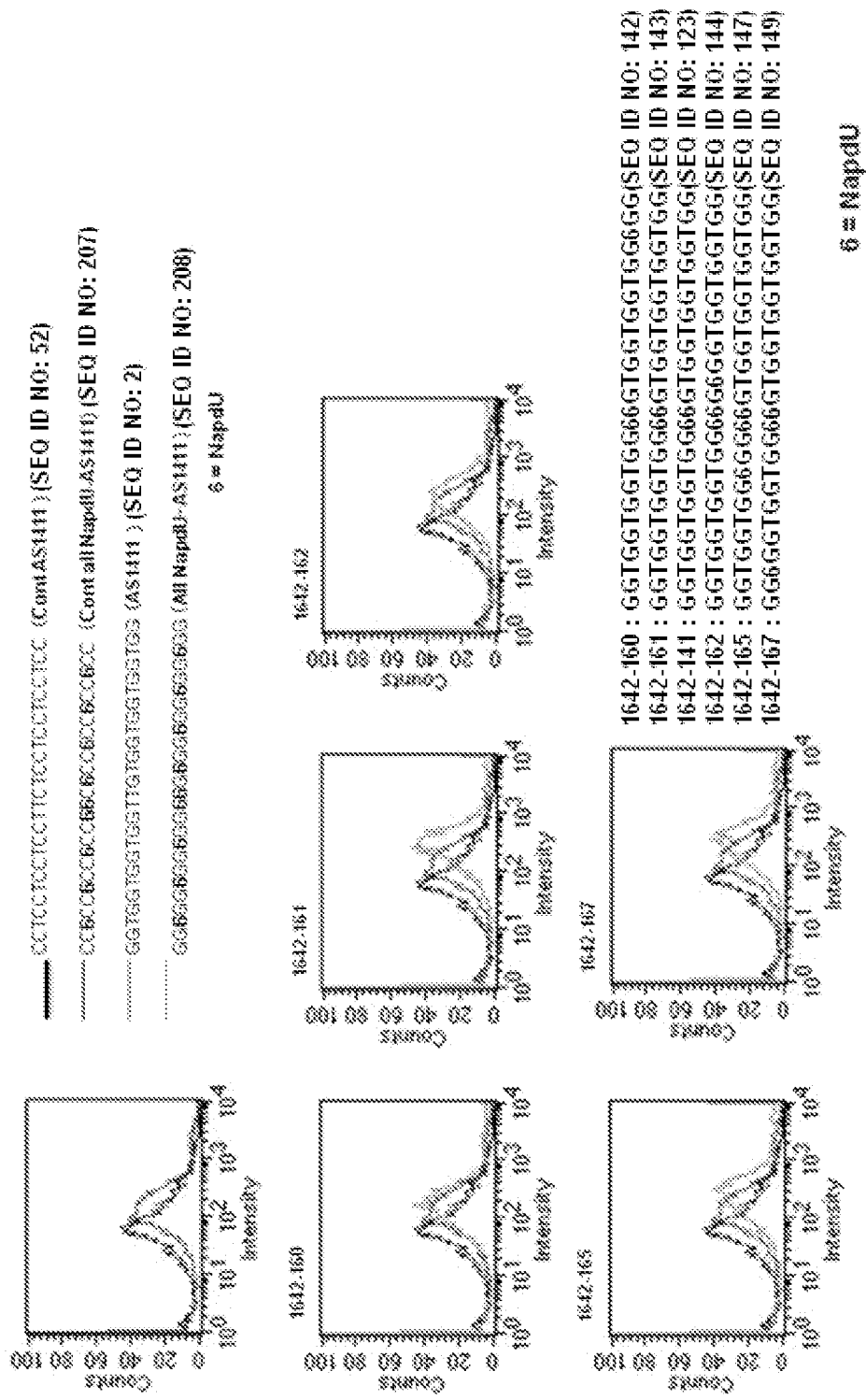
FIG. 14 shows results of a flow cytometric analysis of OVCAR-3 cells treated with NapdU-containing AS1411.
Figure 15:
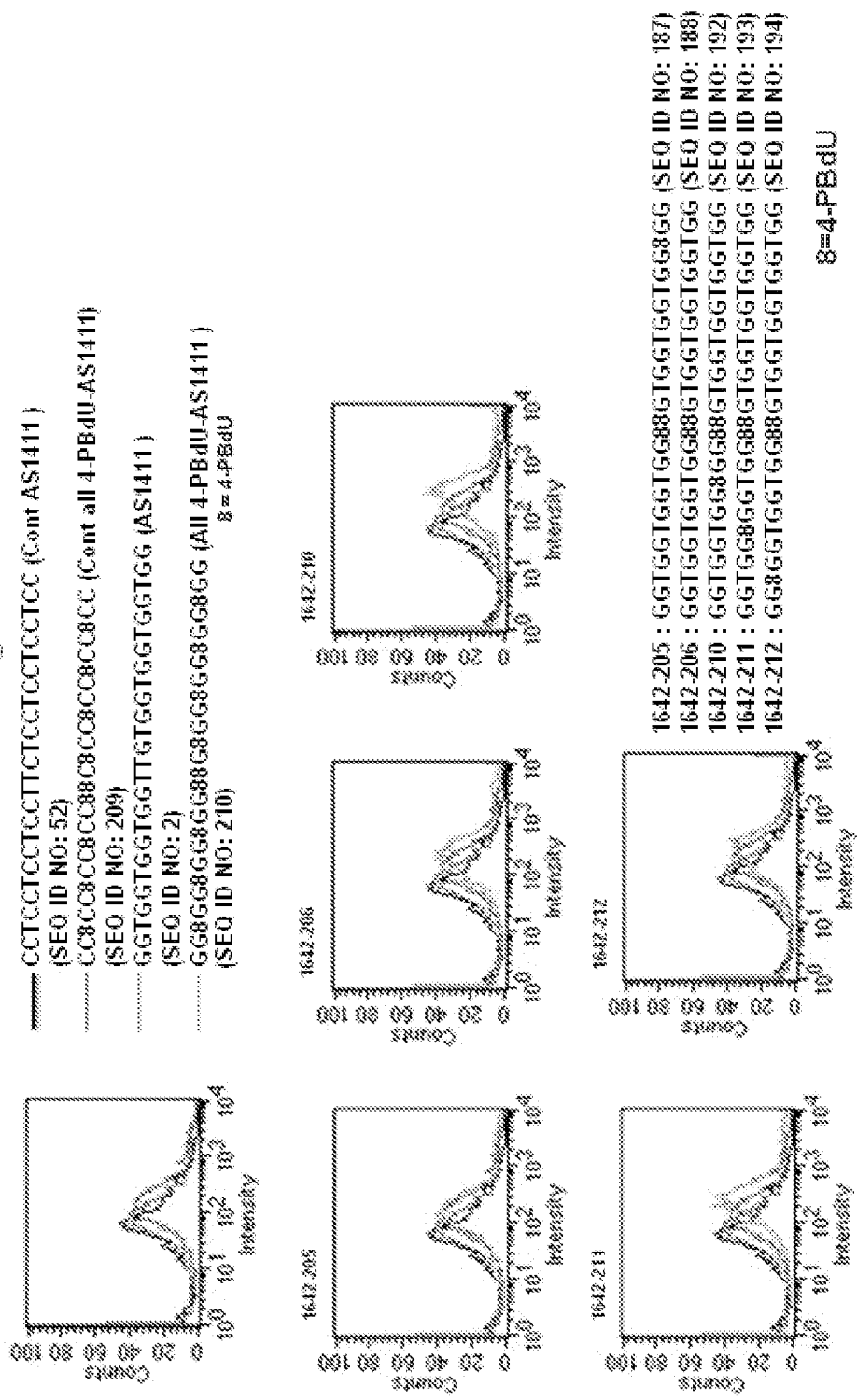
FIG. 15 shows results of a flow cytometric analysis of OVCAR-3 cells treated with 4-PBdU-containing AS1411.
Figure 16:
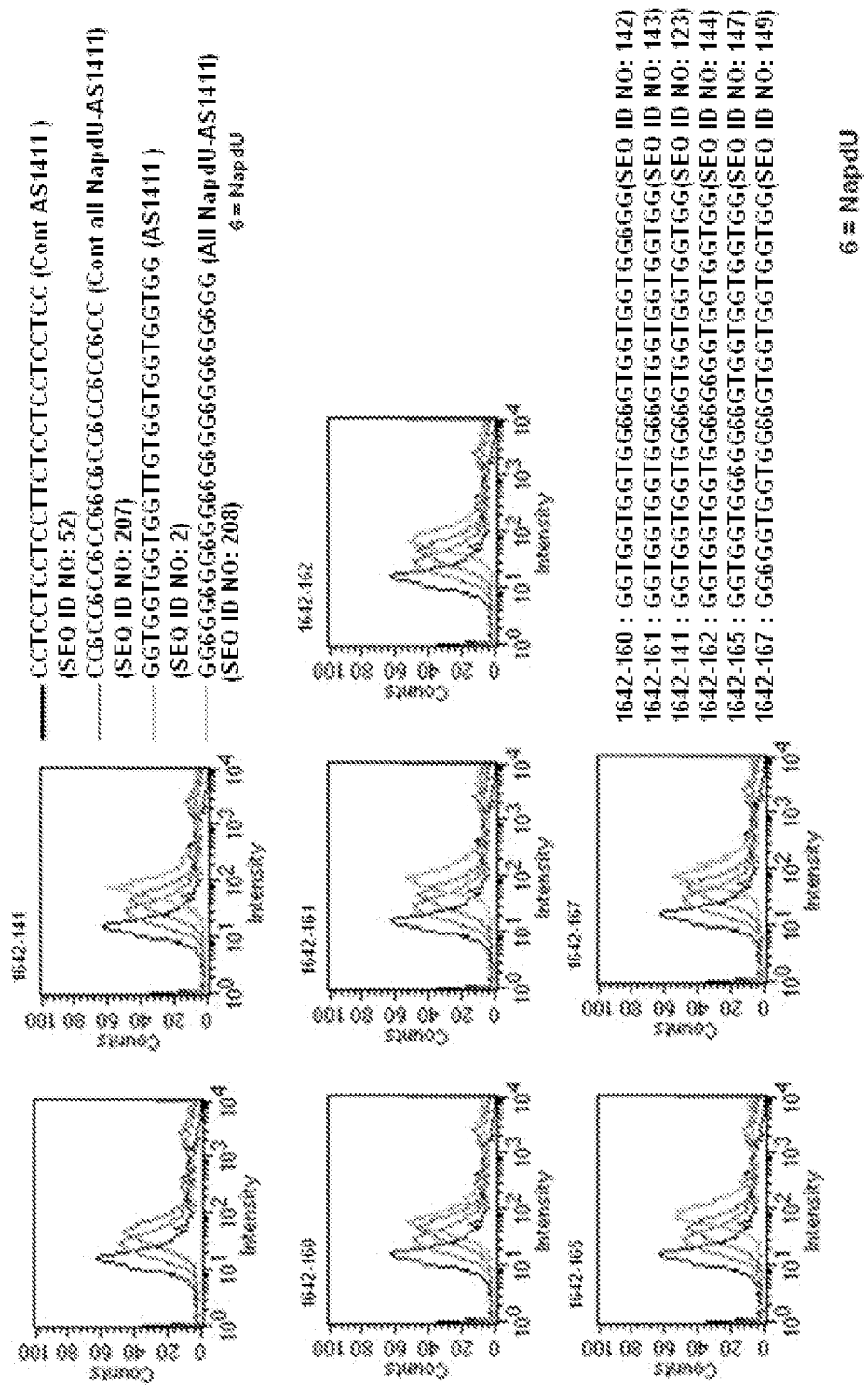
FIG. 16 shows results of a flow cytometric analysis of HeLa cells treated with NapdU-containing AS1411.
Figure 17:
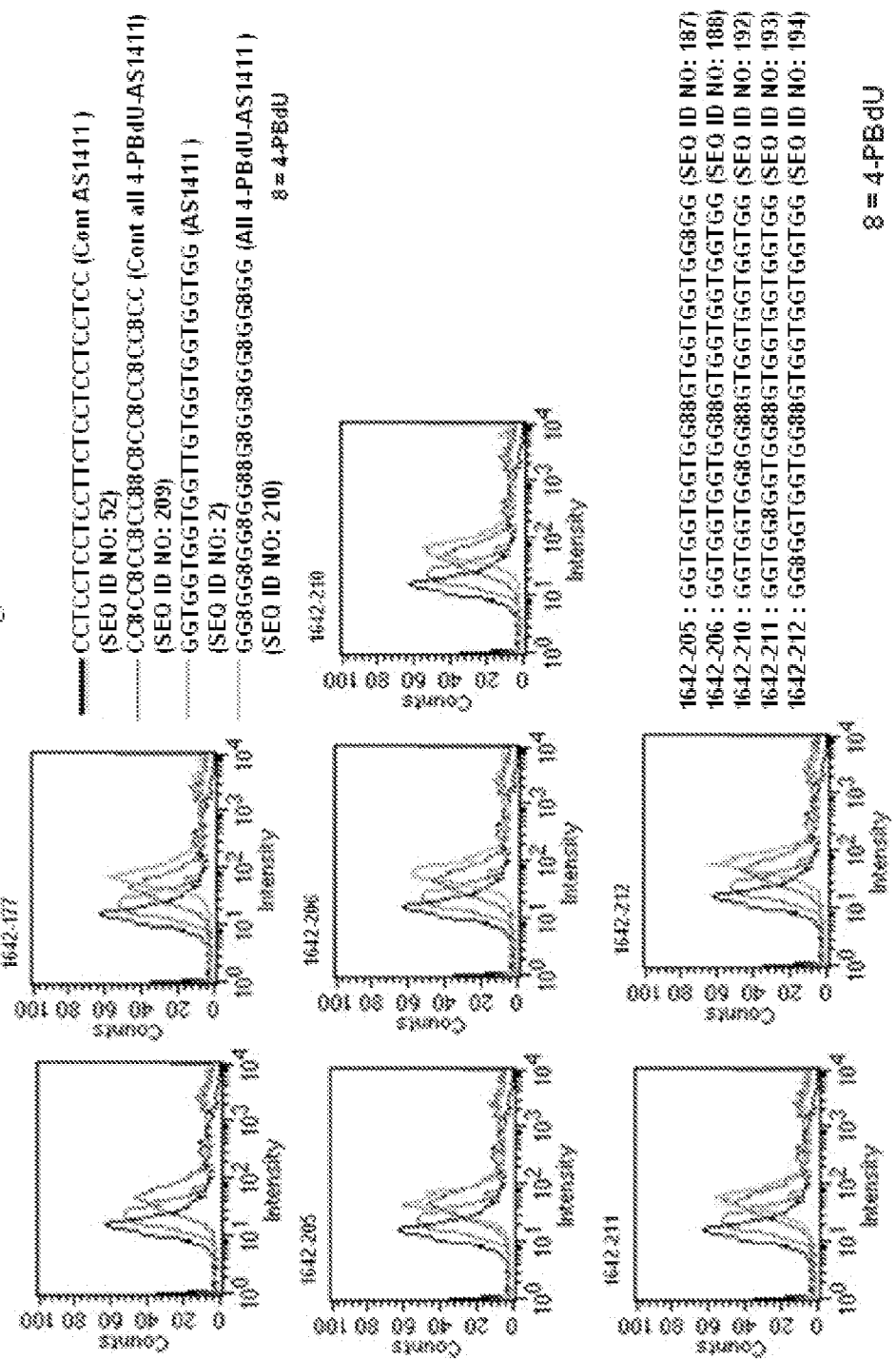
FIG. 17 shows results of a flow cytometric analysis of HeLa cells treated with 4-PBdU-containing AS1411.
Figure 18:
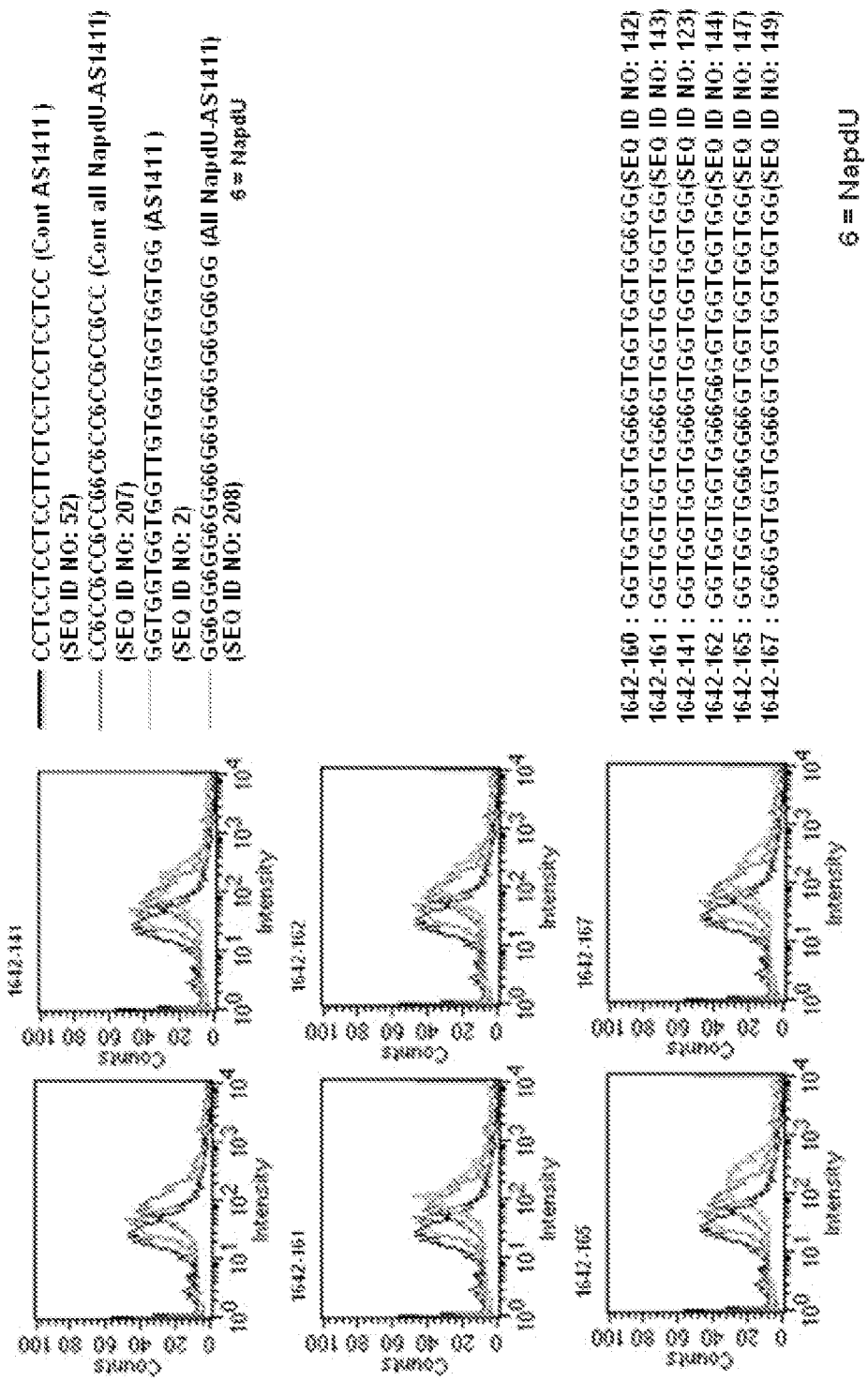
FIG. 18 shows results of a flow cytometric analysis of U87MG cells treated with NapdU-containing AS1411.
Figure 19:
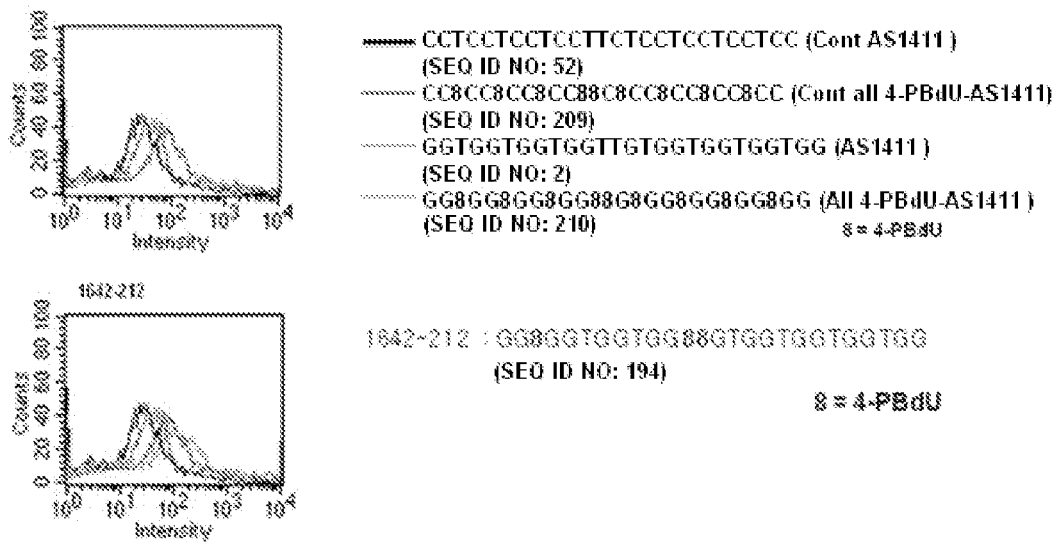
FIG. 19 shows results of a flow cytometric analysis of U87MG cells treated with 4-PBdU-containing AS1411.
Figure 20:
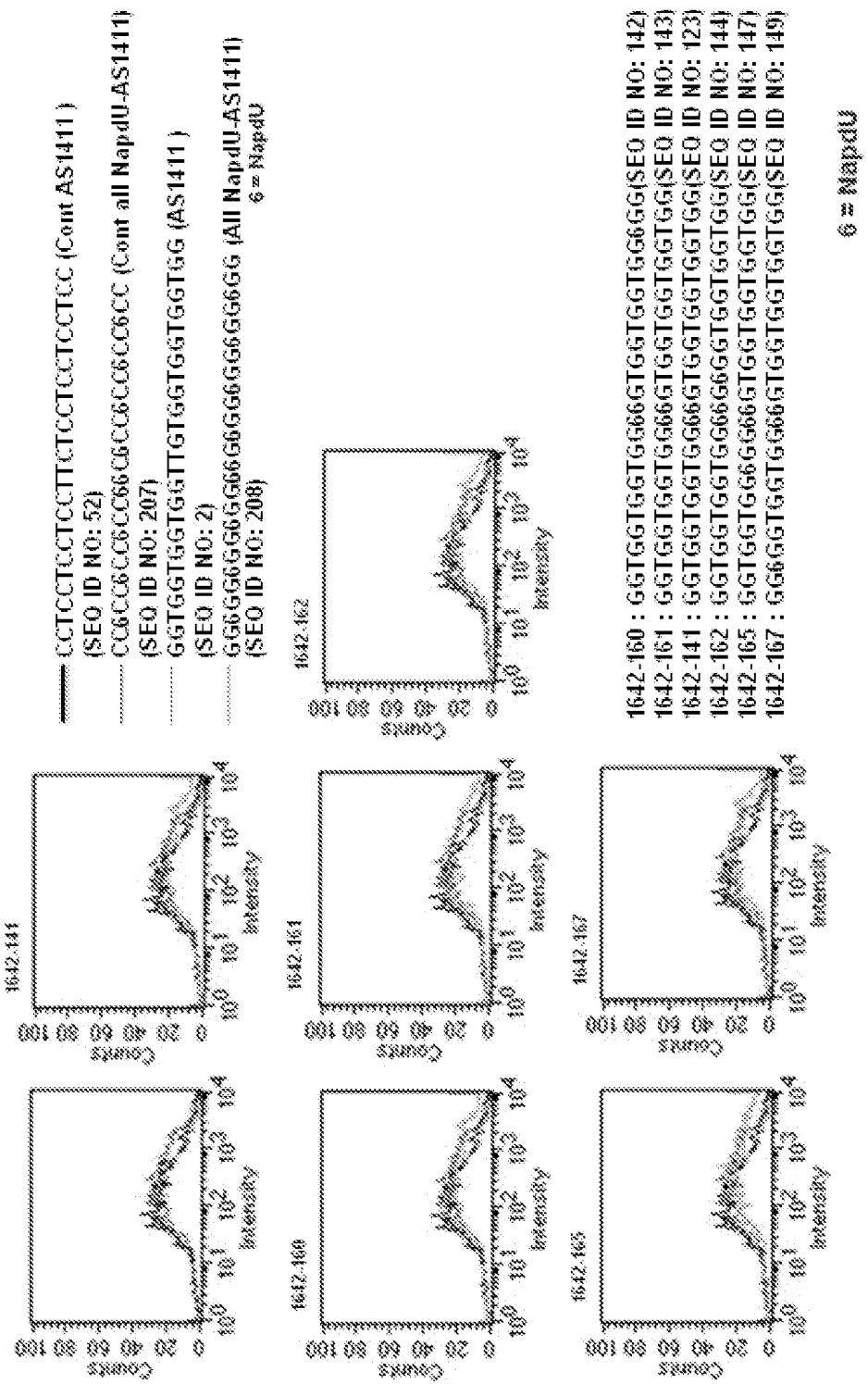
FIG. 20 shows results of a flow cytometric analysis of NIHT3 cells treated with NapdU-containing AS1411.
Figure 21:
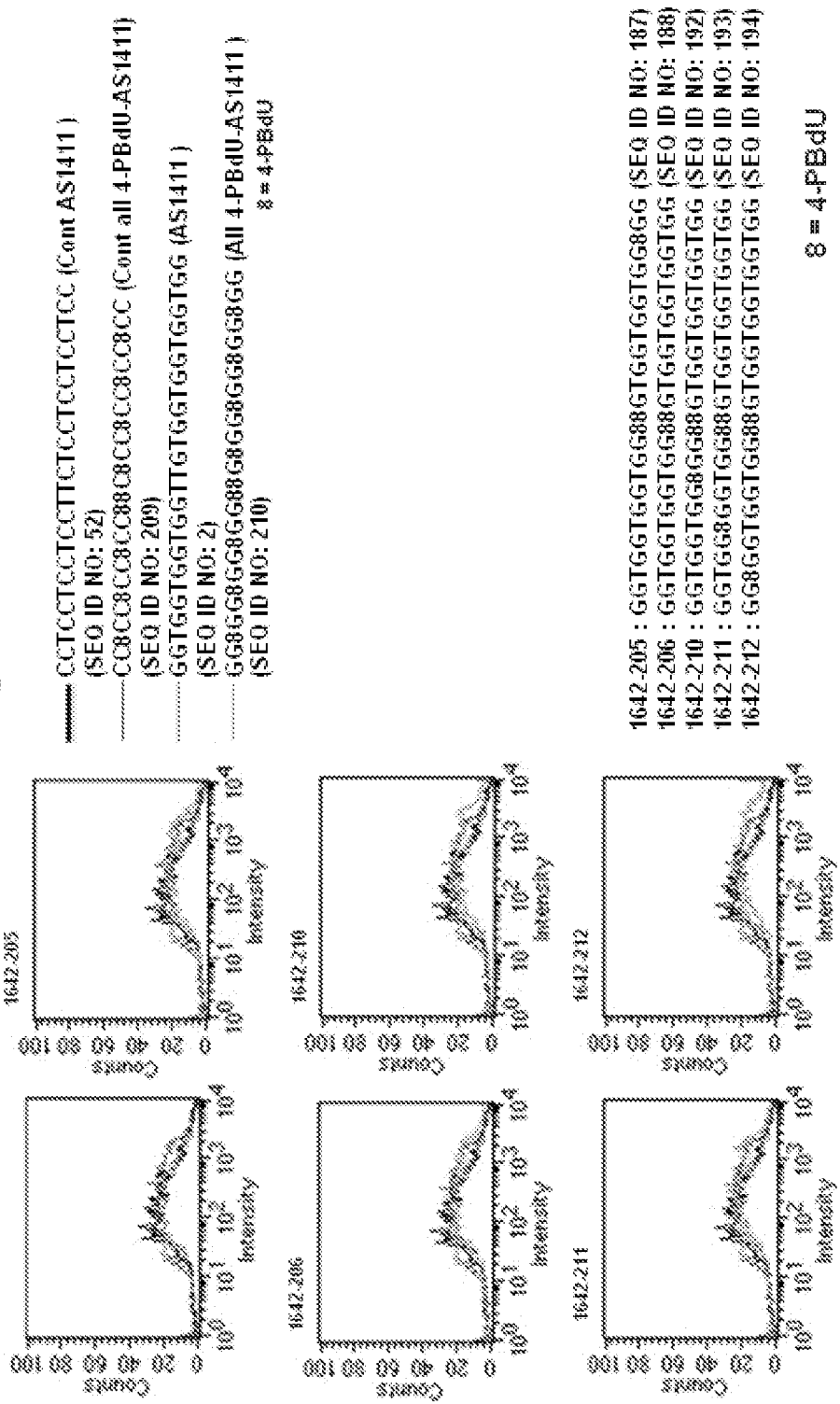
FIG. 21 shows results of a flow cytometric analysis of NIHT3 cells treated with 4-PBdU-containing AS1411.
Figure 22:
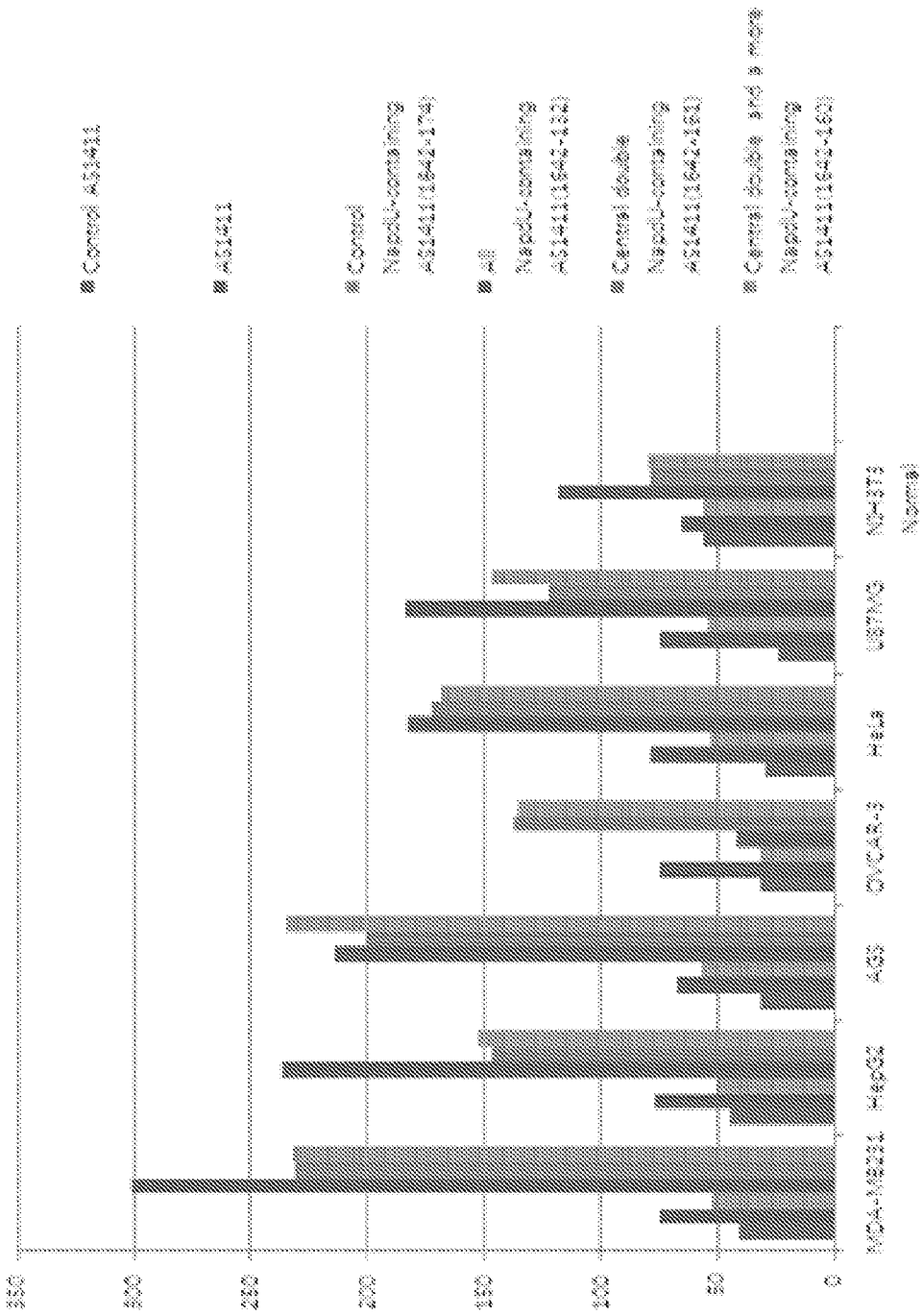
FIG. 22 shows results of a quantification of FACS analysis for various cell lines.
Figure 23:
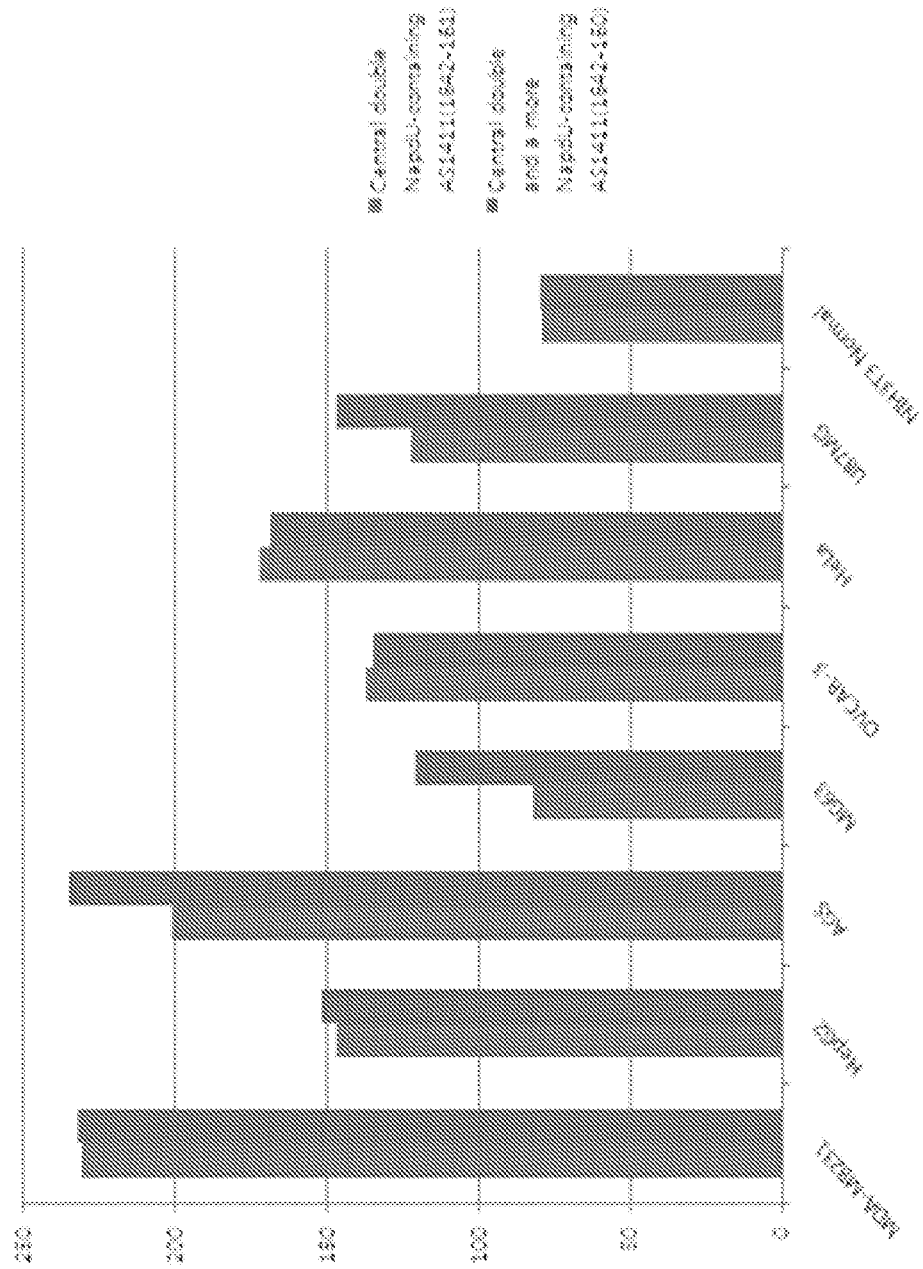
FIG. 23 shows activities between central double modification and a more modification of AS1411.
Figure 24:
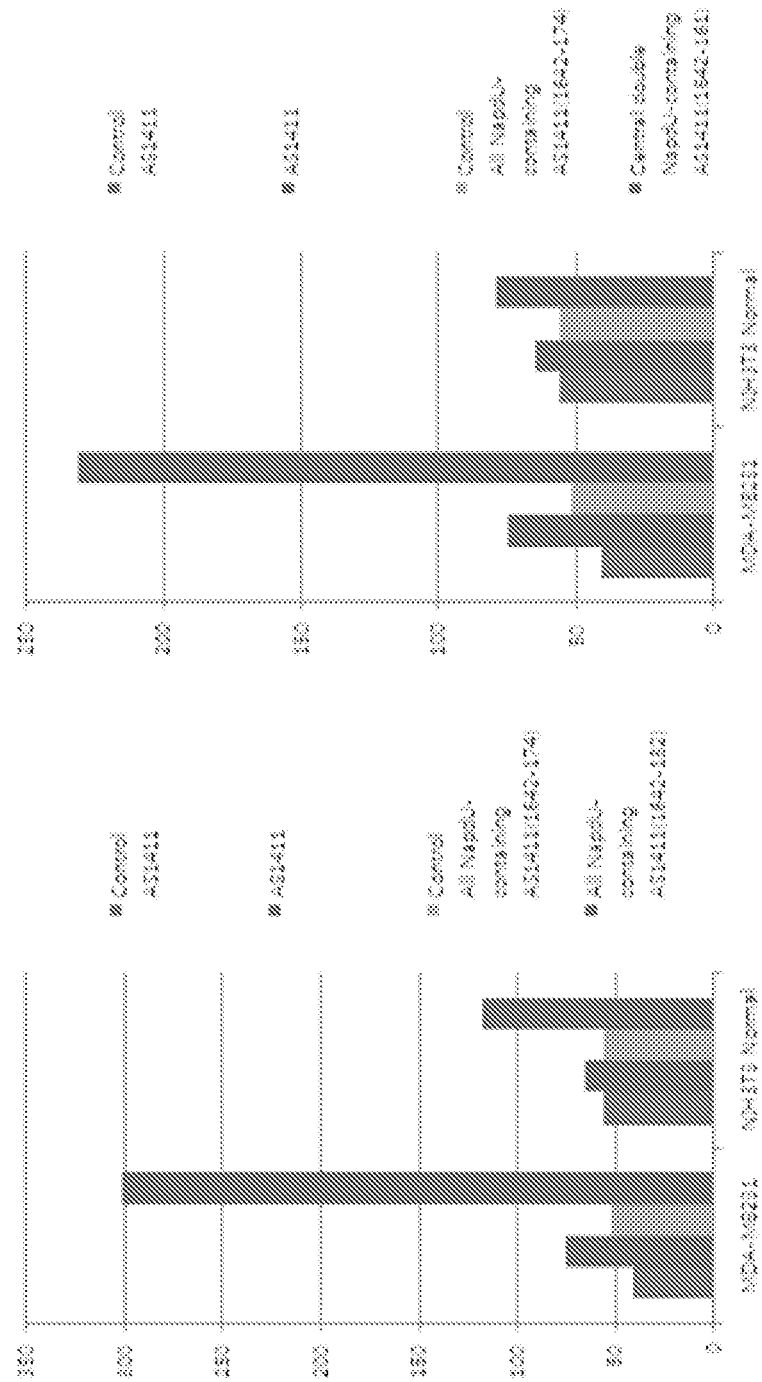
FIG. 24 shows specificities of all NapdU-containing AS1411(1642-132) and central double NapdU-containing AS1411(1642-161) in cancer and normal cell lines determined with FACS analysis.
Figure 25:
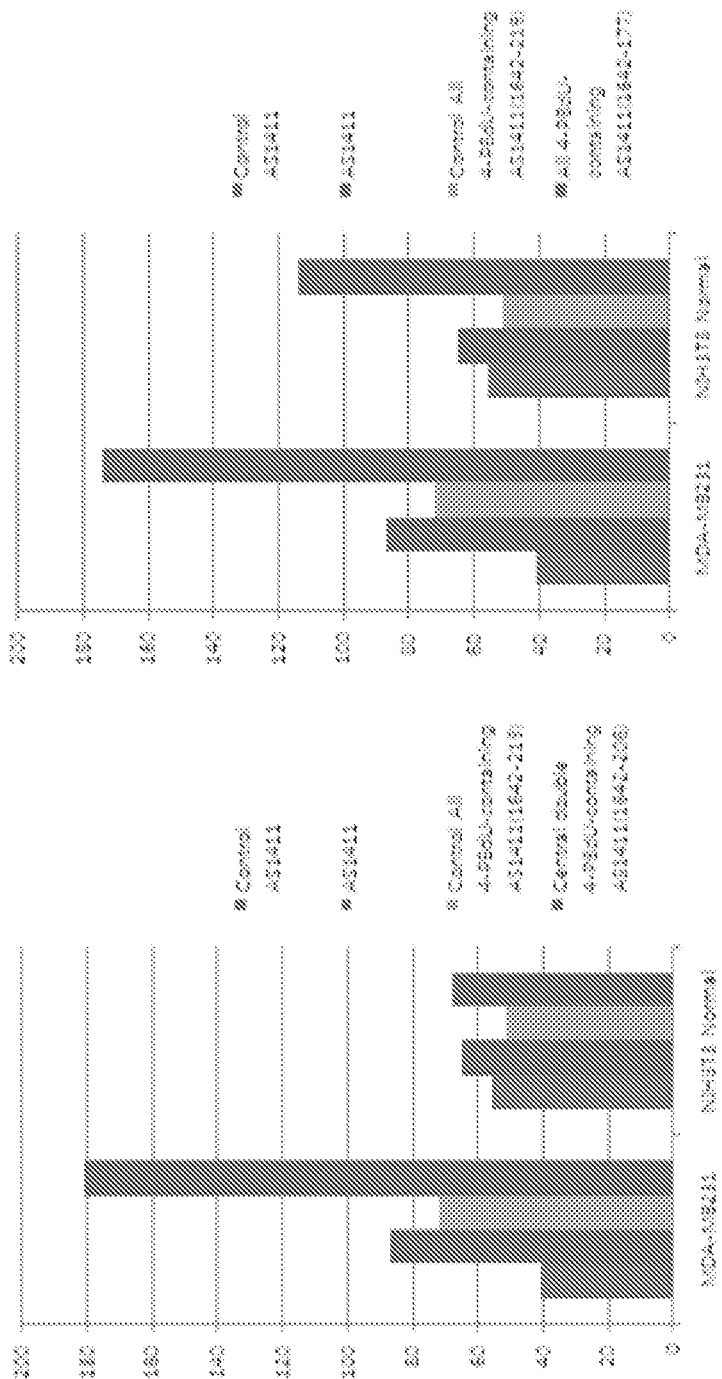
FIG. 25 shows specificities of all 4-PBdU-containing AS1411(1642-206) and central double 4-PBdU-containing AS1411(1642-177) in cancer and normal cell lines determined with FACS analysis.
Figure 26:
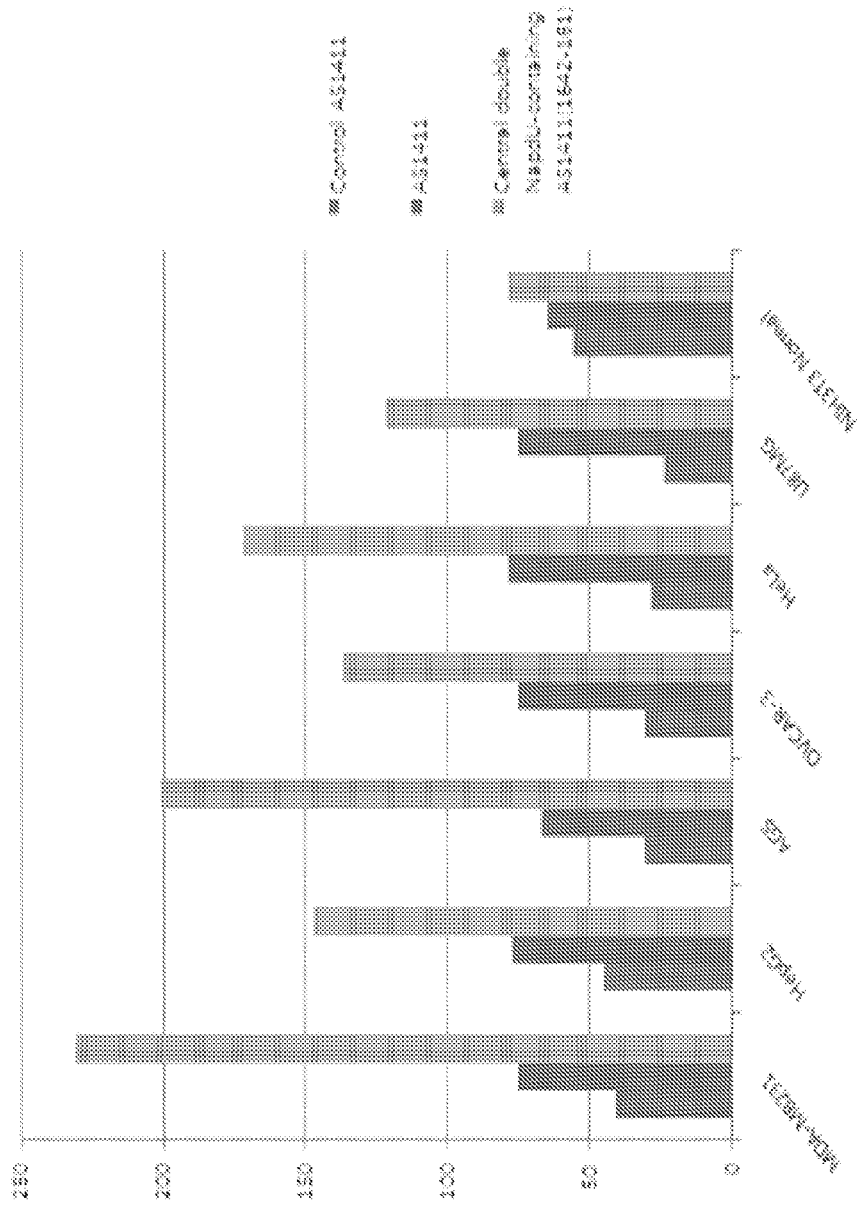
FIG. 26 shows results of a quantification of FACA analysis data of AS1411 and central modified dU-containing AS1411 binding to nucleolin on various cell lines

The results for Cy3-labeled NapdU-containing GRO29A compounds are shown in FIG. 7. FIG. 7 shows the results (fluorescence intensity) measured by fluorescence analysis of Cy3-labeled NapdU-containing GRO29A compounds targeting C6 cells with excitation 488 nm and emission 543 nm 4 different compounds. The fluorescence quantification of 18 different Cy3-labeled NapdU-containing GRO29A compounds which were bound and target nucleolin protein in C6 cells. X-axis indicated No. of compounds. These data are presented as means±SD calculated from quadruple wells. As shown in FIG. 7, compound nos. 1642-70, 1642-71, 1642-72 and 1642-73 had extensively and better binding affinity to the plasma membrane of the C6 cells than the Cy3-labeled GRO29A.

Example 3

FACS (Fluorescence Activated Cell Sorter) Analysis 3.1: Cell Culture

All cultures were grown in a humidified incubator maintained at 37° C. with 95% air/5% $CO_2$. C6 (Glioma cancer), MDA-MB231 (Breast cancer), MG63 (osteosarcoma), U87MG (Glioma cancer), OVCAR-3 (Ovarian carcinoma), and HeLa (Cervical Carcinoma) human cancerous cells were obtained from the American Type Culture Collection (ATCC) and were propagated in DMEM medium supplemented with 10% fetal bovine serum (FBS), penicillin (100 IUmmL$^{-1}$), and streptomycine (100 IUmmL$^{-1}$). AGS (Gastric cancer, ATCC) and HepG2 (Liver cancer, ATCC) cells were grown in RPMI1640 and MEM (Invitrogen, Carlsbad, Calif.), respectively. NIH3T3 cells (Normal, ATCC) were cultured in DMEM supplemented with 10% FBS and antibiotics (100 IUmmL$^{-1}$ penicillin, 100 IUmmL$^{-1}$ streptomycin, Invitrogen, Carlsbad, Calif.). The modified aptamer was dissolved in culture media before addition to the cell cultures for the cell proliferation assay.

3.2: FACS (Fluorescence Activated Cell Sorter) Analysis

Cells monolayers were detached by 2 mM EDTA, filtered with 40 μm Cell strainer (BD Falcon), and then washed with HBSS solution (Gibco). The each Cy3-labeled aptamer (AS1411 or modified dU containing AS1411, 100 pmol) was incubated with cells respectively in 200 μL of HBSS solution on ice for 60 min. Cells were washed three times with 500 μL of HBSS solution and suspended in 1 mL of 1% paraformaldehyde solution. The fluorescence was determined with FACSCalibur (BD Biosciences) by counting 10,000 events.

The obtained results in various cell lines are shown in FIGS. 8-21. As shown in FIGS. 8-21, the intensities corresponding to the peaks for the modified dU-containing aptamer (modified dU containing AS1411) is higher than those of non-modified aptamer (AS1411), indicating that the modified aptamer has a higher specificity to cancer cells compared to the non-modified aptamer.

FIGS. 22-26 shows the results of quantification of the results of FACS analysis for various cell lines as shown in FIGS. 8-21, indicating that chemical modification of thymidine at the particular region of AS1411 with Bz, Nap, or 4-PB, would form more stable G-quardruplex structure via hydrophobic cavities and enhance the potential binding affinity of AS1411 to cancer cells. As shown in FIG. 22-26, Al modified dU-containing AS1411 (GGZGGZGGZGGZZGZGGZGG-ZGGZGG; SEQ ID NO: 208 or SEQ ID NO: 210), a central double modifiddU-containing AS1411(GGTGGTGGTGG-ZZGTGGTGGTGGTGG) and several central double and a more modifieddU-containing AS1411(GGTGGTGGTGG-ZZGTGGTGGTGGZGG(SEQ ID NO: 142 or SEQ ID NO: 187), GGTGGTGGTGGZZGZGGTGGTGGTGG(SEQ ID NO: 144), GGTGGTGGZGGZZGTGGTGGTGGTGG (SEQ ID NO: 147 or SEQ ID NO: 192) and GGZGGTGGTG-GZZGTGGTGGTGGTGG(SEQ ID NO: 149 or SEQ ID NO: 194)) increase binding to nucleolin on various cancer cell lines compare to AS1411.

In particular, both of central double modified dU-containing and a more modified dU-containing AS1411 have been shown same or similar binding to various cancer cell lines. The activity between central double modification and a more modification of AS1411 were measured through the FACS analysis as described above, and the obtained results are shown in FIG. 23. A more modification on any position of central double modified dU-containing AS1411 was not increased binding to nucleolin on various cancer cell lines, indicating that the modification of the central region (2 bases) may be critical region for the modification of the aptamer to effect on the affinity of the aptamer to nucleolin.

Example 4

MR Imaging

C6 rat glioma cells (ATCC) were cultured in Dulbecco's modified Eagle's medium (Invitrogen), supplemented with 10% heat-inactivated (65° C. for 20 min) fetal bovine serum (Invitrogen) with 1% antibiotics (Invitrogen), in a standard incubator (5% $CO_2$ atmosphere at 37° C.). 5×10$^6$ cells of the cultured C6 cells were transplanted into subcutaneous tissue of both thigh of nude mice (male, BALB/c, 7-weeks old, Chalsriver).

T2 axial images were obtained using 1.5-T MR imager (GE Medical Systems, Milwaukee, Wis., USA) in animal coil box. During the experimentation, the tumor-bearing nude mice were intraperitoneal injections of 50 mL of a ketamine and xylazine (2:1) solution for anesthesia. The temperature and respirations of the tumor-bearing nude mice were monitored by a rectal thermistor. The sequence parameters for repetitive time (TR) and echo time (TE) were 1400 and 55.8 ms, respectively.

MNP@$SiO_2$(RITC)-(PEG)/COOH/pro-N/$NH_2$ nanoparticles (MF, 2 mg/mL) were purchased from Biterials (Seoul, Korea) and prepared as previously described (17). Carboxyl moieties (1.1×10$^4$/nanoparticle) of the MF particles (size; 50 nm; hydrodynamic diameter; 58.1 nm) were covalently linked to a 5'—$NH_2$-modified AS1411 aptamer (SEQ ID NO: 2) or the modified dU containing AS1411 aptamer using N-(3-dimethylaminopropyl)-N-ethylcarbodiimide (EDC) (MF:aptamer molar ratio in conjugation reaction, 1:3, Sigma) for 1 h at room temperature. The AS1411-MF conjugates were washed off by centrifugation at 22,250 g for 10 min and resuspended in selection buffer solution (50 mM Tris-HCl, pH 7.4). Amine groups (6.4×10$^4$/nanoparticle) protected by the Fmoc group were released by 20% piperidine (Sigma) in an N,N-dimethylformamide solution (Sigma). After 1 h of incubation, the AS1411-MF particles were washed off twice with Tris buffer (pH 7.4) and briefly sonicated.

Figure 27:
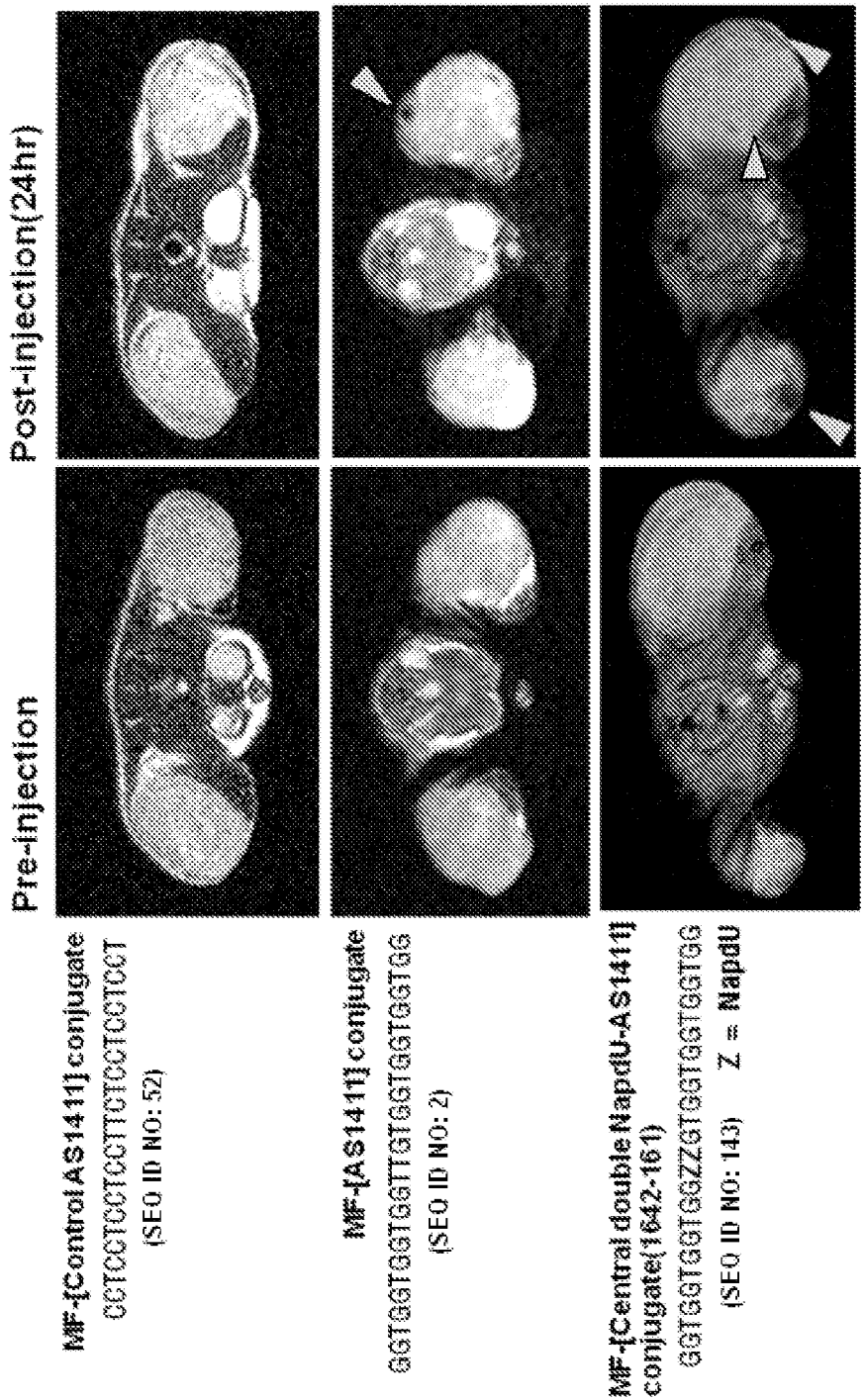
FIG. 27 shows MR images of tumor-bearing mice before and after tail-vein injection of central double NapdU-containing AS1411(1642-161), wherein dark signal intensities at tumor sites were detected in AS1411-MF particle- and modified AS1411-MF-injected mice (arrowhead).

The AS1411-MF particle and modified dU containing AS1411 (central double NapdU-containing AS1411(1642-161))-MF particle were suspended in PBS, and injected into the tumor-bearing nude mice through tail-vein injection in the amount of 5 mg/kg of body weight. T2-weighted MR images were obtained from the both thigh of the tumor-bearing nude mice before and 24 hr after intravenous injection of AS1411-MF or AS1411(1642-161)-MF, and shown in FIG. 27. As shown in FIG. 27, T2-weighed MR images from tumor-bearing mice injected with modified AS1411-MF showed the AS1411-MF particles as bigger block spots than that of AS1411. No T2-negative images were observed in the control AS1411-MF particle-injected tumor-bearing mice.

Example 5

Cell Proliferation Assay

To test another functional activity of the chemically modified nucleolin aptamer on tumor cell death, cell proliferation test was performed by MTT assay, based on the fact that nucleolin aptamer has antiproliferative effects by specifically binding to the nucleolin transmembrane protein in cancer cells.

To determine cell survival after exposure to the chemically modified aptamer for 5 days, measurement of cell proliferation was preformed colorimetrically by 3-(4,5-dimethylthiazol-2-yl)-5-(3-carboxymethoxyphenyl)-2-(4-sulphophenyl)-2H-tetrazolium (MTS) assay, using the CellTiter96 Aqueous One Solution Reasgent (Promega). Cells were seeded onto 96-well plates at 4×10$^5$ cells well$^{-1}$ in 100 μL of medium, and the tested modified aptamer was added to allow to attach for 24 hr. The cell monolayer was washed with phosphate buffered saline (PBS) to remove unattached cells, and the cells were maintained in serum-free medium (SFM) for 24 h, and then washed with PBS. Fresh SFM with the modified aptamer was added, and the cells were incubated for an additional 5 days. Subsequently, the cells were exposed to MTS for 15 min and absorbance was measured using a microplate reader (Dynex Technology, Chantilly, Va., USA) at an optical density (OD) of 490 nm. OD values from the control cells were designated 100% as a standard.

For test the activity CRO29A on cell proliferation, 4M of each compound, numbers 1642-39, 1642-51 and 1642-19, Cy3-labeled CRO29A, and Cy3-labeled GRO29A were added directly to MDA-MB231 cells (Breast cancer, ATCC) and incubated for 1 day. The cell viability (%) was measured based on that of control (100%). The control is a cell group without treatment of aptamer, and the results are shown in FIG. 6.

Figure 6:
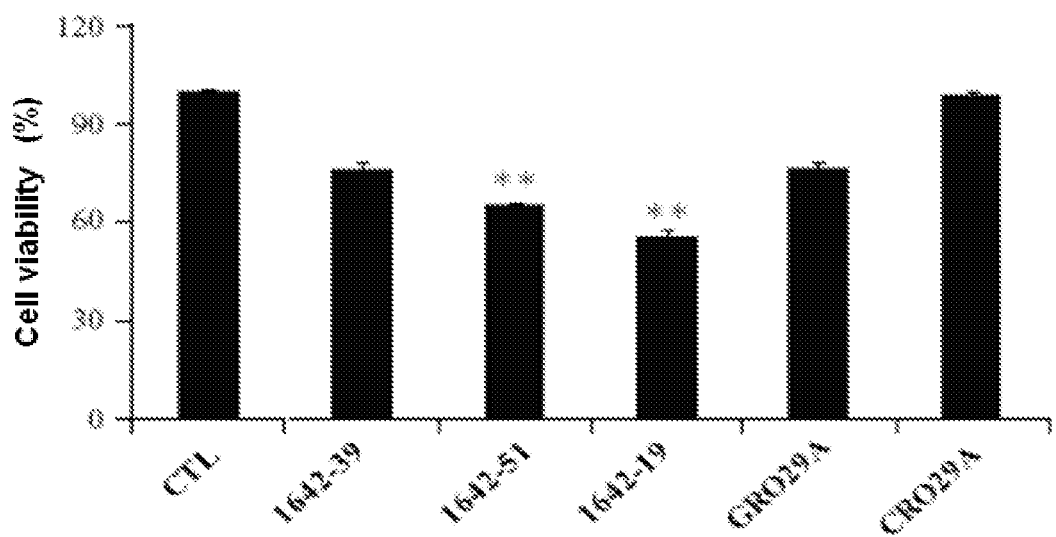
FIG. 6 shows cell viabilities measured by MTT assay to show anti-proliferation effects.

FIG. 6 shows anti-proliferation effects measured by MTT assay. 4 mM of each compounds was treated at $2\times10^5$ C6 cells per well. Data are represented as means±standard error of means (**$P<0.005$ unpaired t-test). The compounds numbers 1642-51 and 1642-19 showed significantly higher antiproliferative effect than the Cy3-labeled GRO29A, representing 55% and 65% of cell viability.

Figure 28:
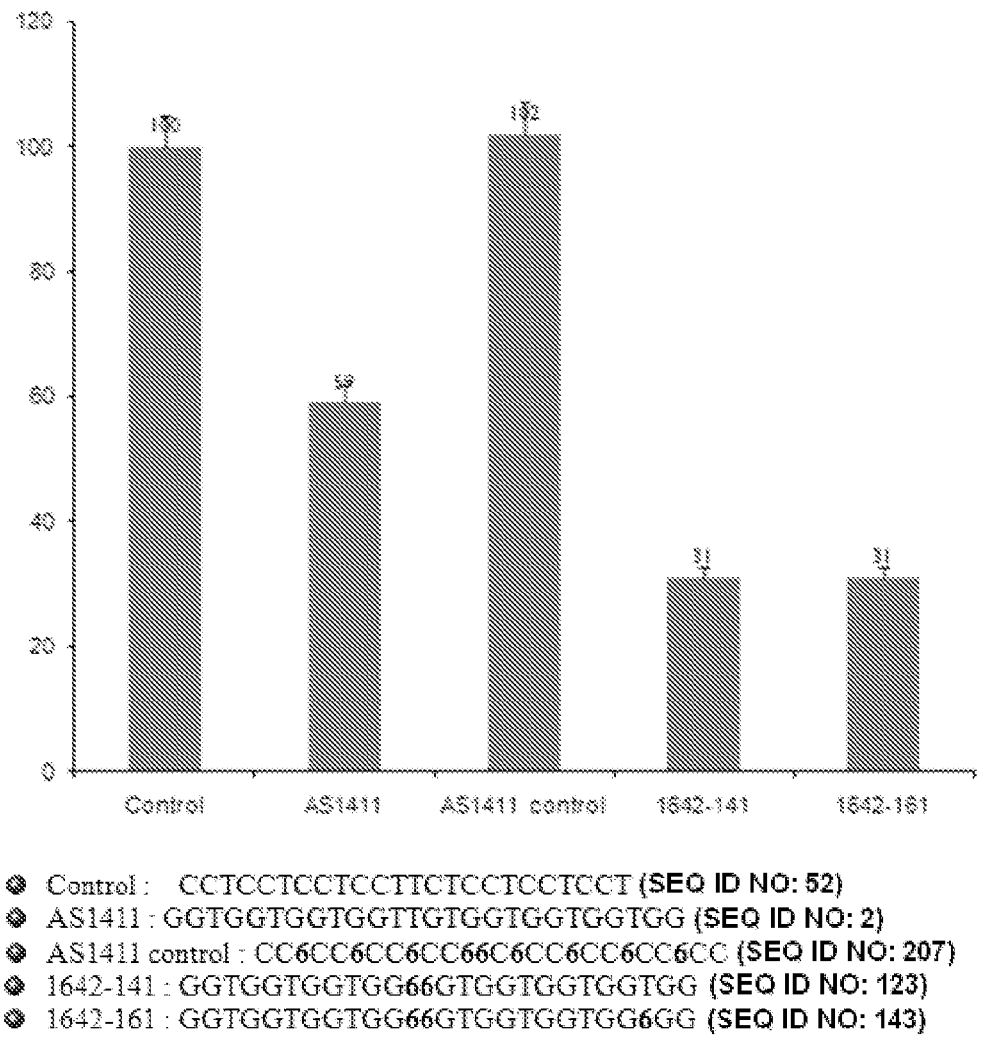
FIG. 28 shows the effect of central double NapdU-containing AS1411 on the cell viability of MDA-MB231 breast cancer cells.

To confirm that the central double modification of the aptamer is also critical in treating cancer, the effect of central double NapdU-containing AS1411 (4 μM) on the viability of MDA-MB231 breast cancer cells (ATCC) were measured by the method as described above, and the results are shown in FIG. 28 (wherein, '6' refers to NapdU). The results indicate that central double NapdU-containing AS1411 showed higher inhibition effect than AS1411.

The inventors synthesized various compounds of Cy3-labeled modified dU-containing AS1411(or GRO29A) with single or multiple modifieddUs to increase their binding affinity to nucleolin proteins in the cell membranes of cancer cells. The quantification of fluorescent signals demonstrated that a variety of chemically modified AS1411 compounds using modifieddU had varied binding affinity to cancer cells. The number and position of substituents in the AS1411(or GRO29A) nucleotides were compared with the original sequences of AS1411(or GRO29A). Our statistical analysis and confocal microscopy imaging showed that at least three compounds, numbers 1642-19 (TTTGGTGGTGGTGGT-TGTGGTGGTGGZGG, Z=BzdU, SEQ ID NO: 15), 1642-39 (TTTGGTGGTGGTGGZZGTGGTGGTGGTGG, Z=BzdU, SEQ ID NO: 32), and 1642-51 (ZTZGGTGGTG-GTGGZZGTGGTGGTGGTGG, Z=BzdU, SEQ ID NO: 44) out of 47 different Cy3-labeled BzdU-containing GRO29A, resulted in a significant increase in targeting the C6 cells. To assess whether the number and position of the BzdU incorporated into GRO29A had the influence of targeting and binding the C6 cells the chemically modified sequences of the 47 different compounds of Cy3-labeled BzdU-containing GRO29A were compared with regard to their fluorescent activity in targeting of the C6 cells. For incorporation of NapdU into GRO29A, some central double modification, No. 1642-70(ZTTGGTGGTGGTGGZZGTGGTGGTGGTGG, SEQ ID NO: 64), 1642-71 TZZGGTGGTGGTGGZZGTG-GTGGTGGTGG, SEQ ID NO: 65), 1642-72(ZTZGGTG-GTGGTGGZZGTGGTGGTGGTGG, SEQ ID NO: 66) and 1642-73(ZZGGTGGTGGTGGZZGTGGTGGTGGTGG, SEQ ID NO: 67) had extensively and better binding affinity to the plasma membrane of the C6 cells than the Cy3-labeled GRO29A. There are 12 thymidine nucleotides in the GRO29A sequence that can be substituted with modifieddU such as BzdU and NapdU. One fixed incorporation of BzdU at the $12^{th}$ thymidine, resulted in the highest binding affinity to the cancer cells and showed increased targeting affinity. In addition, most of the double incorporated BzdU or NapdU at the $7^{th}$ and $8^{th}$ thymidine, in the GRO29A compound, produced either a slight improvement or a significant improvement in the binding affinity for the C6 cells. Other random heavy modification of AS1411 did not result in a significant increase in the binding affinity for the C6 cells. These findings imply that chemical modification of thymidines at the central double region of GRO29A with modifieddU such as BzdU or NapdU forms a more stable G-quadruplex structure via hydrophobic cavities and enhances the potential binding affinity of GRO29A for cancer cells. At the results of FACS analysis with modifieddU-containing AS1411, central double modifieddU-containing AS1411(GGTGGTGGTGG-ZZGTGGTGGTGGTGG, Z=BzdU(SEQ ID NO: 98), NapdU(SEQ ID NO: 143) and 4-PBdU(SEQ ID NO: 188)) had extensively and better binding affinity to the nucleolin of cancer cell lines than AS1411. (see FIG. 29).

Figure 29:
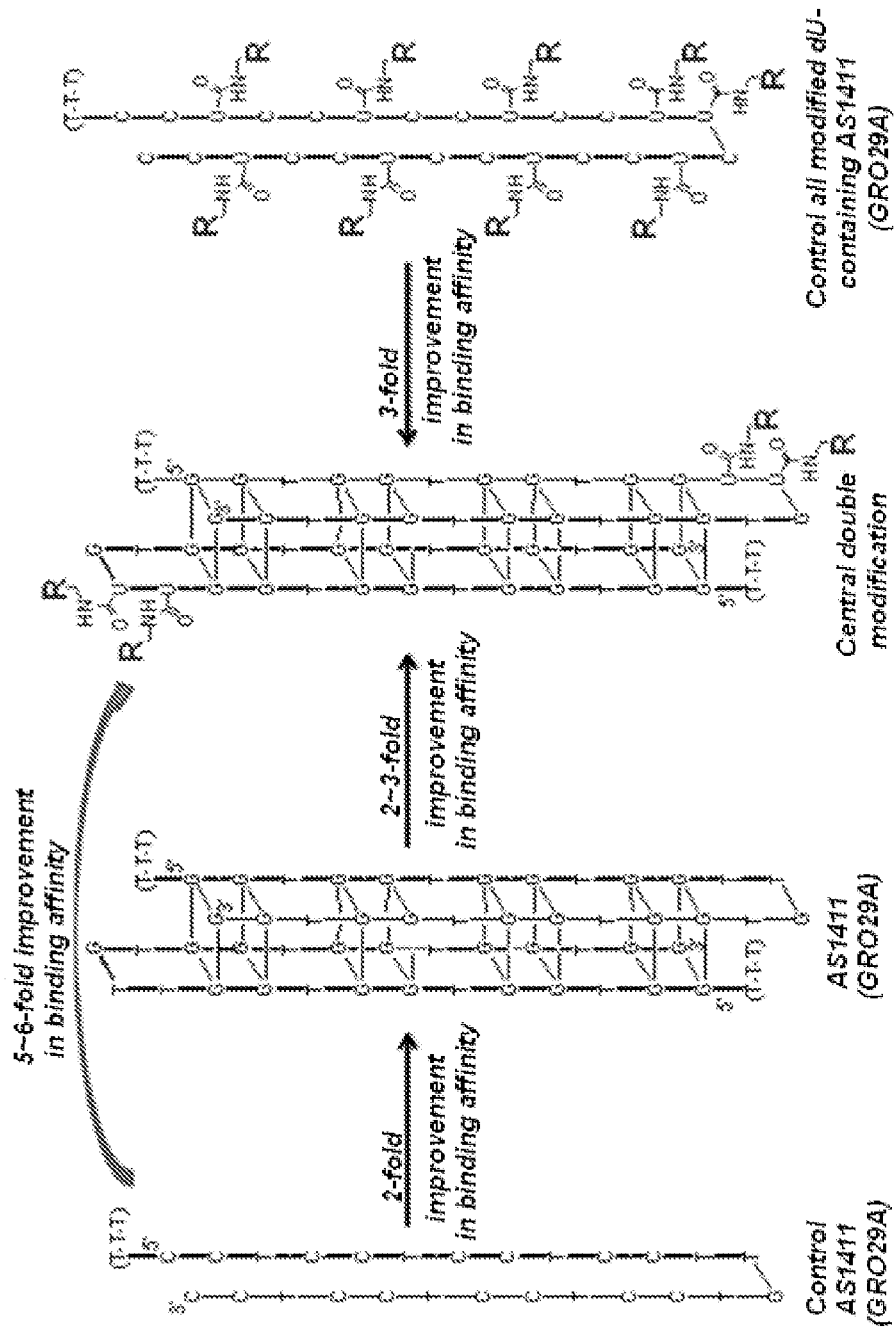
FIG. 29 shows the relation between structure and activity of central double modified dU-containing AS1411 (or GRO29A).

FIG. 29 shows a relation between structure and activity of central double modified dU-containing AS1411 (or GRO29A). The position and structure of chemical modification in central double modification and the original sequence of AS1411 were drawn in G-quadruplex structure that normally forms by dimerization of AS1411 aptamers to bind to nucleolin protein.

The results of the examples highlight the fact that chemical modifications can directly applied to alter existing aptamers thereby increasing their binding affinity for targets without a significant increase in time or labor for the SELEX procedure. Such chemically modified aptamers could be used as a valuable clinical tool for identifying serious cancer disease, in a very early stage, and evaluation of cancer therapy. However, further analysis including the study of diverse existing aptamers and their targets as well as study of resistance to enzymatic degradation, biostability in vivo, and optimization of the number and positioning of the modified dU such as BzdU, NapdU and 4-PBdU compounds in the sequence of the existing aptamers must be studied before in vivo application is considered for the detection and treatment of cancers.

---

What is claimed is:

1. Nucleolin-specific aptamer, wherein the aptamer has the sequence of SEQ ID NO: 3, and two thymidines(T) present at at least $12^{th}$ and $13^{th}$ positions of the nucleotide sequence are independently substituted with a modified pyrimidine nucleoside, and wherein the modified pyrimidine nucleoside is deoxyuridine(dU), deoxycytidine(dC), uridine(U), or cytidine(C) having a hydrophobic group at 5 position:

NGGTGGTGGTGGTTGTGGTGGTGGTGGN    (SEQ ID NO: 3)

wherein each N is absent or 1 to 20 nucleosides, which is independently selected from the group consisting of adenosine(A), thymidine(T)/uridine(U), cytidine(C), and guanosine(G), and the positions are counted starting from 'G' immediately following 'N' at 5'-end, wherein the hydrophobic group is selected from the group consisting of a benzyl group, a naphthyl group, or a pyrrolebenzyl group.

2. The nucleolin-specific aptamer according to claim 1, wherein the aptamer has the sequence of SEQ ID NO: 1 or 2, and two thymidines(T) present at at least $15^{th}$ and $16^{th}$ positions of SEQ ID NO: 1 or at least $12^{th}$ and $13^{th}$ positions of SEQ ID NO: 2 are independently substituted with a modified pyrimidine nucleoside, and wherein the modified pyrimidine nucleoside is deoxyuridine(dU), deoxycytidine(dC), uridine (U), or cytidine(C) having a hydrophobic group at 5 position.

3. The nucleolin-specific aptamer according to claim 1, wherein the modified pyrimidine nucleoside is selected from the group consisting of 5-(N-benzylcarboxyamide)-2'-deoxyuridine(called BzdU), 5-(N-naphthylcarboxyamide)-2'-deoxyuridine(called NapdU), 5-(N-4-pyrrolebenzylcarboxyamide)-2'-deoxyuridine(called 4-PBdU), 5-(N-benzylcarboxyamide)-2'-deoxycytidine (called BzdC), 5-(N-naphthylcarboxyamide)-2'-deoxycytidine (called NapdC), 5-(N-4-pyrrolebenzylcarboxyamide)-2'-deoxycytidine (called 4-PBdC), 5-(N-benzylcarboxyamide)-2'-uridine (called BzU), 5-(N-naphthylcarboxyamide)-2'-uridine (called NapU), 5-(N-4-pyrrolebenzylcarboxyamide)-2'-uridine(called 4-PBU), 5-(N-benzylcarboxyamide)-2'-cytidine (called BzC), 5-(N-naphthylcarboxyamide)-2'-cytidine (called NapC), and 5-(N-4-pyrrolebenzylcarboxyamide)-2'-cytidine (called 4-PBC).

4. The nucleolin-specific aptamer according to claim 1, wherein at least one thymidine in addition to the two thymidines(T) present at $12^{th}$ and $13^{th}$ positions of SEQ ID NO: 3 are additionally substituted with the modified pyrimidine nucleoside, and the positions are counted starting from 'G' immediately following 'N' at 5'-end.

5. The nucleolin-specific aptamer according to claim 2, wherein at least one thymidine in addition to the two thymidines(T) present at $15^{th}$ and $16^{th}$ positions of SEQ ID NO: 1 or $12^{th}$ and $13^{th}$ positions of SEQ ID NO: 2 are additionally substituted with the modified pyrimidine nucleoside, myeloproliferative disorders, carcinomas of solid tissue, sarcomas, melanomas, adenomas, hypoxic tumors, squamous cell carcinomas of the mouth, throat, larynx, or lung, genitourinary cancers, hematopoietic cancers, head and neck cancers, and nervous system cancers, and benign lesions.

6. A pharmaceutical composition containing the nucleolin-specific aptamer of claim 1.

7. A method of inhibiting nucleolin, comprising the step of administering the nucleolin-specific aptamer of claim 1 to a subject or a sample comprising nucleolin-expressing cells.

8. A method of inhibiting hyperproliferation of cell cased by nucleolin, comprising the step of administering the nucleolin-specific aptamer of claim 1 to a subject or a sample comprising nucleolin-expressing cells.

* * * * *